United States Patent [19]

Floyd, Jr. et al.

[11] E Re. 29,469

[45] Reissued Nov. 8, 1977

[54] HYDROXYLATED 15-DEOXY DERIVATIVES OF 9-HYDROXYL-13-TRANS-PROSTENOIC ACID

[75] Inventors: Middleton Brawner Floyd, Jr., Suffern, N.Y.; William James McGahren, Demarest, N.J.; Robert Eugene Schaub, Upper Saddle River, N.J.; Martin Joseph Weiss, Oradell, N.J.

[73] Assignee: American Cyanamid Company, Stamford, Conn.

[21] Appl. No.: 682,691

[22] Filed: May 3, 1976

Related U.S. Patent Documents

Reissue of:

[64] Patent No.: 3,950,406
Issued: Apr. 13, 1976
Appl. No.: 480,989
Filed: June 19, 1974

U.S. Applications:

[63] Continuation-in-part of Ser. No. 274,769, July 24, 1972, abandoned.

[51] Int. Cl.[2] ..... C07C 177/00

[52] U.S. Cl. ..... 560/121; 260/410.9 R; 260/413; 260/514 D

[58] Field of Search ..... 260/514 D, 468 D

[56] References Cited

U.S. PATENT DOCUMENTS 3,770,776 11/1973 Collins et al. ..... 260/345.7

*Primary Examiner*—Robert Gerstl
*Attorney, Agent, or Firm*—Denis A. Polyn

[57] ABSTRACT

This disclosure describes certain 15-deoxy prostanoic acid derivatives having a hydroxy group further along in the beta-chain, useful as bronchodilators; hypotensive agents, anti-ulcer agents, or as intermediates.

39 Claims, No Drawings

HYDROXYLATED 15-DEOXY DERIVATIVES OF 9-HYDROXYL-13-TRANS-PROSTENOIC ACID

Matter enclosed in heavy brackets [ ] appears in the original patent but forms no part of this reissue specification; matter printed in italics indicates the additions made by reissue.

CROSS REFERENCE TO RELATED *PATENT AND* APPLICATION

This application is a *reissue application of our original U.S. Pat. No. 3,950,406, dated Apr. 13, 1976, Serial No. 480,989, filed June 19, 1974; which is a* continuation-in-part of our copending application Ser. No. 274,769, filed July 24, 1972, now abandoned.

BRIEF SUMMARY OF THE INVENTION

This invention relates to novel hydroxy substituted 15-deoxy prostanoic acids and derivatives as well as to intermediates and methods for their preparation. The novel compounds of this invention may be represented by the following general formulae: wherein formula A has the absolute configuration of the naturally-occurring mammalian prostaglandins.

A

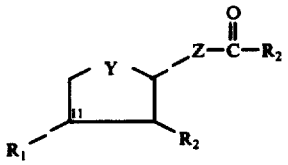

B

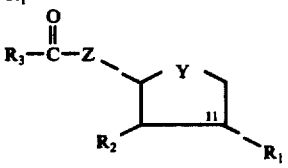

wherein $R_1$ is selected from the group consisting of hydrogen, hydroxy, lower alkoxy, tetrahydropyranyloxy, lower alkanoyloxy, ω-hydroxy substituted lower alkoxy and ω-tetrahydropyranyloxy substituted lower alkoxy; $R_2$ is a moiety selected from the group consisting of those of the formulae:

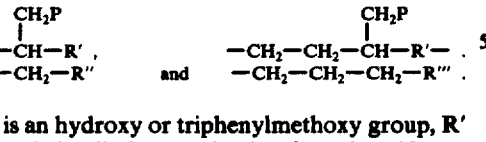

wherein P is an hydroxy or triphenylmethoxy group, R′ is a straight chain alkyl group having from 2 to 10 carbon atoms, or a straight chain alkyl group having from 2 to 6 carbon atoms and having one branched alkyl group of from 1 to 3 carbon atoms, and R″ is a straight chain alkyl group having from 2 to 10 carbon atoms and substituted with an hydroxy or triphenylmethoxy group, or a straight chain alkyl group having from 2 to 6 carbon atoms and having one branched alkyl group of from 1 to 3 carbon atoms and substituted with an hydroxy or triphenylmethoxy group or a straight chain alkenyl group having from 2 to 10 carbon atoms and substituted with a hydroxy or triphenylmethoxy group, or a straight chain alkenyl group having from 2 to 6 carbon atoms and having one branched alkyl group of from 1 to 3 carbon atoms and substituted with a hydroxy or triphenylmethoxy group; $R_3$ is selected from the group consisting of hydroxy, an alkoxy group having from 1 to 12 carbon atoms and tetrahydropranyloxy; R‴ is a straight chain alkyl group having from 2 to 10 carbon atoms and substituted with an hydroxy or triphenylmethoxy group, or a straight chain alkyl group having from 2 to 6 carbon atoms and having one branched alkyl group of from 1 to 3 carbon atoms and substituted with an hydroxy or triphenylmethoxy group; Y is a divalent radical selected from the group consisting of those of the formulae:

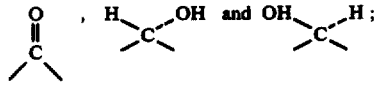

and Z is a divalent radical selected from the group consisting of those of the formulae:

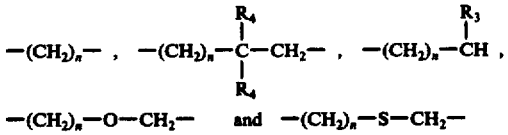

wherein n is an integer from 3 to 8 inclusive, $R_4$ is an alkyl group having up to 3 carbon atoms and $R_5$ is an alkyl group having up to 3 carbon atoms, a fluorine atom or a phenyl group; and the moiety of the formula:

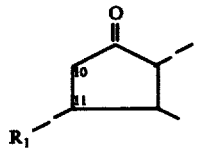

may be the divalent radical of the formula:

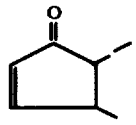

when $R_3$ is hydroxy or an alkoxy group having from 1 to 12 carbon atoms; and the moiety of the formula:

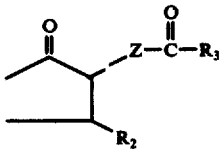

may be the divalent moiety of the formula:

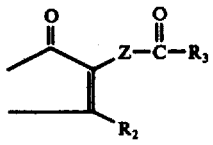

when $R_3$ is hydroxy or an alkoxy group having from 1 to 12 carbon atoms. Suitable lower alkoxy and lower alkanoyl groups contemplated by the present invention are those having up to four carbon atoms such as, for example, methoxy, ethoxy, isopropoxy, sec-butoxy, formyl, acetyl, propionyl, isobutyryl, etc.

Also embraced within the scope of the present invention are the non-toxic, pharmaceutically acceptable salts of the novel compounds of the present invention when $R_3$ is hydroxy. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine), procaine, and the like.

The novel compounds of the present invention are obtainable as yellow oils having characteristic absorption spectra. They are relatively insoluble in water but are relatively soluble in common organic solvents such as ethanol, ethyl acetate, dimethylformamide, and the like. The cationic salts of the compounds when $R_3$ is hydrogen are, in general, white to yellow crystalline solids having characteristic melting points and absorption spectra. They are relatively soluble in water, methanol and ethanol but are relatively insoluble in benzene, diethyl ether, and petroleum ether.

DETAILED DESCRIPTION OF THE INVENTION

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals. See Bergstom et al., J. Biol. Chem. 238, 3555 (1963) and Horton, Experienta 21, 113 (1965) and references cited therein. All of the so-called natural prostaglandins are derivatives of prostanoic acid.

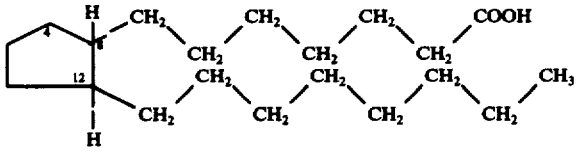

The hydrogen atoms attached to C-8 and C-12 are in trans-configuration. The natural prostaglandins represent only one of the possible optical isomers. The compounds of this convention include all possible optical isomers.

The novel compounds of the present invention may be readily prepared from certain 4-substituted cyclopentenone intermediates which may be represented by the following general formulae:

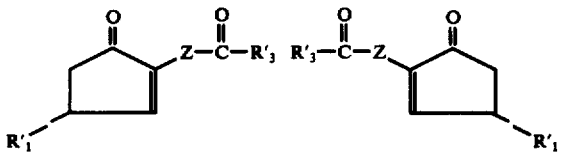

wherein $R_1'$ is hydrogen, lower alkoxy, tetrahydropyranyloxy, lower alkanoyloxy or ω-tetrahydropyranyloxy lower alkoxy; and $R_3'$ is tetrahydropyranyloxy or an alkoxy group having from 1 to 12 carbon atoms.

The 4-oxycyclopentenone intermediates may be readily prepared from 2-carbethoxycyclopentanone in accordance with the reaction schemes set forth in Flowsheets A through D. In particular, the requisite 2-(ω-carbethoxyalkyl)cyclopent-2-en-1-one intermediates (VIII) may be prepared in accordance with the following reaction scheme:

FLOWSHEET A

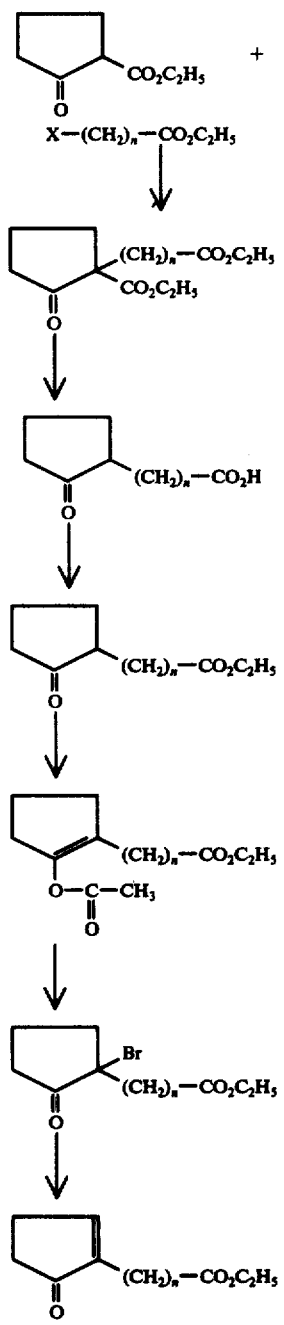

wherein n is as hereinabove defined [ans] *and* X is iodo or bromo. In accordance with this reaction scheme, the cyclopent-2-en-1-ones (VIII) are developed by first converting 2-carbethoxycyclopentanone (I) to the sodium enolate thereof by means of sodium hydride in dimethoxyethane and then treating the sodium enolate with an ethyl ω-haloalkanoate (II). There is thus obtained the corresponding 2-carbethoxy-2-(ω-carbethoxyalkyl)cyclopentanone (III) which is then hydrolyzed and decarboxylated to afford the 2-(ω-carboxyalkyl)cyclopentanone (IV). This acid is then esterified with ethanol whereby the 2-(ω-carbethoxyalkyl)cyclopentanone (V) is obtained. The reaction conditions for carrying out the above sequence of reactions are well known in the art. The conversion of the cyclopentanone (V) to the enol acetate (VI) is effected by heating with acetic anhydride in the presence of p-toluenesulfonic acid. Preparation of the enol acetate (VI) usually requires heating for a period of from about 8 to 36 hours. During this period, it is preferable to allow byproduct acetic acid to distill out in order to force the reaction to completion. The bromination of the enol acetates (VI) to the 2-bromocyclopentanones (VII) is preferably carried out in a two phase system as follows. A solution of bromine in chloroform is added to a rapidly stirred mixture of a solution of the enol acetate (VI) in chloroform and an aqueous solution of an acid acceptor such as calcium carbonate or soda ash. This addition is carried out at 0°-5° C. over a period of about 90 minutes stirring is continued for an additional period of about half an hour to a few hours, and the product (VII) is then isolated by standard procedures. The dehydrobromination of the 2-bromocyclopentanones (VII) is preferably carried out in dimethylformamide with a mixture of lithium bromide and lithium carbonate at the reflux temperature for a period of about 30 minutes to an hour or so. The so formed cyclopent-2-en-1-ones (VIII) are also isolated by standard procedures well known in the art. Substitution of $X—(CH_2)_n—C(R_4)_2—CH_2—CO_2C_2H_5$ for (II) in Flowsheet A and carrying through the sequence of transformations illustrated therein is productive of the following cyclopent-2-en-1-ones (VIIIa):

(VIIIa)

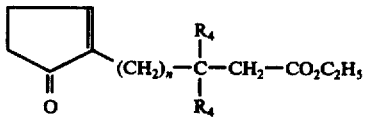

wherein X, n, and $R_4$ are as hereinabove defined.

The required cyclopent-2-en-1-one intermediates of general structure (XVI), wherein the side-chain has a lower alkyl group, fluorine atom or phenyl group alpha to the carbethoxy function, may be prepared in accordance with the following reaction scheme:

FLOWSHEET B (IX)

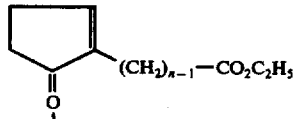

(X)

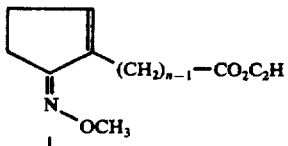

-continued (XI)

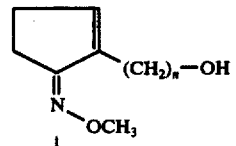

(XII)

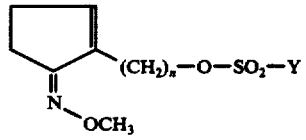

(XII)

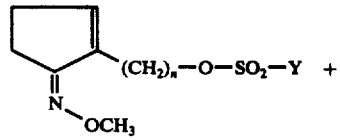

(XIII)

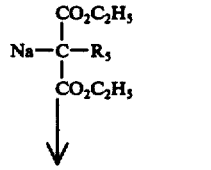

(XIV)

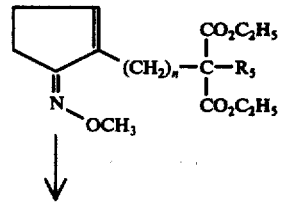

(XV)

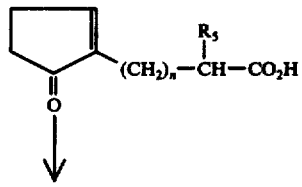

(XVI)

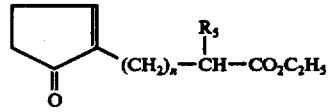

wherein n and $R_5$ are as hereinabove defined, and Y is a methyl or p-tolylradical. In accordance with this reaction scheme, the 2-(ω-carbethoxyalkyl)cyclopent-2-en-1-ones (IX), prepared as described in Flowsheet A for the preparation of (VIII) where n is 2-7, inclusive, are converted to the corresponding 1-methoximino-2-(ω-carbethoxyalkyl)-2-cyclopentenes (X) by treatment with methoxyamine. With the ring carbonyl function thus blocked it is possible to effect a preferential reduction of the ester group by treatment with diisobutylaluminum hydride. The resulting alcohol (XI) is converted to a mesylate or tosylate derivative (XII), which undergoes displacement on treatment with the sodium salt of a diethyl substituted malonate (XIII) to provide the disubstituted malonate derivatives (XIV). Hydrolysis and decarboxylation as well as concomittant cleavage of the methoximino blocking group provides the desired 2-(ω-carboxy-ω-substituted alkyl)cyclopent-2-en-1-ones (XV), which are readily converted to the corresponding ester (XVI) by the usual Fisher procedure.

The requisite 2-(ω-carbethoxy-3-oxa-alkyl)cyclopen-2-en-1-ones (XXII) may be prepared in the procedure the reaction scheme of Flowsheet C, wherein n is as hereinbefore defined.

FLOWSHEET C

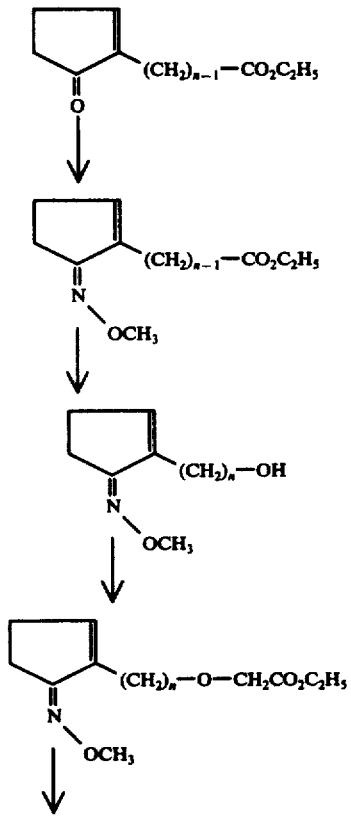

-continued

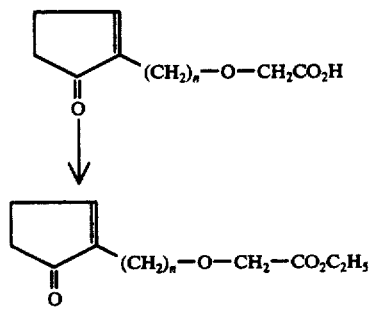

In accordance with the reaction scheme shown in Flowsheet C, for the preparation of the oxa derivatives (XXII), an appropriate 2-(ω-carbethoxyalkyl)cyclopent-2-en-1-one (XVII) is converted to the corresponding methoxime (XVIII), the ester function of which is then preferentially reduced with diisobutylaluminum hydride to afford the methoxime alcohol (XIX). The alcohol (XIX) is converted on treatment with n-butyl lithium to the lithio alcoholate, which then is O-alkylated by reaction with ethyl bromoacetate to provide (XX). Hydrolysis with acetone-aqueous hydrochloric acid furnishes the deblocked keto-acid (XXI), which is then re-esterified with ethanol in the presence of p-toluenesulfonic acid to give the required 2-(ω-carbethoxy-3-oxa-alkyl)cyclopent-2-en-1-one (XXII). O-Alkylation can also be accomplished by treatment of the lithio alcoholate of (XIX) with sodium or other metal salt of bromoacetic acid, in which case the free carboxylic acid corresponding to ester (XX) is obtained. Hydrolysis as for (XX) provides the keto acid (XXI).

Some of the transformations involved in the preparation of the 4-oxycyclopentenone intermediates are set forth in the following reaction scheme:

FLOWSHEET D

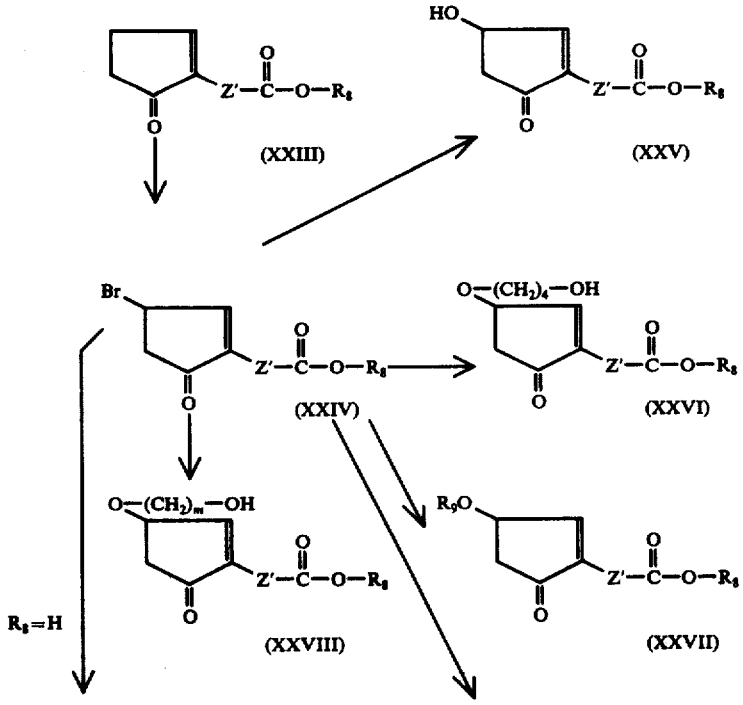

-continued

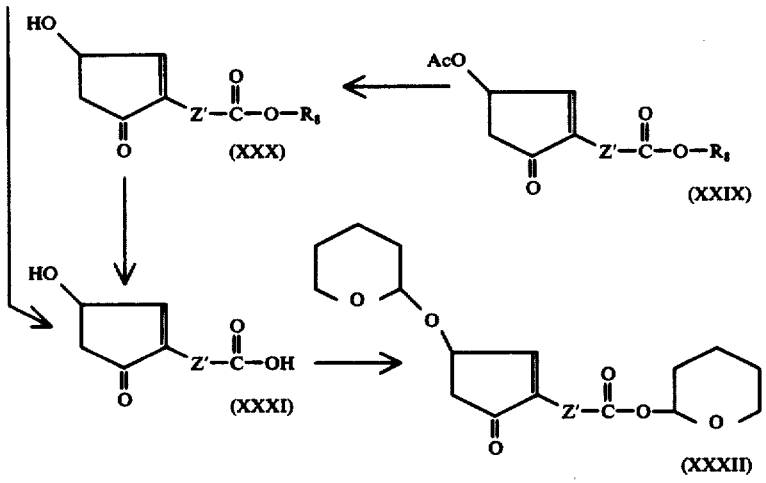

wherein $R_8$ is hydrogen or lower alkyl, $R_9$ is lower alkyl, and Z' is as hereinabove defined for Z except that it does not include the moiety: $—(CH_2)_n—S—CH_2—$, and m is an integer from 2 to 5, inclusive. Introduction of the 4-oxy-function into the 4-unsubstituted cyclopentenones (XXIII) is accomplished by first halogenating the 4-position with an allylic halogenating reagent, preferably N-bromosuccinimide. The resulting 4-bromocyclopentenone (XXIV) is then solvolyzed for the introduction of the oxy function. This step is preferably carried out in the presence of a silver salt to facilitate the displacement of the halide ion. The particular 4-oxy derivative that is formed is determined by the nature of the solvent system. Treatment of the 4-bromocyclopentenone with silver fluoroborate in water-acetone (for solubility) provides the 4-hydroxycyclopentenone (XXV). When the cyclopentenone is a carboxylic acid (i.e. $R_8$ = hydrogen), then this procedure provides (XXXI). When the solvent system is water-tetrahydrofuran, in addition to the 4-hydroxy derivative there is also obtained the 4'-hydroxybutyloxy derivative (XXVI), formed by solvolysis with tetrahydrofuran. When the solvent is only tetrahydrofuran then only the latter compound is formed. Substitution of tetrahydrofuran with alcohols, e.g., methanol, ethanol, isopropyl, butanol and the like, provides the 4-alkoxycyclopentenones (XXVII). With ethylene glycol or propylene glycol etc. the corresponding 4-(ω-substituted hydroxy alkoxy) cyclopentenone (XXVIII) is obtained. In the latter three procedures it is preferable to add a proton acceptor which will not react with (XXIV), for example, sym. collidine. When solvolysis is carried out with a silver lower alkanoate in the corresponding lower alkanoic acid, such as the silver acetateacetic acid system, the 4-acetoxy derivative (XXIX) is obtained. Careful alkaline hydrolysis of this product with potassium carbonate in aqueous methanol provides the free 4-hydroxy derivative (XXX); further hydrolysis with barium hydroxide gives the free carboxylic acid (XXXI).

In general these procedures are operable with either the free carboxylic acid or alkyl carboxylate, as desired. A particular alkyl carboxylate not provided by formula (XXIII) can be obtained by hydrolysis to the acid and esterification in the usual way, for example with the appropriate alcohol, or for a t-butyl ester with isobutylene. However, for the subsequent alanate conjugate addition process it is necessary to utilize a cyclopentenone wherein the carboxylic acid as well as all free hydroxyl groups are blocked. A particularly useful blocking group for both functions is the tetrahydropyranyl group (see for example XXXI→XXXII) since this group can easily be cleaved with weak acid under conditions which do not disrupt the subsequently-prepared, relativey-unstable 11-oxy-9-keto system (β-hydroxy-ketone). Thus, it is not possible to effect a satisfactory chemical hydrolysis of an alkyl ester or of an 11-O-alkanoyl group in an 11-oxy-9-keto prostanoic acid derivative under conditions to which this system is stable (enzymatic hydrolysis, for example with baker's yeast is possible). Of course these stability considerations do not apply in the F (9-hydroxy) series.

The 9-keto-15-deoxy-13-trans-prostenoic acids and esters of this invention, as defined in the general formula on page 1 above may be prepared from cyclopentenone (XXXVII) and the triphenylmethoxy substituted 1-alkyne (XXXIII), as depicted in Flowsheet E. In Flowsheet E, $R'_1$, $R'_3$, and Z are as hereinabove defined and $R_6$ is a moiety of the formulae:

$$\begin{array}{l} CH_2O—C(C_6H_5)_3 \\ | \\ —CH—R' \end{array} \quad \text{and} \quad —CH_2—R''' .$$

wherein R' is as hereinabove defined and R'' is a straight chain alkyl group having from 2 to 10 carbon atoms and substituted with a triphenylmethoxy group, or a straight chain alkyl group having from 2 to 6 carbon atoms and having one branched alkyl group of from 1 to 3 carbon atoms and substituted with a triphenylmethoxy group, or a straight chain alkenyl group having from 2 to 10 carbon atoms and substituted with a triphenylmethoxy group, or a straight chain alkenyl group having from 2 to 6 carbon atoms and having one branched alkyl group of from 1 to 3 carbon atoms and substituted with a triphenylmethoxy group; and $R'_6$ has all the possibilities of $R_6$ except that triphenylmethoxy is replaced by hydroxy. Also, R is a lower alkyl group of up to 4 carbon atoms, $R''_1$ is as defined above for $R_1$ except that it is not tetrahydropyranyloxy or ω-tetrahydropyranyloxy substituted lower alkoxy, and $R''_3$ is as defined above for $R_3$ except that it is not tetrahydropyranloxy.

FLOWSHEET E

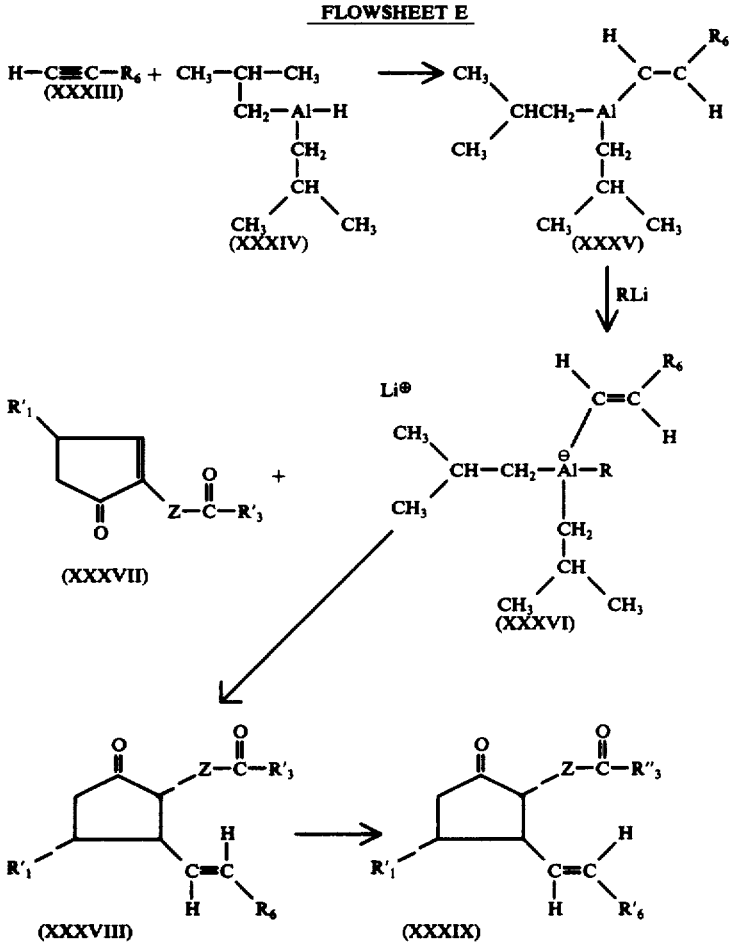

In accordance with the reaction scheme of Flowsheet E, the triphenylmethoxy substituted 1-alkyne (XXXIII) is treated with diisobutylaluminum hydride (XXXIV). This reaction of the 1-alkyne (XXXIII) with diisobutylaluminum hydride (XXIV) provides the alane (XXXV) containing the trans-double bond and is carried out in an inert solvent such as benzene, toluene, and the like at temperatures in the range of 40°-60° C. for several hours. It can also be carried out in a solvent such as tetrahydrofuran, usually in an approximate 2:1 mixture with benzene or hexane; in which case the reaction requires somewhat more vigorous conditions, usually treating at about 70°-75° C. for about eighteen hours. The subsequent reaction with methyl or n-butyl lithium (R-Li) is preferably carried out in a mixture of the above solvents with an ether-type solvent such as diethyl ether, dibutyl ether, tetrahydrofuran, and the like. This reaction is rapid and is preferably carried out at 0°-10° C. with cooling. The conjugate 1,4-addition of the resulting alanate salt (XXXVI) to the cyclopent-2-en-1-one (XXXVII) is preferably carried out at ambient temperatures for a period of 12 to 24 hours. This reaction is also best carried out in an ether-type solvent such as diethyl ether, dibutyl ether, and the like. The intermediate alanate-enolate adduct is then carefully hydrolyzed in situ with dilute hydrochloric acid with cooling, and the products (XXXVIII) are isolated in the usual manner well known in the art. Removal of tetrahydropyranyl blocking groups and of the triphenylmethyl blocking group can then be accomplished by treating with weak acid. A preferred procedure involves heating at 45° C. for 3.5 hours in a solvent system consisting of acetic acid:tetrahydrofuran:water in the proportion of 4:2:1. If (XXXVIII) is a tetrahydropyranyl ester, there is then obtained the prostenoic acid (XXXIX, $R''_3$=hydroxy).

All available evidence leads us to believe that the —CH=CH—$R_6$ function introduced by the alanate process (see XXXVIII) occupies a position trans to the 11-oxy function (when $R'_1$ is not hydrogen). Similarly, we are led to the conclusion that in the product (XXXIX) the two side-chains attached to $C_8$ and $C_{12}$ are trans to each other. However, we are not certain of this configurational relationship in product (XXXVIII) as it is obtained directly from the alanate process. These products may have the side-chains in a trans- or cis-relationships or they may be a mixture containing both the trans- and cis-isomers. This is indicated in the nomenclature of the compounds involved by the designation 8 ξ. In order to ensure a trans-relationship in both (XXXVIII) and XXIX) these products can be submitted to conditions known in the literature to equilibrate the cis-8-iso-$PGE_1$ to a mixture containing about 90% of the trans product. These conditions involve treatment with potassium acetate in aqueous methanol for 96 hours at room temperature.

An alternative procedure for the conversion of substituted 1-alkyne (XXXIII) to the 9-keto-15-deoxy-13-trans-prostenoic acids and esters of this invention entails reduction of 1-alkyne (XXXIII) with disiamylborane in an ether solvent, in accordance with Flowsheet F. The intermediate dialkyl-alkenyl borane (XXXIXa) is not isolated but is sequentially treated with trimethylamine oxide, iodine, and aqueous sodium hydroxide solution in a manner known in the art [A. F. Kluge, K. G. Untch, and J. H. Fried, Journal Amer. Chem. Soc., 94, 7827 (1972)]. This treatment provides trans-vinyl iodide (XXXIXb), a novel and useful intermediate for preparation of certain of the compounds of this invention.

Submission of the substituted vinyl iodide (XXXIXb) to metal interchange with an alkyl lithium, e.g., n-butyl lithium, at very low temperatures, e.g. −78° C., provides the vinyl lithium derivative (XXXIXc), the trans-configuration of the double bond being retained. After 1 to 4 hours, addition of a trialkyl aluminum, to the solution of the lithio derivative (XXXIXc) furnishes the lithio alanate intermediate (XXXIXd), also with retention of the trans-configuration of the double bond. The reaction of alanate (XXXIXd) with cyclopent-2-en-1-one (XXXVII) is carried out as described hereinabove (see Flowsheet E).

FLOWSHEET F

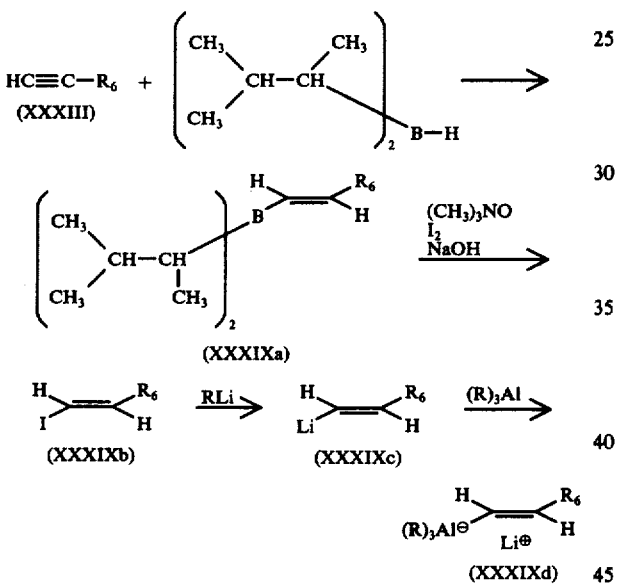

The triphenylmethoxy substituted 1-alkynes (A) and the alanes (B) derived from it are novel and useful intermediates for the synthesis of the compounds of this invention and are to be considered a part of this invention. In formulae (A) and (B), $R_6$ and R are as hereinabove defined.

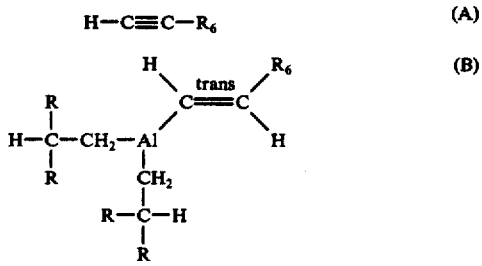

When the 11-oxy derivatives (XXXVIII or XXXIX, $R'_1$ or $R'_1$ is not hydrogen), preferably the 11-hydroxy derivative such as (XL), are treated with dilute acid it is possible to effect elimination and the formation of the corresponding $\Delta^{10}$ derivative (XLI, prostaglandins of the A type). A preferred procedure involves treatment in tetrahydrofuran: water (2:1) solvent 0.5N in hydrochloric acid for about seventy hours at ambient temperatures as set forth in the following reaction scheme. Under these conditions a tetrahydropyranyl ester will undergo hydrolysis.

When the 11-oxy derivatives (XXXVIII) or (XXXIX) or (XL) or the $\Delta^{10}$ derivative (XLI) are treated with an aqueous base system, e.g., sodium carbonate in aqueous methanol, it is possible to prepare the corresponding $\Delta^{8(12)}$ derivative (XLII), prostaglandins of the B type). The formation of the $\Delta^{8(12)}$ compound (XLII) is conveniently observed by the appearance of the ultraviolet absorption maximum due to (XLII) at about 280 mμ. This is a procedure well-known in the art. See Flowsheet G below, wherein Z, $R_2$, $R_3$ and $R''_3$ are as hereinabove defined.

FLOWSHEET G

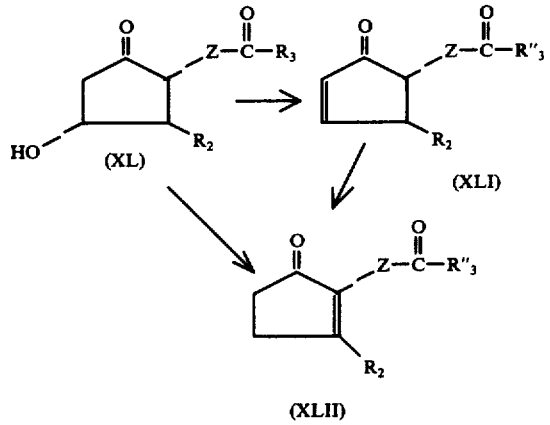

Those compounds of this invention embodying the —$CH_2$—$CH_2$— linkage at —$C_{13}$—$C_{14}$— may be prepared from the corresponding $\Delta^{13}$ derivatives, obtained via the alanate process, by catalytic reduction, preferably at low pressure with a noble metal catalyst in an inert solvent at ambient temperatures.

The 11 -oxy-9-keto derivatives of this invention can be converted to the corresponding 9-hydroxy derivatives. If this conversion is effected with sodium borohydride, the product is a mixture of 9α- and 9β-hydroxy derivatives (XLIII) and (XLIV) as set forth in the following reaction scheme of Flowsheet H, wherein $R_1$, $R_2$, $R_3$ and Z are as hereinabove defined.

FLOWSHEET H

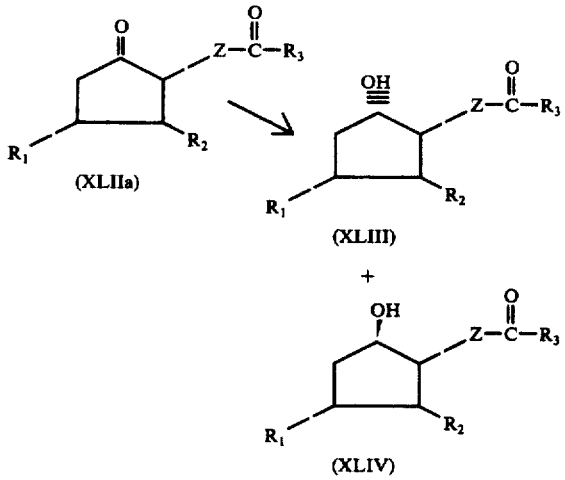

When the reaction is carried out with lithium perhydro-9b-boraphenylyl hydride [H. C. Brown and W. C. Dickason, Journ. Amer. Chem. Soc., 92,709 (1970)] or with lithium tri(sec-butyl)-borohydride [H. C. Brown and S. Krishnamerthy ibid. 94, 7159 (1972)], the product is at least predominantly the 9α-hydroxy derivative (XLIII), wherein the 9-hydroxy group is cis to the side-chain attached to $C_8$ and to the 11-oxy function. In accordance with accepted convention, an α-substituent at the 8-, 9-, 11- or 12-positions is behind the plane of the paper whereas a β-substituent at these positions is in front of the plane of the paper. This is usually represented by a - - - bond for an α-substituent, a — bond for a β-substituent, and a ~ bond which both are indicated. Thus, the 9-hydroxy derivatives may be variously represented as follows:

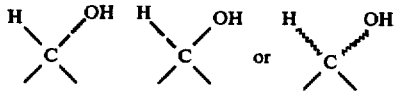

The preparation of the thia intermediates (XLVIII) and (IL), proceeds from the intermediate (XLV) (XIX in Flowsheet C) which after conversion to the tosylate intermediate (XLVI) and reaction with the sodium salt of ethyl mercaptoacetate furnishes intermediate (XLVII). Deblocking of (XLVII) with acetone-aqueous hydrochloric acid provides the keto-acid (XLVIII), which on re-esterification with ethanol gives the required 2-(ω-carbethoxy-3-thia-alkyl)cycloalk-2-en-1-ones (IL).

FLOWSHEET I

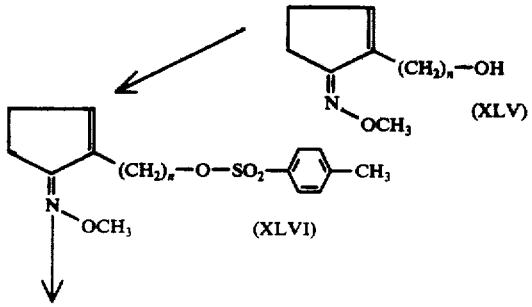

-continued

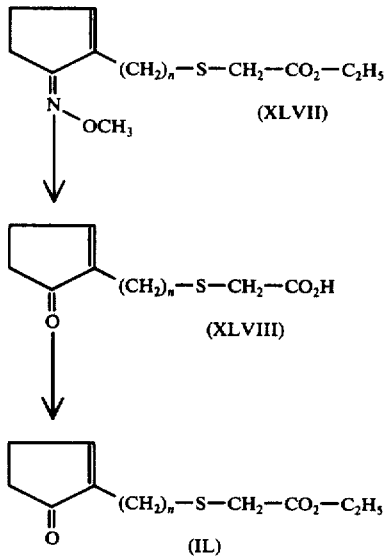

When the compounds of this invention are prepared from racemic starting compounds two racemates are obtained. In appropriate instances these racemates can be separated from each other by careful application of the usual chromatographic procedures. In the more difficult instances it may be necessary to apply high pressure liquid chromatography including recycling techniques. [See G. Fallick, American Laboratory, 19–27 (Aug., 1973) as well as references cited therein. Additional information concerning high speed liquid chromatography and the instruments necessary for its application is available from Waters Associate, Inc. Maple St., Milford, Mass.]

It is also possible to prepare the individual enantiomers via the conjugate addition procedure discussed above by starting with a resolved 4-oxycyclopentenone (see XXXVII) and a resolved β-chain precursor (see XXXIII or XXXIXb).

The 4-hydroxycyclopentenone racemates may be resolved into their component enantiomers (L) and (LI) by derivatizing the ketone function with a reagent having an optically active center. The resulting diastereoisomeric mixture can then be separated by fractional crystallization, or by chromatography, or by hidh speed liquid chromatography involving, if necessary, recycling techniques. Among the useful optically active ketone derivatizing reagents are 1-α-aminoxy-γ-methylpentanoic acid hydrochloride (to give LII), (R)2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (L) and (LI). A useful procedure for the resolution of a 4-hydroxycyclopentenone racemate via an oxime such as (LII) is described in the art [R. Pappo, P. Collins and C. Jung, Tetrahedron Letters, 973 (1973)].

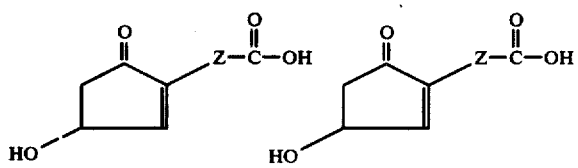

(L) (LI)

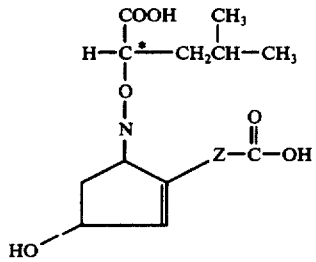

(LII)

An alternative procedure for the preparation of the 4(R)-hydroxycyclopentenone enantiomers such as (L) involves as a key stop the selective microbiological or chemical reduction of trione (LIII) to the 4(R)-hydroxycyclopentanedione (LIV). A wide variety of microorganisms are capable of accomplishing this asymmetric reduction, one of the most useful being Dipodascus unincleatus. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis(o-anisylcyclohexylmethylphosphine)rhodium (I) tetrafluoroborate in the presence of one equivalent of organic base, such as triethylamine.

Conversion of hydroxycyclopentanedione (LIV) to an enol ether or enol ester, (LV, E = alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° to −15° C. Reduction of (LV) with excess sodium bis(2-methoxyethoxy)aluminum hydride in a solvent such as tetrahydrofuran or toluene at low temperatures, such as −60° to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (LVI). The ester (LVI), after blocking the hydroxy function as described hereinabove, can be subjected to conjugate addition reactions also as described hereinabove. The conjugate addition product, after deblocking the 11- and 15-hydroxy groups, will then be a methyl ester which can be hydrolyzed to the corresponding carboxylic acid by enzymatic or microbiological procedures, for example with baker's yeast or by exposure to Rhizopus oryzae.

For a description of these procedures in the art see: C. J. Sih et al., Journ. Amer. Chem. Soc., 95 1676 (1973); J. B. Heather et al., Tetrahedron Letters, 2213 (1973); R. Pappo and P. W. Collins, Tetrahedron Letters, 2627 (1972) and R. Pappo, P. Collins and C. Jung, Ann. N.Y. Acad. Sci., 180, 64 (1971). For a descriptive of the baker's yeast procedure see C. J. Sih et al., Journ. Amer. Chem. Soc., 94 3643 (1972).

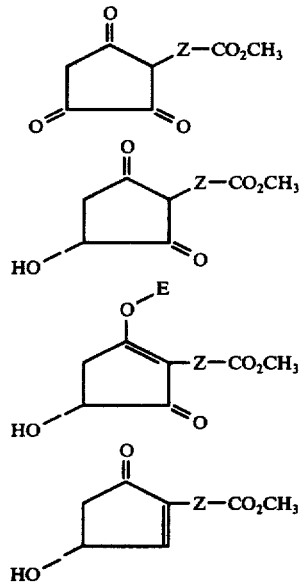

(LIII) (LIV) (LV) (LVI)

Procedures for the preparation of the requisite cyclopentanetriones (LII) are well-established in the art and generally involve the treatment of an ω-1 oxo long chain ester (LVII) with methyl or ethyl oxalate and a base such as sodium methoxide in methanol, followed by treatment with dilute hydrochloric acid in aqueous methanol to effect the dealkoxalylation of the intermediate (LXVIII). See J. Kutsube and M. Matsui, Agr. Biol. Chem., 33, 1078 (1969); P. Collins, C. J. Jung and R. Pappo, Israel Journal of Chemistry, 6, 839 (1968); R. Pappo, P. Collins and C. Jung, Ann. N.Y. Acad. Sci. 180, 64 (1971); C. J. Sih et al., Journ. Amer. Chem. Soc., 95, 1676 (1973) (see reference 7); and J. B. Heather et al., Tetrahedron Letters, 2313 (1973) for pertinent background literature.

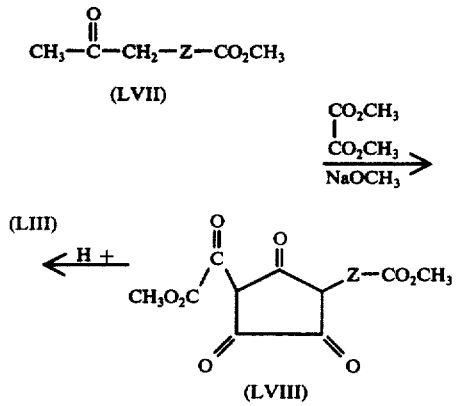

(LVII) (LIII) (LVIII)

The intermediate keto esters (LVII) may be prepared by a variety of methods known to the art. One useful procedure is outlined below and involves alkylation of ethyl acetoacetate sodium salt (LIX) in the usual manner with the appropriate side-chain precursor (LX, X=Cl, Br, I, preferably Br or I) followed by decarbethoxylation and reesterification, all in the usual manner.

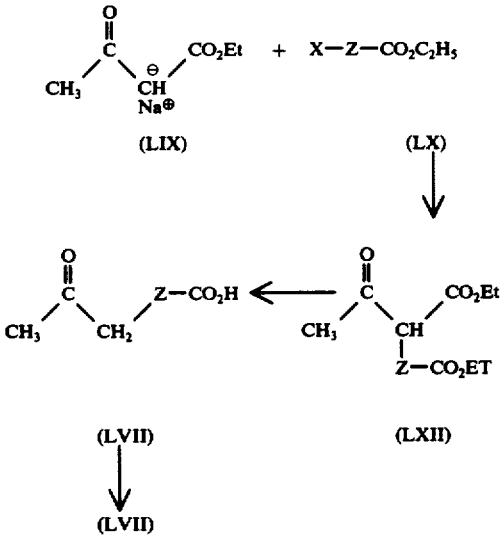

The side-chain precursors (LX) are commercially available where Z is $—(CH_2)_n—$, and can be prepared as described in Belgian Pat. No. 786,215 (granted and opened to inspection Jan. 15, 1973) where Z is

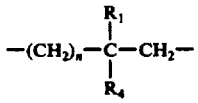

Where Z is

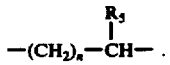

precursor (LX) can be prepared as indicated below by mono-tetrahydropyranylation of the diol (LXIII) to (LXIV), followed by mesylation, treatment of the resulting mesylate (LXVI) with the appropriate substituted sodio malonate to give (LXV), decarbethoxylation and reesterification to (LXVII), mesylation of the second hydroxy function to (LXIX) and displacement with lithium bromide (or iodide) to (LXXI). Alternatively, the ω-bromo alcohol (LXX) after blocking as the tetrahydropyranyl derivative (LXVIII), on treatment with the substitued sodio malonate provides (LXV).

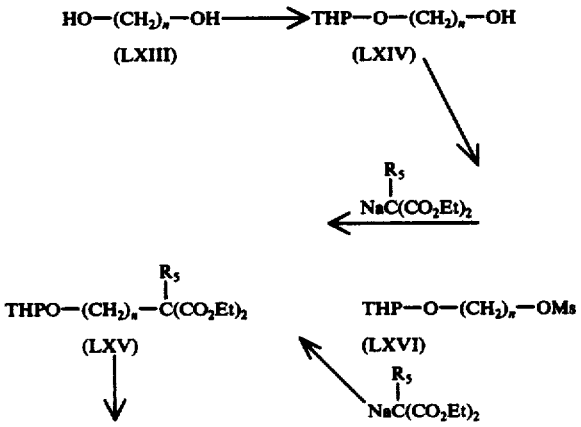

-continued

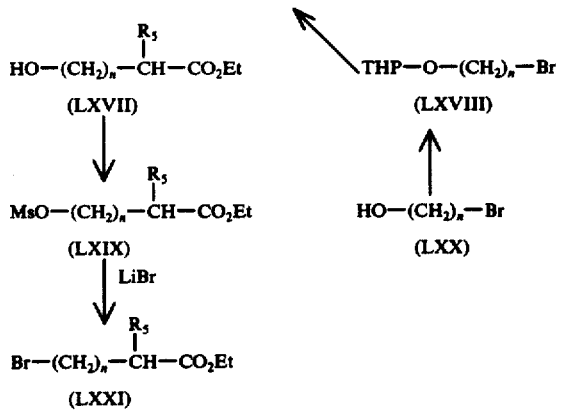

Those precursors wherein Z is $—(CH_2)_n—O—CH_2—$ can be prepared by the transformation shown directly below starting with the mono-tetrahydropyranyl derivative (LXIV). Thus, (LXIV) is converted to the lithium alcoholate by treatment with butyl lithium, the alcoholate is then O-alkylated with ethyl bromoacetate to provide (LXXII), which on de-tetrahydropyranylation, mesylation and reaction with lithium bromide gives the required (LXXV). (These and all the above-described transformation can be effected in the usual manner, well-established in the art; pertinent examples for most of the reactions can be found in the above-cited Belgian Pat. No. 786,215.)

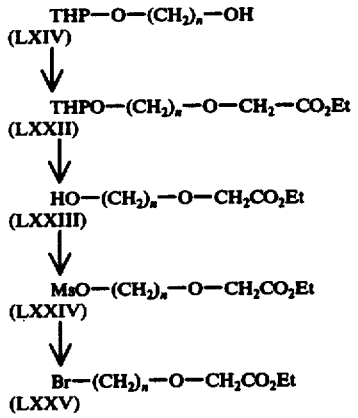

It is also possible to resolve the 4-hydroxycyclopentenone racemate (LXXVI) by microbiological means. Thus, treatment of the 4-O-alkanoyl or aroyl derivatives (LXXVII), $R_{12}$ = aryl (or alkyl) of racemate (LXXVI) (preferably the 4-O-acetyl and 4-O-propionyl derivatives) with an appropriate microorganism preferably a Saccharomyces species, e.g. 1375–143, affords preferential de-O-acylation of the 4(R)-enantiomer to give (LXXVIII), which is then separated from the unreacted 4(S)-O-acyl enantiomer (LXXIX) by chromatographic procedures. After separation, mild hydrolysis of the 4(S) derivative (LXXIX) provides the 4(S)-hydroxycyclopentenone (LXXX) [See N.J. Marsheck and M. Miyano, Biochimica et Biophysica Acta, 316, 363 (1973) for related examples.]

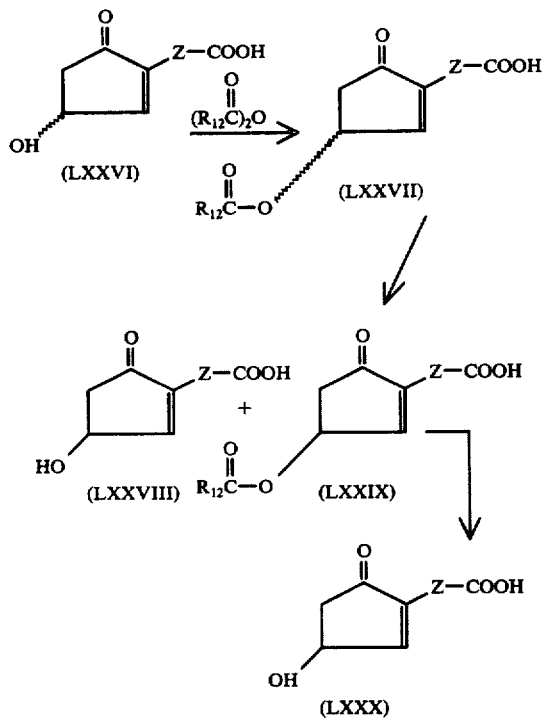

It is also possible to prepare the individual 4-hydroxycyclopentenones (LXXVIII) and (LXXX) directly by selective microbial hydroxylations of the corresponding 4-unsubstituted cyclopentenone (LXXXI). For example, with Aspergillus niger ATCC 9142; a selective 4(R)-hydroxylation of (LXXXI) [Z = $(CH_2)_6$] has been reported; for a literature example, see S. Kurozumi, T. Tora and S. Ishimoto Tetrahedron Letters, 4959 (1973). Other organisms can also accomplish this hydroxylation.

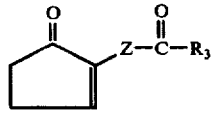
(LXXXI)

An alternate resolution procedure involves derivatization of the alcohol function of the racemic hydroxycyclopentenone to give ester-acid derivatives such as (LXXXII) wherein $R''_3$ is hydrogen or an alkoxy group, n' is zero or two and Z is as hereinabove defined.

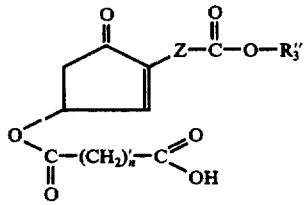
(LXXXII)

Such derivatives may be obtained from the corresponding free hydroxycyclopentenone by treatment in the usual manner with oxalyl chloride, succinyl chloride, succinic anhydride and the like. Treatment of the resulting acid or diacid ($D''_3$ = hydrogen) with optically active amines e.g., 1-(−)-α-methylbenzylamine, d-(+)-α-methylbenzylamine, brucine, dehydroabietylamine, strychnine, quinine, cinchonine, quinidine, ephedrine, (+)-α-amino-1-butanol and the like, and fractional recrystallization of the resulting diasteromeric mixtures, followed by cleavage of the 4-oxy ester function in each of the individually isolated diastereomers provides the individual 4(S)- and 4(R)-hydroxycyclopentenone enantiomers (L) and (LI) or their respective esters. Cleavage of the oxalate acid ester (LXXXII, n = 0) can be accomplished by treatment with lead tetraacetate in pyridine solution. For an example of a similar use of oxalate acid-esters see J. G. Molotkovsky and L. D. Bergelson, Tetrahedron Letters 4791 (No. 50, 1971); for an example of the use of the succinate acid-ester see B. Goffinet, Ger. Offen. No. 2,263,880; Chem. Abstracts, 79, $78215_z$ (1973).

The racemic β-chain precursors can be resolved at either the acetylenic alcohol stage (XXXIII, Flowsheet E) or the trans-vinyl iodide state (XXXIXb, Flowsheet F) by a variety of methods well-known in the art. These methods will be illustrated below with the acetylenic alcohol (LXXXIII), but they apply equally well to the trans-vinyl iodide (LXXXIV). Furthermore, the resolved acetylenic alcohols corresponding to (LXXXIII) can be converted to the trans-vinyl iodides corresponding to (LXXXIV) or its derivatives as described hereinabove without racemization [see for an example, A. F. Kluge, K. G. Untch and J. H. Fried, Journ. Amer. Chem. Soc., 94, 7827 (1972)].

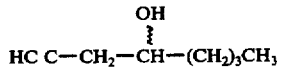
(LXXXIII)

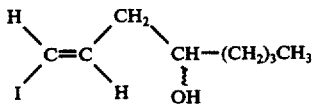
(LXXXIV)

Racemates (LXXXIII) or (LXXXIV) can be resolved by reverse phase and absorption chromatography on an optically active support system or by selective transformation of one isomer by microbiological or enzymatic procedures.

A more generally applicable procedure involves conversion of the racemic alcohol to a mixture of diastereomers by derivatization of the hydroxy function with an optically active reagent, followed by separation of the diastereomers by fractional crystallization or chromatographic procedures, as discussed hereinabove. Regeneration of the alcohol function from the individual diasteromer then provides the individual enantiomeric alcohols, e.g. (LXXXV) and (LXXXVI).

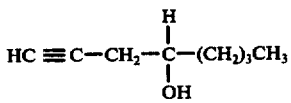
(LXXXV)

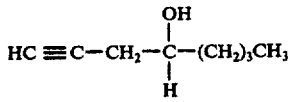
(LXXXVI)

Useful derivatives for resolution purposes include the salts of the phthalate half acid ester (LXXVII) with an optically active amine (e.g., 1-(−)-α-methylbenzylamine, d-(+)-α-methylbenzylamine, brucine, dehydroabietylamine, strychnine, quinine, cinchonine, cinchonidine, quinidine, ephedrine, deoxyephedrine amphetamine, (+)-2-amino-1-butanol, (−)-2-amino-1-butanol and the like).

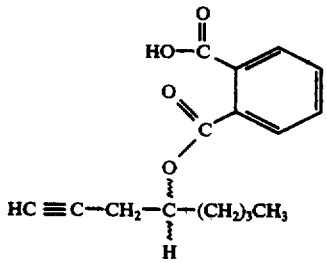

(LXXXVII)

For the resolution in the art of the related 3-hydroxy-1-octyne by this procedure see J. Fried et al., Annals of the N.Y. Acad. of Sci., 180, 38 (1971), and of the related 1-iodo-trans-1-octen-3-ol see A. F. Kluge, K. G. Untch and J. H. Fried, Jour. Amer. Chem. Soc., 94, 7827 (1972).

Other useful derivatives are the diastereomeric carbamates (LXXXVIII) obtained by treatment of racemate (LXXXIII) with an optically active isocyanate (e.g., (+)-1-phenylethylisocyanate and (−)-1-phenylethylisocyanate).

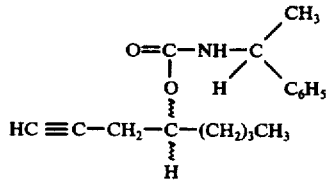

(LXXXVIII)

Various esters of racemate (LXXXIII) with optically active acids are also useful for resolution purposes. Among the optically active acids which can be used in this connection are ω-camphoric acid, methoxyacetic acid, 3α-acetoxy-$\Delta^5$-etianic acid, 3α-acetoxy-5,16-etiadienoic acid, (−)-α-methoxy-α-trifluoromethylphenylacetic acid (see LXXXIX), (+)-α-methoxy-α-trifluoromethylphenylacetic acid, and the like.

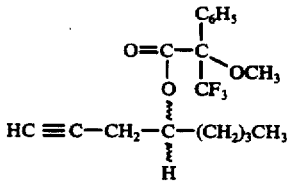

(LXXXIX)

The resolution of the related 1-octyne-3-ol with 3β-acetoxy-$\Delta^5$-etianic acid and 3β-acetoxy-5,16-etiadienoic acid has been described in the art [see R. Pappo, P. Collins, and C. Jung, Annals of the N.Y. Acad. of Sci., 180, 64 (1971)].

The preparation of the enantiomeric acetylenic alcohols or 4-hydroxy-trans-vinyl iodides can also be accomplished by microbial techniques, involving a selective deesterification of 4-O-alkanoyl or aroyl derivatives (XL) followed by chromatographic separation to the individual enantiomers and hydrolysis of the non de-esterified ester. Useful microorganisms for this purpose are Rhizopus arrhizus and Rhizopus nigricans (ATCC 6227b).

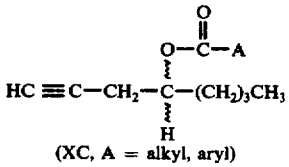

(XC, A = alkyl, aryl)

Alternatively, it is possible to effect selective microbial reduction of the corresponding 4-keto derivatives (XCI) and (XCII) to a single enantiomer, useful microorganisms for this purpose are Penicillium decumbens and Aspergillus ustus. Ketones (XCI) and (XCII) are readily obtainable by oxidation under mild conditions of the corresponding alcohols. For pertinent literature examples see J. B. Heather et al., Tetrahedron Letters, 2313 (1973). It is also possible to effect optically selective reduction of ketones.

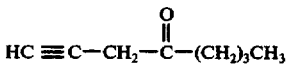

(XCI)

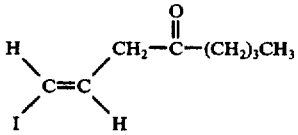

(XCII)

(XCI) or (XCII) by the use of an optically active reducing agent such as tri(+S-2-methylbutyl)aluminum etherate, lithium aluminum hydride-3-O-benzyl-1,2-O-cyclohexylidene-α-glucofuranose complex, and lithium hydrodipinan-3α-ylborate. For pertinent references to this procedure see R. A. Kretchmer, Journ. Org. Chem. 37, 801 (1972); S. A. Landor et al., Journ. Chem. Soc. (C) 1822, 2280 (1966), ibid. 197 (1967); M. F. Grundon et al., ibid., 2557 (1971); and J. D. Morrison and H. S. Mosher, "Assymetric Organic Reactions", pp. 160–218, Prentice-Hall, Englewood Cliffs, N.J. (1971).

It is to be noted that use of only one resolved precursor, either the β-chain or the 4-hydroxycyclopentenone, in the conjugate addition process will lead to the formation of two diastereomers, which, at least in appropriate instances, can then be separated by chromatographic and other procedures (as described above for the corresponding racemate) into the individual component enantiomers.

For the particular case of the preparation of optically active acetylenic alcohols wherein the hydroxy group occupies the 4-position of the chain, advantage may be taken of a well-known and general microbiological reduction process, depicted in Flowsheet J. According to this process, a 1-hydroxy-2-oxoalkene (XCV) is added to the fermenting mixture obtained from sucrose and baker's yeast (see P. A. Levene and A. Walti, Org. Synthesis, Coll. Vol. II, p. 545 and J. P. Anette and N. Spassky, Bull. Soc. Chim. France, 1972, 4217, for appropriate examples). The reductase of this system stereospecifically provides the (R)-1,2 -dihydroxyalkanes (XCVII). The glycol thus prepared is converted stereospecifically to the (R)-1,2-epoxyalkane (XCVI) by one of several procedures known in the art (see B. T. Golding et al., Journal. Chim. Soc. Perkin I, 1973, 1214 and M. S. Newman and C. M. Chen, Journ. Amer. Chem. Soc. 95, 278 (1973), for appropriate examples). The stereospecific conversion of this epoxide to the (R)-4-hydroxy-1-alkyne (XCVIII) may be accomplished by displacement with lithium acetylide-ethylenediamine complex in dimethyl sulfoxide (see E. Casadevall, et al., Compt. Rind. C, 265, 839 for pertinent literature).

The (R)-1,2-dihydroxyalkane (XCVII) obtained from the yeast fermentation may also be used for the preparation of the (S)-4-hydroxy-1-alkyne (CII). Preferential triphenylmethylation of the primary alcohol group provides the monoether (IC) (see L. J. Stegerhoek and P. E. Verkade, Rec. Trav. Chim. 74, 143 (1955) for pertinent literature). The remaining alcohol group is esterified with a sulfonyl halide such p-toluenesulfonyl chloride to provide the sulfonate ester (CI). Catalytic hydrogenolysis of the trityl group followed by treatment of the resulting free primary alcohol with a strong base, e.g. potassium hydroxide in methyl alcohol, provides the epoxide of the opposite configuration, a (S)-1,2-epoxyalkane (CIII) (see J. Fried, et al. Journ. Amer. Chem. Soc., 94, 4343 (1972) and J. W. Cornforth et al. Journ. Chem. Soc., 1959, 112, for pertinent literature). This substance is reacted with lithium acetylide-ethylenediamine complex to provide the (S)-4-hydroxy-1alkyne (CII).

Alternatively the (R)-4-hydroxy-1-alkyne (XCVIII) may be converted to a sulfonate ester (C), and the sulfonate function of the latter may be displaced by hydroxy to provide the (S)-4-hydroxy-1-alkyne (CII) (see R. Baker, et al., Journ. Chem. Soc. C. 1969, 1605 for pertinent literature).

The (R)- or (S)-4-hydroxy-1-alkynes are converted via either the vinyl iodide (XCIII) or the alane (XCIV) to 16-hydroxyprostaglandins of the (16R)- and (16S)-series respectively by the procedure outlined hereinabove.

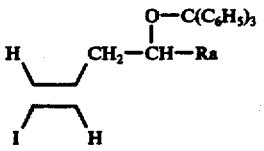

(XCIII)

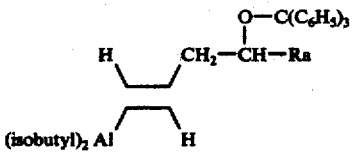

(XCIV)

The starting 1-hydroxy-2-oxoalkanes for this procedure may be prepared in a variety of ways well-known to the literature [see P. A. Levene and M. L. Maller, Journ. Biol. Chem., 79, 475 (1928) and I. Forgo and J. Buchi, Pharm. Acta Helv., 45, 227 (1970)]. In Flowsheet J which follows Ra is an alkyl group.

FLOWSHEET J

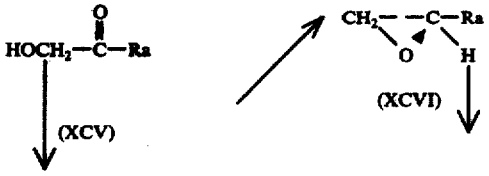

-continued

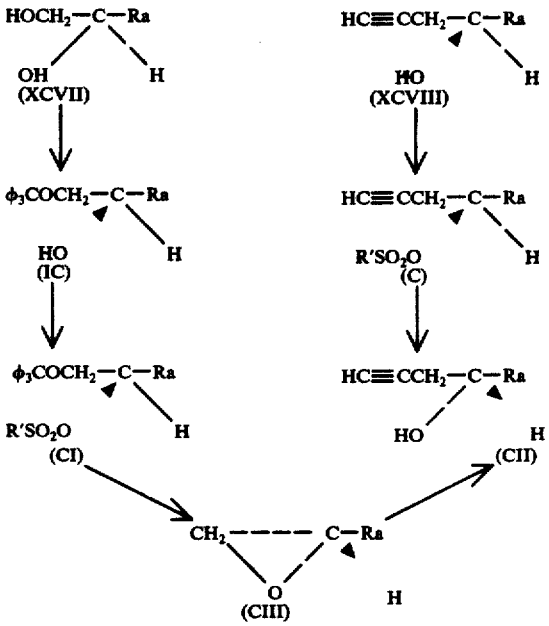

Utilization of only a resolved $\beta$-chain or only a resolved hydroxycyclopentenone gives a mixture of diastereomers, which depending upon the circumstances, may or may not be separable by the usual procedures of crystallization and chromatography. If necessary, high speed liquid chromatography, including recycling techniques, can be applied. Additional procedures, well-understood in the literature, for effecting the resolution of diasteromeric prostenoic acids and esters (or of two racemates) of this invention are described below.

In these procedures 9-oxo-11$\alpha$,16(S)-dihydroxy-13-trans-prostenoic acid and its 9$\alpha$-hydroxy derivative are used for illustrative purposes, it being understood, however, that the procedures are general and have applicability to the other products of this invention, particularly to those derivatives wherein the 11-position is not substituted with an oxy function.

Conversion of a 9$\alpha$-hydroxy diasteromeric mixture (the component diastereomers are illustrated by CIV and CV below) wherein the $C_{11}$ and $C_{16}$ hydroxy functions have been preferentially blocked by tetrahydropyranyl or trialkylsilyl groups, to the corresponding phthalate half acid-ester, deblocking the $C_{11}$ and $C_{16}$ hydroxy functions and conversion of the diacid (e.g., CVI) to a bis salt (e.g., CVII) with an optically active amine (e.g., 1-(−)-$\alpha$-methylbenzylamine, D-(+)-$\alpha$-methylbenzylamine, brucine, dehydroaebietylamine, strychnine, quinine, cinchonine, cinchonindine, quindine, ephedrine, deoxyepedrine, amphetamine, (+)-2-amino-1-butanol, (−)-2-amino-1-butanol and the like). The resulting diastereomers are then separated by fractional crystallization and the individual components are then converted by acidification and saponification to the individual optically active parent 9$\alpha$-hydroxy diastereomers (CIV) and (CV), oxidation of which, after preferential blocking of the $C_{11}$ and $C_{16}$ hydroxy functions with tetrahydropyranyl or trialkylsilyl groups, provides the corresponding individual 9-oxo diastereomers (CVIII) and (CIX). (For an appropriate literature procedure see E. W. Yankee, C. H. Lin and J. Fried, Journ. Chem. Soc., 1972, 1120).

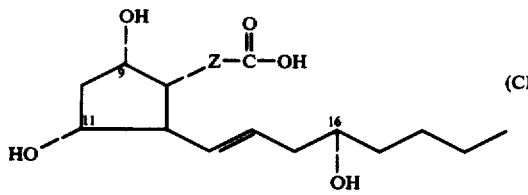

(CIV)

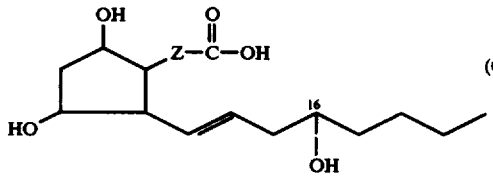

(CV)

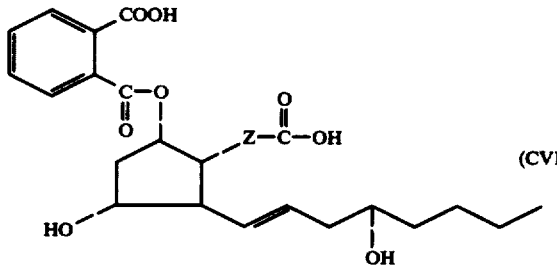

(CVI)

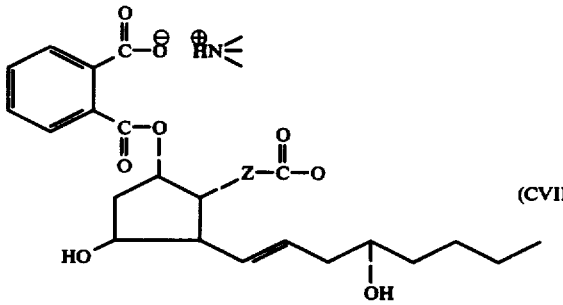

(CVII)

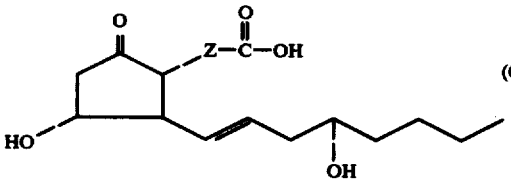

(CVIII)

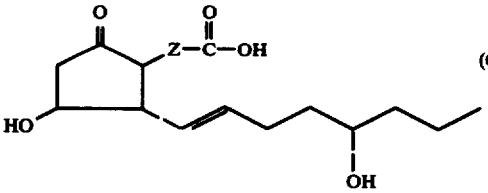

(CIX)

Another procedure involves conversion of the 9α-hydroxy diastereomeric mixtures (as the prostenoic acid ester and with the $C_{11}$ and $C_{16}$ alcohol functions preferentially blocked as tetrahydropyranyl or trialkylsilyl ethers) to the diastereomeric carbamates with an optically active isocyanate, e.g., (+)-1-phenylethylisocyanate or (−)-1-phenylethylisocyanate, followed by deblocking. Separation of the diastereomers, for example (CX) and (CXI) can be accomplished by fractional crystallization or by the usual chromatographic procedures, or if necessary by high speed liquid chromatography involving, if necessary, recycling techniques. Base-treatment of the individual diastereomeric carbamates affords the individual diasteromeric alcohols, for example (CIV) and (CV).

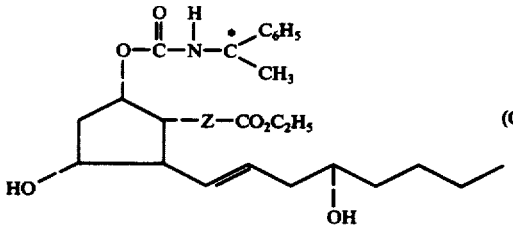

(CX)

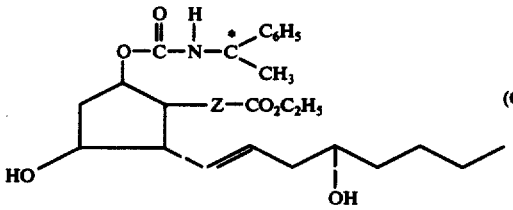

(CXI)

It is also possible to effect resolution of the 9α-hydroxy derivative, preferably as the prostenoate esters, by esterification of the 9α-hydroxy function (prior preferential blocking of $C_{11}$ and $C_{16}$ hydroxy functions as tetrahydropyranyl or trialkylsilyl ethers) with an optically active acid, via its acid chloride followed by deblocking the $C_{11}$ and $C_{16}$ alcohol groups. Suitable optically active acids include ω-camphoric acid, methoxyacetic acid, 3α-acetoxy-$\Delta^5$-etianic acid, (−)-α-methoxy-α-trifluoromethylphenylacetic acid and (+)-α-methoxy-α-trifluoromethylphenylacetic acid, and the like. The resulting diastereomeric esters, for example (CXII) and (CXIII), are then separated by fractional crystallization or by chromatographic techniques including, if necessary, the use of high speed liquid chromatography. Saponification of the individual diastereomers then provides the individual 9α-hydroxy-prostenoic acid diastereomers (CIV) and (CV).

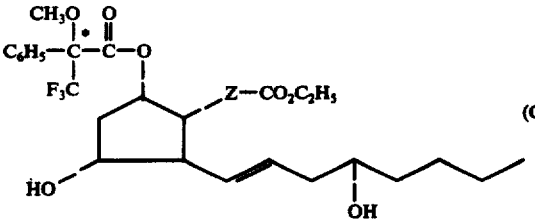

(CXII)

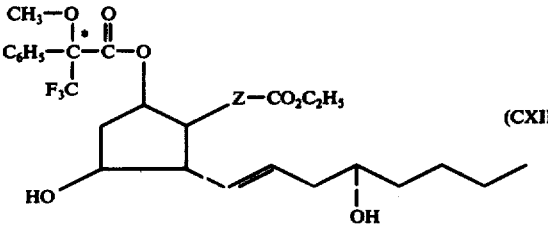

(CXIII)

Another resolution procedure, less useful than the methods described above based on the 9α-hydroxy derivative but particularly applicable to 11-unsubstituted compounds of this invention, involves derivatization of the keto function of the diastereomeric 9-oxo-prostenoic acid or ester illustrated by (CVIII and CIX) with the usual type of ketone derivatizing agents bearing an optically active center. The resulting mixture of diastereomeric derivatives can then be separated by fractional crystallization or by chromatography or, if necessary, by high speed liquid chromatography. The individual diastereomeric keto derivatives, for example (CXIV) and (CXV), are then convertable to the individual 9-oxo diastereomers (CVIII) and (CIX) by any of the usual cleavage techniques, provided that they are sufficiently mild so as not to disturb the sensitive 11-hydroxy-9-keto system. (This latter point is not a problem with 11-unsubstituted derivatives.) Ketone reduction of the 9-oxo-enantiomer as [descried] *described* hereinabove then provides the corresponding 9α-hydroxy or 9β-hydroxy diastereomer (CIV) or (CV). Among the optically active reagents useful for ketone derivatization are 1-α-aminoxy-α-methylpentanoic acid hydrochloride [E. Testa et al., Helv. Chemica Acta, 47 (3), 766 (1973)], methylhydrazine, and 4-α-methylbenzylsemicarbazide. A useful procedure for the cleavage of oximes such as (CXIV) and (CXV) involves treatment of the oxime at about 60° C. for about 4 hours in 1:2 aqueous-tetrahydrofuran buffered with ammonium acetate and containing titanium trichloride.

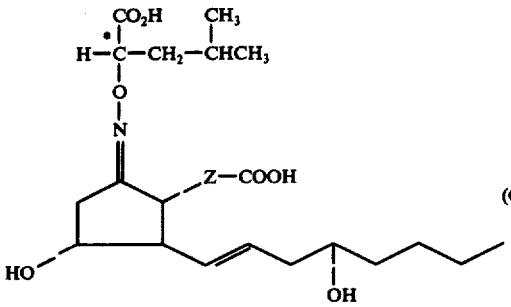

(CXIV)

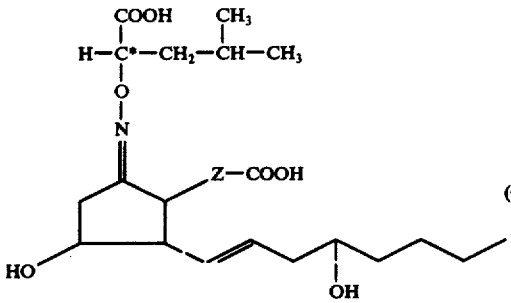

(CXV)

Other useful ketone derivatizing agents are optically active 1,2-glycols, e.g., D(−)-2,3-butanediol, or 1,2-dithiols, e.g., L(+)-2,3-butanedithiol. These are used to convert the 9-oxo derivative to 9,9-alkylenedioxa or 9,9-alkylenedithia derivatives, separation of diastereomers by chromatographic procedures followed by regeneration of the individual 9-oxo diastereomer by ketal cleavage all by procedures well-known in the art. Both ketalization and deketalization would have to be accomplished by procedures which would not disrupt the 11-oxo-9-keto system, which of course, is not a problem in the 11-unsubstituted series.

An alternative procedure for the conversion of substituted 1-alkyne (CXVI) to product (CXX) (formulae XXXIII and XXXVIII respectively of Flowsheet E) proceeds via vinyl lithium reagent (CXVII) (formula XXXIXc of Flowsheet F).

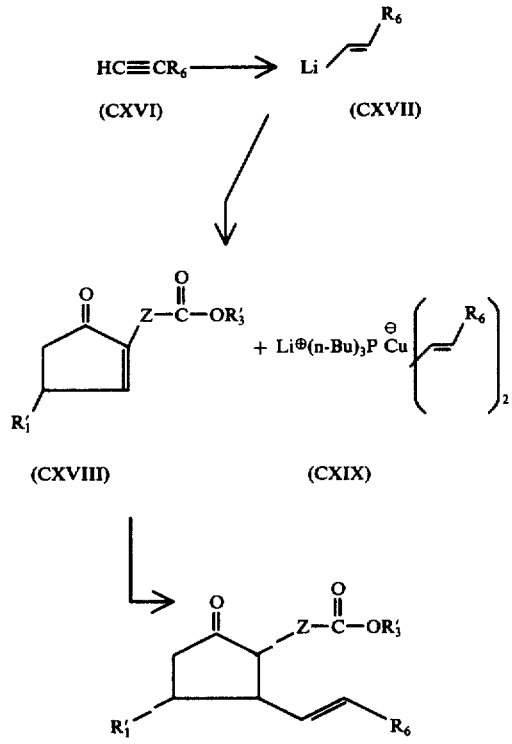

(CXX)

In this procedure (CXVII) is reacted with the complex of cuprous iodide-tri-n-butylphosphine is an ether solvent at very low temperatures, e.g., −78° C., to provide a divinyl lithio cuprate species (CXIX). This reagent (CXIX) is reacted with cyclopentenone (CXVIII) (XXXVII of Flowsheet E) in ether-hydrocarbon solvent at −78° C. to 0° C. to provide product (CXX), after workup with aqueous ammonium chloride.

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various non-sterodial antiinflammatory agents, e.g. indomethacin, aspirin, and phenylbutazone, bronchodilators, antimicrobial agents, anticonvulsants, abortifacients, agents for the induction of labor, agents for the induction of menses, fertility-controlling agents, central nervous system regulatory agents, salt and water-retention regulatory agents, diuretics, fat metabolic regulatory agents and as serum-cholesterol lowering agents. Certain of the novel compounds of this invention possess utility as intermediates for the preparation of other of the novel compounds of this invention.

Anti-ulcerogenic Effect of Indomethacin

The compounds of this invention also provide protection against the ulcerogenic properties of indomethacin. This assay was carried out in the following manner.

Rats were starved for 48 hours (water was given ad libitum). Indomethacin (20 mg./kg. of body weight) was administered by the subcutaneous route and one-half the dose of the test compound was administered by gavage at the same time. After 3 hours, the second half of the test compound was administered also by gavage. Five hours after the administration of indomethacin the animals were decapitated and the stomachs removed.

The stomachs were washed with distilled water, blotted on gauze, cut along the larger curvature, and the contents rinsed with distilled water. The stomachs were spread out, pinned on a cork and visualized under magnifying glass for ulcers. The criteria for scoring of [ulers] *ulcers* was as previously reported. [Abdel-Galil et al. Brit. J. Pharmac. Chemotherapy 33:1-14 (1968)].

| | SCORE |
|---|---|
| 0- | Normal Stomach |
| 1- | Petechial hemorrhage or pin point ulcers |
| 2- | 1 or 2 small ulcers |
| 3- | Many ulcers, a few large |
| 4- | Many ulcers, mainly large |

A difference of at least 0.7 unit between the scores for control animals (treated with indomethacin but not test compound) and animals treated with indomethacin and test compound is considered indicative of activity for the test compound. (Control animals treated with neither indomethacin nor test compound give scores of about 0.5–0.8.) The results obtained in this assay with typical compounds of the present invention are set forth in Table I below.

TABLE I

| Compound | Total oral dose: mg./kg of body weight | Score treated | Score control |
|---|---|---|---|
| 9-oxo-16-hydroxy-13-trans-prostenoic acid | 50 | 1.2 | 2.3 |
| 9-oxo-16-hydroxy-prostenoic acid | 50 | 1.3 | 2.3 |
| 9-oxo-11α,16-dihydroxy-13-trans-prostenoic acid | 12.5 | 1.0 | 3.0 |
| | 4.4 | 1.0 | 3.0 |
| | 1.56 | 1.0 | 2.5 |
| | 0.78 | 1.5 | 3.0 |
| | 0.39 | 2.0 | 3.0 |
| | 0.18 | 2.5 | 3.0 |
| 9-oxo-11α,17-dihydroxy-13-trans-prostenoic acid | 25 | 1.3 | 2.7 |

The novel compounds of the present invention are also effective inhibitors of gastric acid secretion and of ulcer development in experimental animals, and thus are potentially valuable as agents for the control of gastric acid secretion and of gastric erosion and as anti-ulcer agents. Gastric acid secretion inhibitory action is usually measure by the "Shay rat" procedure[1,2] with some modifications as follows.

1. Shay et al., Gastroenterology, 5, 43 (1945).
2. Shay et al., Gastroenterology, 26, 906 (1954).

The rats (male, CFE strain) were starved for 48 hours (water was given ad libitum) to permit evacuation of stomach contents. On the morning of the experiment, under ether anesthesia, the abdominal region was shaved and a midline incision (1–1½ inches) was made with a scapel. With the help of a closed curved hemostate the duodenum was picked up. Upon getting the duodenum into view, fingers were used to pull the stomach through the opening, the stomach was then gently manipulated with fingers to rid the stomach of air and residual matter which were pushed through the pylorus. Two-5 inch sutures were drawn under the pyloric-duodenal puncture. A ligature, at the juncture, was formed with one of the threads. The second ligature was also formed but not tightened.

The test compound and the vehicle, usually 1 ml./100 g. body weight, were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips. (Occasionally, instead of an intraduodenal injection, animals were dosed by the oral or subcutaneous route. In the latter case, dosing was done 30 to 60 minutes before the operation.)

Three hours later, the rats were decapitated and exanguinated, taking care that blood did not drain into the esophagus. The abdominal cavity was exposed by cutting with scissors and the esophagus close to the stomach was clamped off with a hemostat, the stomach was removed by cutting above the hemostat (the [esphagus] *esophagus* was cut) and between the two sutures. Extraneous [tisue] *tissue* was removed, the stomach washed with saline and blotted on gauze. A slit was carefully made in the stomach which was held over a funnel and the contents were collected in a centrifuge tube. The stomach was further cut along the outside edge and turned inside out. Two ml. $H_2O$ were used to wash the stomach contents into the respective centrifuged tube. The combined stomach contents and wash were then centrifuged out for 10 min. in the International Size 2 Centrifuge (setting at 30). The supernatant was collected, volume measured and recorded, 2 drops of a phenylphthalein indicator (1% in 95% ethanol) were added and the solution was titrated with 0.02N NaOH (or with 0.04N NaOH when large volumes of stomach contents were encountered to pH 8.4 (because of usual coloring of the stomach contents, phenolphthalein was only used to permit visual indication that the end point was near) and the amount of acid present was calculated.

Compounds inducing inhibition of gastric acid secretion of 20% or more were considered active. In a representative operation, and merely by way of illustration, the results obtained with this assay with typical compounds of the present invention are given in Table II below.

Table II

| Compound | Intraduodenal dose, mg./kg of body weight | Percent Inhibition |
|---|---|---|
| 9-oxo-16-hydroxy-13-trans-prostenoic acid | 50 | 67 |
| 9-oxo-16-hydroxy prostanoic acid | 50 | 58 |
| 9-oxo-20-hydroxy 13-trans-prostenoic acid | 100 | 56 |
| 9-oxo-18/19-hydroxy-13-trans-prostenoic acid | 100 | 28 |
| 9-oxo-18-hydroxy-19,20-dinor-13-trans-prostenoic acid | 50 | 21 |
| Ethyl 9-oxo-18-hydroxy-19,20-dinor-13-trans-prostenoate | 100 | 49 |
| 9-oxo-11α,16-dihydroxy-13-trans-prostenoic acid | 1.6* | 79 |
| | 0.8* | 53 |
| | 0.4* | 27 |
| 9-oxo-11α,17-dihydroxy-13-trans-prostenoic acid | 50 | 73 |
| 9-oxo-20-hydroxy-10,13-trans-prostadienoic acid | 50 | 91 |

Bronchodilator activity was determined in guinea pigs against bronchospasms elicited by intravenous injections of 5-hydroxytryptamine, histamine or acetylcholine by the Konzett procedure, [See J. Lulling, P.

Lievens, F. El Sayed and J. Prignot, Arzneimittel-Forschung, 18, 995 (1968).]

In the Table which follows bronchodilator activity for representative compounds of this invention against one or more of the three spasmogenic agents is expressed as an $ED_{50}$ determined from the results obtained with three logarithemic cumulative intravenous dose.

TABLE III

Bronchodilator Activity (Konzett Assays)

| Compound | $ED_{50}$ mg./kg. Spasmorgenic Agent 5-hydroxy--tryptamine | histamine | choline |
|---|---|---|---|
| 9-oxo-20-hydroxy-13-trans-prostenoic acid | $117 \times 10^{-3}$ | $30 \times 10^{-3}$ | 2.16 |
| 9-oxo-18-hydroxy-19,20-dinor-13-trans-prostenoic acid | 2.85 | 2.22 | 10.0 |
| 9-oxo-16-hydroxy-13-trans-prostenoic acid | $277 \times 10^{-a}$ | $34.6 \times 10^{-3}$ | $455 \times 10^{-3}$ |
| 9-oxo-16-hydroxy-prostanoic acid | $92.7 \times 10^{-3}$ | $477 \times 10^{-a}$ | 1.13 |
| 9-oxo-18/19-hydroxy-13-trans-prostenoic acid | 1.19 | 1.04 | |
| 9-oxo-11α,16-dihydroxy-13-trans-prostenoic acid | $.607 \times 10^{-3}$ | $166 \times 10^{-3}$ | $.420 \times 10^{-3}$ |
| 9-oxo-11α,17-dihydroxy-13-trans-prostenoic acid | 0.235 | 0.45 | 0.518 |
| 9-oxo-11α,20-dihydroxy-13-trans-prostenoic acid | 0.377 | 0.077 | 2.34 |
| 9-oxo-20-hydroxy-10,13-trans-prostadienoic acid | 1.32 | 2.28 | |

This invention will be described in greater detail in conjunction with the following specific examples.

EXAMPLE 1

Preparation of 2-carbalkoxy(methyl/ethyl)-2-(4-carbethoxybutyl)cyclopentan-1-one To a stirred solution of the sodium cyclopentanone carboxylate enolate in dimethoxyethane, prepared from 187 g. (1.248 moles) of 2-cyclopentanone carboxylate (mixed methyl and ethyl esters), 52.4 g. (1.248 moles) sodium hydride (57.2% in mineral oil) and 1.6 l. of dimethoxyethane, is added dropwise 309 g. (1.212 moles) of ethyl 5-iodovalerate. The reaction mixture is stirred and heated at reflux for 18 hours. The mixture is cooled and filtered. The solvent is removed from the filtrate by evaporation and the residue is poured into dilute hydrochloric acid and extracted with ether. The combined extracts are washed with water and saline, dried over magnesium sulfate and evaporated to give an oil. The oil is distilled under reduced pressure to give 274 g. of a light yellow oil, b.p. 140°–143° C. (0.17 mm).

EXAMPLE 2

Preparation of 2-(4-carboxybutyl)cyclopentan-1-one

A stirred mixture of 274 g. of 2-carbalkoxy(mixed methyl and ethyl esters)-2-(4-carbethoxybutyl)cyclopentan-1-one (Example 1), 600 ml. of 20% hydrochloric acid and 325 ml. of acetic acid is heated at reflux for 20 hours. Solution occurs in approximately one-half hour. The solution is cooled and diluted with water and extracted with ether. The combined extracts are washed with [salline] *saline* and dried over magnesium sulfate and evaporated. The residue is evaporated twice with toluene to give 144 g. of an oil.

EXAMPLE 3

Preparation of 2-(4-carbethoxybutyl)cyclopentan-1-one

A stirred solution of 124 g. (0.673 mole) of 2-(4-carboxybutyl)cyclopentan-1-one (Example 2), 800 ml. of ethanol and 1 g. of p-toluenesulfonic acid monohydrate is heated at reflux for 18 hours. The solvent is evaporated and the residue is dissolved in ether. The ether solution is washed with saline, dilute sodium bicarbonate solution and again with saline, dried over magnesium sulfate and evaporated. The oil is distilled under reduced pressure to give 149 g. of a colorless oil, b.p. 106°–109° C. (0.23 mm).

EXAMPLE 4

Preparation of 2-carbalkoxy(methyl/ethyl)-2-(3-carbethoxypropyl)cyclopentan-1-one In the manner described in Example 1, treatment of 2-cyclopentanone carboxylate (mixed methyl and ethyl esters) with sodium hydride in dimethoxyethane followed by ethyl 4-iodobutyrate gives a yellow oil, b.p. 136°–137° C. (0.16 mm).

EXAMPLE 5

Preparation of 2-(3-carboxypropyl)cyclopentan-1-one

In the manner described in Example 2, treatment of 2-carbalkoxy(mixed methyl and ethyl esters)-2-(3-carbethoxypropyl)cyclopentan-1-one (Example 4) with a 20% hydrochloric acid and acetic acid mixture gives a yellow oil.

EXAMPLE 6

Preparation of 2-(3-carbethoxypropyl)cyclopentan-1-one

In the manner described in Example 3, treatment of 2-(3-carboxypropyl)cyclopentan-1-one (Example 5)

with p-toluenesulfonic acid monohydrate in ethanol gives a colorless oil, b.p. 93° C. (0.10 mm).

EXAMPLE 7

Preparation of ethyl and methyl 2-(6-carbethoxyhexyl)-1-cyclopentanon-2-carboxylate In the manner described in Example 1, ethyl and methyl 2-cyclopentanone carboxylate is reacted with ethyl 7-bromoheptanoate to furnish the subject product, b.p. 147° C. (0.09 mm).

EXAMPLE 8

Preparation of 2-(6-carboxyhexyl)cyclopentan-1-one

In the manner described in Example 2, ethyl and methyl 2-(6-carbethoxyhexyl)-1-cyclopentanone-2-carboxylate (Example 7) is hydrolyzed to furnish the subject product, b.p. 143° C. (0.05 mm).

EXAMPLE 9

Preparation of 2-(6-carbethoxyhexyl)cyclopentan-1-one

In the manner described in Example 3, 2-(6-carboxyhexyl)cyclopentan-1-one (Example 8) is esterified to furnish the subject product, b.p. 110° C. (0.03 mm).

EXAMPLE 10

Preparation of 1-acetoxy-2-(6-carbethoxyhexyl)cyclopent-1-ene

A stirred solution of 100 g. of 2-(6-carbethoxyhexyl)-cyclopentan-1-one (Example 9) in 250 ml. of acetic anhydride containing 0.940 g. of p-toluenesulfonic acid monohydrate is heated to boiling under partial reflux allowing distillate at 118° C. or less (i.e., acetic acid) to escape through a Vigreux column equipped with a condenser to collect the distillate. After 16 hours, during which period acetic anhydride is added in portions in order to keep the solvent level at at least 100 ml., the solution is cooled and poured cautiously into a stirred cold mixture of saturated sodium bicarbonate solution (400 ml.) and hexane (250 ml.). The resulting mixture is stirred for an additional 30 minutes during which period solid sodium bicarbonate is added periodically to insure a basic solution. The hexane layer is separated and washed with saturated sodium chloride solution, dried with anhydrous magnesium sulfate and taken to dryness. Distillation of the residual oil gives 102 g. (87%) of pale yellow oil, b.p. 118° C. (0.07 mm).

EXAMPLE 11

Preparation of 1-acetoxy-2-(3-carbethoxypropyl)cyclopent-1-ene

In the manner described in Example 10, treatment of 2-(3-carbethoxypropyl)cyclopentan-1-one (Example 6) with acetic anhydride and p-toluenesulfonic acid monohydrate gives a yellow oil, b.p. 98°-103° C. (0.35 mm).

EXAMPLE 12

Preparation of 1-acetoxy-2-(4-carbethoxybutyl)cyclopent-1-ene

In the manner described in Example 10, treatment of 2-(4-carbethoxybutyl)cyclopentan-1-one (Example 3) with acetic anhydride and p-toluenesulfonic acid monohydrate gives a yellow oil, b.p. 109°-110° C. (0.37 mm).

EXAMPLE 13

Preparation of 2-(6-carbethoxyhexyl)cyclopent-2-en-1-one

To a rapidly stirred mixture of 50 g. of 1-acetoxy-2-(6-carbethoxyhexyl)cyclopent-1-ene (Example 10) in 150 ml. of chloroform, 200 ml. of water and 18.8 g. of calcium carbonate, cooled in an ice bath, is added dropwise over a period of about 30 minutes, a solution of 30 g. of bromine in 50 ml. of carbon tetrachloride. After stirring for an additional 45 minutes the chloroform layer is separated and washed successively with dilute sodium thiosulfate solution, saturated sodium chloride solution, dried with anhydrous magnesium sulfate and taken to dryness under reduced pressure.

The residual oil is dissolved in 50 ml. of N,N-dimethylformamide and added to a mixture of 33 g. of lithium bromide and 32 g. of lithium carbonate in 375 ml. of N,N-dimethylformamide, previously dried by refluxing with 375 ml. of benzene under a Dean-Stark apparatus followed by distillation of the benzene. The mixture is stirred at the reflux temperature for 30 minutes, then cooled and poured into 850 ml. of ice-cold water. The resulting mixture is acidified (cautiously) with 4N hydrochloric acid and extracted with ether three times. The combined ether extracts are washed with saturated sodium chloride solution dried with anhydrous magnesium sulfate and taken to dryness under reduced pressure to afford 41.5 g. of an amber oil. In order to convert any isomeric material to the desired product, 41.5 g. of the above material is treated with 0.500 g. of p-toluenesulfonic acid monohydrate in 450 ml. of absolute alcohol at the reflux temperature for 18 hours. The solution is taken to dryness under reduced pressure. The resulting gum is dissolved in ether and washed with saturated sodium bicarbonate solution, saturatd sodium chloride solution, dried with anhydrous magnesium sulfate and taken to dryness under reduced pressure. The residual oil is distilled to give 30.2 g. of product; b.p. 118° C. (0.05 mm); $\lambda_{max}^{MeOH}$ 229 mμ (ε9950); $\lambda_{max}$ 5.75, 5.85, 6.15, 8.45 μ; vapor phase chromatography shows 99% product, containing 1% 2-(6-carbethoxyhexyl)cyclopentan-1-one.

This product can be purified by the following procedure. A mixture of 120 g. of 2-(6-carbethoxyhexyl)-2-cyclopentenone, containing approximately 5% of the saturated analogue, and 7.67 g (10 mole percent) of p-carboxyphenylhydrazine in 400 ml. of absolute ethanol is stirred at ambient temperatures for 18 hours and is then refluxed for 1 hour. The mixture is cooled, the solvent is evaporated, and the residue is taken up into 150 ml. of chloroform and passed through a column of 450 g. of aluminum oxide (Merck). The [fltrate] *filtrate* is evaporated to yield a colorless oil containing <0.5% of the saturated impurity.

EXAMPLE 14

Preparation of 2-(3-carbethoxypropyl)cyclopent-2-en-1-one

In the manner described in Example 13, bromination of 1-acetoxy-2-(3-carbethoxypropyl)cyclopent-1-ene (Example 11) followed by dehydrobromination with lithium bromide and lithium carbonate is productive of the subject compound.

EXAMPLE 15

Preparation of
2-(4-carbethoxybutyl)cyclopent-2-en-1-one

In the manner described in Example 13, treatment of 1-acetoxy-2-(4-carbethoxybutyl)cyclopent-1-ene (Example 12) with bromine and subsequent treatment of the brominated product with a mixture of lithium bromide and lithium carbonate in N,N-dimethylformamide is productive of the subject compound. Treatment of this product with p-carboxyphenylhydrazine by the procedure of Example 13 furnishes a product which contains less than 0.5% of the corresponding saturated ketone.

EXAMPLE 16

Preparation of
1-methoximino-2-(6-carbethoxyhexyl)-2-cyclopentene

To a mixture of 35.97 g. (0.151 mole) or of 2-(6-carbethoxyhexyl)-2-cycopentenone (Example 13) and 15.0 g. (0.180 mole) of methoxyamine hydrochloride in 300 ml. of absolute ethanol is added 25 ml. of pyridine and the resulting solution is stirred for 20 hours at ambient temperatures. The solvent is evaporated and the residue is partitioned between water and diethyl ether. The organic phase is washed with water and saturated brine, dried ($Na_2SO_4$), and the solvent is evaporated to yeild an oil. Distillation yields 38.7 g. of a colorless oil, b.p. 115°-118° C. (0.075 mm). IR (film): 1740, 1627, 1053, 890 $cm^{-1}$. $\lambda_{max}$ (MeOH) 243 (13,000). NMR$\delta$($CDCl_3$): 3.89.

EXAMPLE 17

Preparation of
1-methoximino-2-(7-hydroxyheptyl)-2-cyclopentene

To an ice cooled solution of 34.10 g. (0.128 mole) of 1-methoximino-2-(6-carbethoxyhexyl)-2-cyclopentene (Example 16) in 200 ml. of benzene under nitrogen is added dropwise 225 ml. of a 25% solution of diisobutyl aluminum hydride in hexane. The resulting solution is stirred for 2 hours at 0°-5° C., poured onto ice and dilute hydrochloric acid, and the aqueous phase is saturated with sodium chloride. The organic phase is separated, washed with saturated brine, dried ($Na_2SO_4$), and evaporated to yield an oil. The latter is dissolved in 100 ml. of hot hexane and cooled to yield 24.3 g. of crystals, m.p. 62°-64° C. IR (KBr) 3260, 1630, 1059, 893 $cm^{-1}$. $\lambda_{max}$ 243 (14,200). NMR ($CDCl_3$)$\delta$: 2.37.

EXAMPLE 18

Preparation of
1-methoximino-2-(7-p-toluenesulfonyloxyheptyl)-2-cyclopentene

To a solution of 5.00 g. (0.222 mole) of 1-methoximino-2-(7-hydroxyheptyl)-2-cyclopentene (Example 17) in 50 ml. of dry pyridine at 0° C. is added 8.45 g. (0.0444 mole) of p-toluenesulfonyl chloride and the resulting solution is chilled at 5° C. overnight. The mixture is partitioned between 300 ml. of ice water and diethyl ether. The organic phase is washed with 1:1 ice cold hydrochloric acid, cold water, and cold saturated brine, dried ($NaSO_4/K_2CO_3$), and evaporated under reduced pressure at room temperature to yield an oil. The latter is dissolved in 600 ml. of hexane, treated with 0.5 g. of Darco, filtered and evaporated to yeild 7.7 g. of colorless oil. IR (film) 1600, 1192, 1182, 1053, 890 $cm^{-1}$. $\lambda_{max}$ (MeOH) 228 and 243.

EXAMPLE 19

Preparation of
1-methoximino-2-(8,8-dicarbethoxyoctyl)-2cyclopentene

To an alcoholic solution of sodiodiethyl malonate, prepared from 0.847 g. (0.0368 g. atoms) of sodium, 100 ml. of absolute ethanol, and 7.05 g. (0.0440 mole) of diethyl malonate is added 7.7 g. of the tosylate of Example 18 and the mixture is refluxed for 2 hours under a nitrogen atmosphere. The mixture is partitioned between cold dilute hydrochloric acid and diethyl ether, and the organic phase is washed with water and saturated brine, dried ($Na_2SO_4$), and evaporated to yield an oil. The excess diethyl malonate is distilled off under reduced pressure to yield 6.45 g. of a yellowish oil. IR (film) 1755, 1728, 1625, 1054, 890 $cm^{-1}$.

EXAMPLE 20

Preparation of
1-methoximino-2-(8,8-dicarboxyoctyl)-2-cyclopentene

A mixture of 6.45 g. of the diester of Example 19 and 6.72 g. of potassium hydroxide in 150 ml. of 1:1 aqueous methanol is refluxed for 1 hour, cooled, and is partitioned between water and diethyl ether. The aqueous phase is acidified with hydrochloric acid, extracted with ether, and the organic phase is washed with water and saturated brine, dried ($Na_2SO_4$) and evaporated to yield a solid. The solid is crystallized from benzene to yield 4.15 g. of tan crystals, m.p. 135°-137° C. (—$CO_2$).

EXAMPLE 21

Preparation of
1-methoximino-2-(8-carboxyoctyl)-2-cyclopentene

A solution of 3.926 g. (0.0126 mole) of the diacid of Example 20 in 20 ml. of xylene is refluxed for 1.5 hours, cooled and evaporated to yield a tan solid. IR (KBr) 1720, 1618, 1179, [1050,,] *1050,* 986 $cm^{-1}$.

EXAMPLE 22

Preparation of 2-(8-carboxyoctyl)cyclopent-2-en-1-one

The acid methoxime from Example 21 is refluxed for 5 hours with 55 ml. of acetone and 20 ml. of 2N hydrochloric acid. The mixture is cooled, the solvent is evaporated, and the residue is partitioned between water and diethyl ether. The organic phase is washed with water and saturated brine, dried ($Na_2SO_4$), and evaporated to yield a tan solid. IR (KBr) 1745, 1665 $cm^{-1}$. $\lambda_{max}$ (MeOH) 228 (12,600).

EXAMPLE 23

Preparation of
2-(8-carbethoxyoctyl)cyclopent-2-en-1-one

The acid ketone from Example 22 is Fisher esterfied with 100 ml. of absolute ethanol, 100 ml. of benzene, and 20 mg. of p-toluenesulfonic acid for 6 hours, cooled, and the solvent is evaporated. The resulting oil is dissolved in 3:1 benzene-ether and the solution is passed through a column of 100 g. of Florisil. The filtrate is evaporated and the residue is distilled to yield 2.97 g. of a colorless oil, b.p. 137°-139° C. (0.05 Torr).

EXAMPLE 24

Preparation of 2-(4-carbethoxybutyl)-2-cyclopentenone methoxime

Treatment of 2-(4-carbethoxybutyl)-2-cyclopentenone (Example 15) with methoxyamine hydrochloride in the manner described in Example 16 gives an oil, b.p. 107°-109° C. (0.05 mm). IR (film): 1740, 1628, 1050, 885 $cm^{-1}$. $\lambda_{max}$ (MeOH) 243 (13,600).

EXAMPLE 25

Preparation of 2-(5-hydroxypentyl)-2-cyclopentenone methoxime

Treatment of 2-(4-carbethoxybutyl)-2-cyclopentenomethoxime (Example 24) with diisobutyl aluminum hydride in the manner described in Example 17 gives crystals, m.p. 33°-35° C. IR (KBr) 3420, 1630, 1050, 886 $cm^{-1}$. $\lambda_{max}^{MeOH}$ 243 (12,020).

EXAMPLE 26

Preparation of 2-(5-p-toluenesulfonyloxypentyl)-2-cyclopentenone methoxime

Treatment of 2-(5-hydroxypentyl)-2-cyclopentenone methoxime (Example 25) with p-toluenesulfonyl chloride in pyridine in the manner described in Example 18 gives a colorless oil. IR (film) 1600, 1190, 1180, 1050, 885 $cm^{-1}$.

EXAMPLE 27

Preparation of 2-(6,6-dicarbethoxyoctyl)-2-cyclopentenone methoxime

To a solution of sodio diethyl ethylmalonate, prepared from 1.63 g. (0.0387 mole) of sodium hydride in mineral oil (57.2%), 100 ml. of ethylene glycol dimethyl ether and 8.5 g. (0.0452 mole) of ethyl diethyl malonate, is added 7.5 g. of tosylate from Example 26 in 20 ml. of ethylene glycol dimethyl ether and the mixture is refluxed for 3 hours and then allowed to stand at room temperature for 18 hours under nitrogen atmosphere. The reaction mixture is filtered and most of the solvent is removed. The mixture is partitioned between cold dilute hydrochloric acid and diethyl ether, and the organic phase is washed with water and saturated brine, dried ($MgSO_4$), and evaporated to yield an oil. The excess ethyl diethyl malonate is distilled off under reduced pressure to yield 6.7 g. of a yellow oil. IR (film) 1755, 1728, 1627, 1050, 885 $cm^{-1}$.

EXAMPLE 28

Preparation of 2-(6,6-dicarboxyoctyl)-2-cyclopentenone methoxime

Treatment of 2-(6,6-dicarbethoxyoctyl)-2-cyclopentene methoxime (Example 26) with potassium hydroxide, and 1:1 aqueous methanol in the manner described in Example 20 gives a light yellow oil.

EXAMPLE 29

Preparation of 2-(6-carboxyoctyl)-2-cyclopentenone methoxime

In the manner described in Example 21, treatment of 2-(6,6-dicarboxyoctyl)-2-cyclopentenone methoxime (Example 28) with xylene at reflux for 18 hours gives a yellow oil.

EXAMPLE 30

Preparation of 2-(6-carboxyoctyl)-2-cyclopentenone

Treatment of 2-(6-carboxyoctyl)-2-cyclopentenone methoxime (Example 29) with acetone and 2N hydrochloric acid in the manner described in Example 22 gives a light yellow oil.

EXAMPLE 31

Preparation of 2-(6-carbethoxyoctyl)-2-cyclopentenone

Treatment of 2-(6-carboxyoctyl)-2-cyclopentenone (Example 30) with thionyl chloride and then treatment of the acid chloride with ethanol in the usual manner gives an amber oil. The oil is placed on a magnesia-silica gel column and eluted with 3:1 benzene:ether. The solvent is removed and the residue is distilled, b.p. 122° C. (0.06 mm).

EXAMPLE 32

Preparation of diethyl 1,1-dimethyl-5-tetrahydropyranylpentylmalonate

To 486 mg. (0.02 g.-atoms) of magnesium in 5 ml. of toluene containing one molar equivalent of tetrahydrofuran per equivalent of magnesium and one percent iodine (calculated in weight of magnesium) is added dropwise 3.86 g. (0.02 mole) of 4-chloro-1-tetrahydropyranyloxybutane over a period of one hour with stirring, under nitrogen at 70° C. The reaction mixture is stirred at 70° C. for four hours. This reagent is then added dropwise to 3 g. (0.015 mole) of ethyl isopropylidenemalonate in 40 ml. of tetrahydrofuran containing 392 mg. of tetrakis [iodo(tri-n-butylphosphine)-copper (I)] and stirred at room temperature for 2 hours. The reaction mixture is poured into cold dilute hydrochloric acid and extracted with ether. The ether extract is dried over magnesium sulfate and concentrated to give 5.92 g. of subject product as an oil.

EXAMPLE 33

Preparation of diethyl 1,1-dimethyl-5-hydroxypentylmalonate

A solution of 3.5 g. (0.01 mole) of diethyl 1,1-dimethyl-5-tetrahydrofuranyloxypentylamalonate in 70 ml. of ethanol containing 3 ml. of hydrochloric acid is allowed to stir at room temperature for 18 hours. The solution is concentrated, diluted with water and extracted with ether. The ether extract is washed with water, dried over magnesium sulfate and concentrated to give 3.262 g. of a light yellow oil. The oil is purified by distillation, b.p. 116°-117° C. (0.05 mm).

EXAMPLE 34

Preparation of 3,3-dimethyl-7-hydroxyheptanoic acid

A mixture of 32 g. (0.117 mole) of diethyl 1,1-dimethyl-5-hydroxypentylmalonate, 25 g. of potassium hydroxide and 600 ml. of methanol-water (1:1) is heated at reflux for 8 hours and then allowed to stand at room temperature for 18 hours. The methanol is removed, diluted with water and the reaction mixture is acidified with concentrated hydrochloric acid. The mixture is extracted with ether. The extract is washed with water and saline, dried over anhydrous magnesium sulfate and concentrated to give 27 g. of 1,1-dimethyl-5-hydroxypentylmalonic acid. This crude oil is dissolved in 200 ml. of bis-(2-methoxyethyl)ether and is heated at reflux for 4 hours and then allowed to stand at room temperature overnight. The solvent is removed and the reaction mixture is diluted with water and extracted with ether. The organic solution is washed with saline, dried over magnesium sulfate and concentrated to give 18 g. of product as an oil.

EXAMPLE 35

Preparation of ethyl 3,3-dimethyl-7-chloroheptanoate

To a solution of 3.484 g. (0.02 mole) of 3,3-dimethyl-7-hydroxyheptanoic acid in 25 ml. of chloroform containing 3 drops of dimethylformamide is added 5.8 ml. (0.08 mole) of thionyl chloride and the solution is then heated at reflux for 3–4 hours. The solution is concentated to give the intermediate 3,3-dimethyl-7-chloro-1-heptanoyl chloride. The acid chloride is dissolved in a minimum amount of benzene and added slowly to 20 ml. benzene, 10 ml. of ethanol and 2.65 ml. of collidine. The solution is heated at reflux for one hour and then concentrated. The residue is dissolved in ether, washed with water, dilute sodium bicarbonate solution and saline. The organic solution is dried over magnesium sulfate and concentrated to give 3.57 g. of product as a yellow oil.

EXAMPLE 36

Preparation of ethyl 3,3-dimethyl-7-iodoheptanoate

To a solution of 3.57 g. (0.0162 mole) of ethyl 3,3-dimethyl-7-chloroheptanoate in 100 ml. of methyl ethyl ketone is added 4 g. of sodium iodide and the mixture heated at reflux for 18 hours. The reaction mixture is cooled, filtered and concentrated. The residue is partitioned between ether and water. The aqueous phase is extracted several times with ether. The extract is washed with sodium bisulfite solution, water and saline. The organic solution is dried over magnesium sulfate and concentrated to give 4.182 g. of a yellow oil. The material is purified by distillation, b.p. 86°–87° C. (0.18 Torr).

EXAMPLE 37

Preparation of
2-carbalkoxy(methyl/ethyl)-2-(6-carbethoxy-5,5-dimethylhexyl)cyclopentan-1-one This compound is prepared by treatment of sodiocyclopentanone carboxylate enolate with ethyl 3,3-dimethyl-7-iodoheptanoate by the procedure described in Example 1.

EXAMPLE 38

Preparation of
2-(6-carboxy-5,5-dimethylhexyl)cyclopentan-1-one

This compound is prepared by decarbalkoxylation of 2-carbalkoxy (mixed methyl and ethyl ester)-2-(6-carbethoxy-5,5-dimethylhexyl)cyclopentan-1-one by the procedure described in Example 2.

EXAMPLE 39

Preparation of
2-(6-carbethoxy-5,5-dimethylhexyl)cyclopentan-1-one

Esterification of 2-(6-carboxy-5,5-dimethylhexyl)cyclopentan-1-one with ethanol by the procedure described in Example 3 is productive of the subject compound.

EXAMPLE 40

Preparation of
1-acetoxy-2-(6-carbethoxy-5,5-dimethylhexyl)cyclopent-1-one

This compound is prepared from 2-(6-carbethoxy-5,5-dimethylhexyl)cyclopentan-1-one and acetic anhydride by the process described in Example 10.

EXAMPLE 41

Preparation of
2-(6-carbethoxy-5,5-dimethylhexyl)cyclopent-2-en-1-one

This compound is prepared from 1-acetoxy-2-(6-carbethoxy-5,5-dimethylhexyl)cyclopent-1-ene via bromination and dehydrobromination according to the procedure described in Example 13.

EXAMPLE 42

Preparation of
2-(3-carbethoxypropyl)-1-methoximino-2-cyclopentene

In the manner described for the preparation of the compound of Example 16, 2-(3-carbethoxypropyl)-1-methoximino-2-cyclopentene is prepared from 2-(3-carbethoxypropyl)-2-cyclopentenone (Example 14) and methoxyamine hydrochloride.

EXAMPLE 43

Preparation of
2-(4-hydroxybutyl)-1-methoximino-2-cyclopentene

In the manner described for the preparation of the compound of Example 17, 2-(4-hydroxybutyl)-1-methoximino-2-cyclopentene is prepared from 2-(3-carbethoxypropyl)-1-methoximino-2-cyclopentene and diisobutylaluminum hydride.

EXAMPLE 44

Preparation of
2-(6-carbethoxy-5-oxahexyl)-1-methoximino-2-cyclopentene

To an ice cold solution of 4.833 g. (0.0266 mole) of 2-(4-hydroxypentane)-1-methoximino-2-cyclopentene in 50 ml. of dry tetrahydrofuran under nitrogen is added 16.7 ml. of 1.6 molar n-butyl lithium in hexane, dropwise. The reaction mixture is stirred for 0.5 hour and then 4.85 g. (0.029 mole) of ethyl bromoacetate is added dropwise. The reaction mixture is stirred overnight at room temperature and then refluxed for 1.5 hours. The reaction is cooled and poured into water and extracted several times with ether. The ether extracts are washed with saline, dried over magnesium sulfate, and concentrated. The residue is placed on an alumina column, chloroform being used as a wash solvent. The combined washings are concentrated to dryness to give 4.903 g. of product an a yellow oil.

EXAMPLE 45

Preparation of
2-(6-carboxy-5-oxahexyl)-2-cyclopentenone

In the manner described in Example 22, treatment of 2-(6-carbethoxy-5-oxahexyl)-1-methoximino-2-cyclopentene with acetone and 2N hydrochloric acid at reflux gives the subject compound as a yellow oil.

EXAMPLE 46

Preparation of
2-(6-carbethoxy-5-oxahexyl)-2-cyclopentenone

In the manner described in Example 23, treatment of 2-(6-carboxy-5-oxahexyl)-2-cyclopentenone with p-toluenesulfonic acid in ethanol produces the subject product as a light yellow oil.

EXAMPLE 47

Preparation of
2-(6-carboxy-5-oxahexyl)-1-methoximino-2-cyclopente

To an ice cold solution of 3.66 g. (0.02 mole) of 2-(4-hydroxybutyl)-1-methoximino-2-cyclopentene (Example 43) in 50 ml. of 1,2-dimethoxyethane under nitrogen is added dropwise 17 ml. of 1.6M n-butyl lithium in hexane. The reaction mixture is stirred for half an hour and then the lithium salt of chloroacetic acid, prepared from 1.89 g. (0.02 mole) of chloroacetic acid and 16 ml. of 1.6M n-butyl lithium in 20 ml. of dimethoxyethane, is added and the reaction mixture is heated at reflux for 48 hours. The solvent is evaporated and the residue is partitioned between ether and water. The aqueous phase is acidified with hydrochloric acid and extracted with ether. The organic phase is washed with water and saturated saline solution, dried ($MgSO_4$), and evaporated to give 3.35 g. of a yellow oil.

EXAMPLE 48

Preparation of
2-(6-carboxy-5-oxahexyl)-2-cyclopenten-1-one

In the manner described in Example 22, treatment of 2-(6-carboxy-5-oxahexyl)-1-methoximino-2-cyclopentene (Example 47) with acetone and 2N hydrochloric acid at reflux gives the subject compound as a yellow oil.

EXAMPLE 49

Preparation of
1-methoximino-2-(4-methanesulfonyloxybutyl)-2-cyclopentene

To a solution of 1.83 g. (0.01 mole) of 1-methoximino-2-(4-hydroxybutyl)-2-cyclopentene (Example 43) in 10 ml. of methylene chloride containing 1.52 g. (0.015 mole) of triethylamine is added 1.265 g. (0.011 mole) of methanesulfonyl chloride over a period of 5-10 minutes at −10°-0° C. Stirring is continued for 15 minutes and the solution is then washed with cold water cold 10% hydrochloric acid, cold sodium bicarbonate solution, and cold saline solution. The organic phase is dried ($MgSO_4$) and concentrated to give an oil which solidifies upon cooling. Crystallization from ether-petroleum ether (30°-60° C.) gives 1.797 g. of white crystals, m.p. 67°-68° C.

EXAMPLE 50

Preparation of
1-methoximino-2-(5-cyanopentyl)-2-cyclopentene

A mixture of 2.75 g. (0.01 mole) of 1-methoximino-2-(5-methanesulfonyloxypentyl)-2-cyclopentene (Example 60) and 1.47 g. (0.03 mole) of sodium cyanide in 20 ml. of dry N,N-dimethylformamide is heated at 65°-70° C. for 3 hours. The cooled reaction mixture is poured into water and extracted with diethyl ether. The organic phase is washed with water and saturated saline solution, dried ($MgSO_4$), and evaporated to give 1.89 g. of a light yellow oil.

EXAMPLE 51

Preparation of
1-methoximino-2-(5-carboxypentyl)-2-cyclopentene

A mixture of 1.89 g. (0.0092 mole) of 1-methoximino-2-(5-cyanopentyl)-2-cyclopentene (Example 50) and 1 g. (0.025 mole) of sodium hydroxide in 50 ml. of 1:1 aqueous-ethanol is refluxed for 48 hours, coled, and partitioned between water and diethyl ether. The aqueous phase is acidified with hydrochloric acid, extracted with diethyl ether, and the organic phase is washed with water and saturated saline solution, dried ($MgSO_4$), and evaporated to give 1.86 g. of a yellow oil.

EXAMPLE 52

Preparation of 2-(5-carboxypentyl)-2-cyclopentenone

A solution of 1.86 g. (0.00825 mole) 1-methoximino-2-(5-carboxypentyl)-2-cyclopentene (Example 51) in 44 ml. of acetone and 13.1 ml. of 2N hydrochloric acid is refluxed for 5 hours. The solvent is partially evaporated and a solid precipitates and is collected. The residue is extracted with diethyl ether and the organic phase is washed with saturated saline solution, dried ($MgSO_4$), and evaporated to yield additional solid. The combined solid material is crystallized from ether/pet ether (30°-60° C) to yield crystalline material, m.p. 70°-72° C.

EXAMPLE 53

Preparation of
2-(5-carbethoxypentyl)-2-cyclopentenone

A solution of 1.309 g. (0.00668 mole) of 2-(5-carboxypentyl)-2-cyclopentenone (Example 52) and 90 mg. of p-toluenesulfonic acid in 150 ml. of ethanol is refluxed for 18 hours. The solvent is evaporated and the residue is dissolved in ether. The organic phase is washed with water, sodium bicarbonate solution, and saturated saline solution, dried ($MgSO_4$), and evaporated to give 1.371 g. of light yellow oil.

EXAMPLE 54

Preparation of
2-(5-acetoxypentyl-2-carbomethoxy/carbethoxy-cyclopentanone

A mixture of sodiocyclopentanone carboxylate, prepared from 1200 g. (8.0 moles) of cyclopentanone carboxylate (methyl and ethyl esters) and 200 g. (8.3 moles) of mineral oil free sodium hydride in 10 l. of 1,2-dimethoxyethane, 1320 g. (8.0 moles) of 5-chloro-1-amyl acetate [M.E. Synerholm, Journ. Amer. Chem. Soc., 69, 2681 (1947)], and 1200 g. (8.0 moles) of sodium iodide is refluxed under nitrogen for 18 hours. The mixture is cooled, connected to 4 l. and partitioned between dilute hydrochloric acid and diethyl ether. The organic phase is washed with water and saturated brine, dried ($MgSO_4$), and evaporated to yield 1920 g. of an oil.

EXAMPLE 55

Preparation of
2-(5-hydroxypentyl)cyclopentanone/2-(5-acetoxypentyl)-cyclopentanone A mixture of 4,500 g. (16.2 moles) of 2-(5-acetoxypentyl)-2-carbomethoxy/carboethoxy-cyclopentanone (Example 54), 2.2 l. of glacial acetic acid, 1 l. of concentrated hydrochloric acid, and 1 l. of water is refluxed for 18 hours, cooled, and partitioned between saturated brine and benzene. The organic phase is washed with saturated brine, dried ($MgSO_4$), and evaporated in vacuo to yield 3155 g. of an oil.

EXAMPLE 56

Preparation of
1-acetoxy-2-(5-acetoxypentyl)-1-cyclopentene

A solution of 400 g. (2.04 moles) of a mixture of 2-(5-hydroxypentyl)cyclopentanone and 2-(5-acetoxypentyl)cyclopentanone (Example 55) and 4.0 g. of p-toluenesulfonic acid monohydrate in 11 l. of acetic anhydride is refluxed acetic a rate to maintain a steady distillation of acetic acid from the reaction through a relix-packed fractionation column. The reaction is continued with the addition of acetic anhydride to maintain a constant volume until complete conversion of starting materials to product is evident. The mixture is cooled and partitioned between 2 l. of hexane and 3 l. of cold water containing solid sodium bicarbonate to maintain a neutral pH. The organic phase is washed with saturated brine, dried ($MgSO_4$), and evaporated to yield 452 g. of an oil.

EXAMPLE 57

Preparation of 2-(5-acetoxypentyl)-2-cyclopentenone

To a well stirred mixture of 405 g. (4.05 moles) of calcium carbonate, 3 l. of water, and 2.5 l. of chloroform cooled to 5° C. is added simultaneously 1016 g. (4.0 moles) of 1-acetoxy-2-(5-acetoxy-pentyl)-1-cyclopentene (Example 56) and a solution of 648 g. (4.05 moles) of bromine in 500 ml. of carbon tetrachloride at a rate to maintain a temperature below 10° C. The mixture is stirred for half an hour after addition of the reagents and the phases are then separated. The organic phase is washed with 2% sodium thiosulfate solution, water, and saturated brine, dried ($MgSO_4$), and evaporated in vacuo to an oil. The oil is immediately added to a refluxing slurry of 500 g. (5.0 moles) of calcium carbonate in 2.5 l. of N,N-dimethylacetamide under nitrogen and the mixture is then refluxed for 30 minutes. The mixture is cooled, filtered, and partitioned between water and diethyl ether. The organic phase is washed with water and saturated brine, dried ($MgSO_4$), and evaporated to yield 757 g. of an oil, b.p. 116°-118° C. (0.25 mm.).

EXAMPLE 58

Preparation of
1-methoximino-2-(5-acetoxypentyl)-2-cyclopentene

In the manner described for Example 16, 2-(5-acetoxypentyl)-2-cyclopentenone (Example 57) is treated with methoxyamine hydrochloride in pyridine and ethanol to yield the subject compound, b.p. 101°-103° C. (0.20 mm.).

EXAMPLE 59

Preparation of
1-methoximino-2-(5-hydroxypentyl)-2-cyclopentene

A mixture of 74 g. (0.22 mole) of 1-methoximino-2-(5-acetoxypentyl)-2-cyclopentene (Example 58) and 56 g. (1.0 mole) of potassium hydroxide in 300 ml. of 1:1 aqueous methanol is refluxed for 2 hours and then cooled. The solvent is partially removed in vacuo and the residue is partitioned between saturated brine and diethyl ether. The organic phase is washed with saturated brine, dried ($MgSO_4$), and evaporated to yield an oil which crystallized, m.p. 35°-36° C.

EXAMPLE 60

Preparation of
1-methoximino-2-(5-methanesulfonyloxypentyl)-2-cyclopentene

To a cold solution of 9.85 g. (0.05 mole) of 1-methoximino-2-(5-hydroxypentyl)-2-cyclopentene (Example 59) and 7.6 g. (0.075 mole) of triethylamine in 100 ml. of methylene chloride at −10° C. is added 6.3 g. (0.055 mole) of methanesulfonyl chloride at a rate to maintain a temperature of −10° C. The mixture is then stirred for 15 minutes and then poured into ice water. The organic phase is washed with cold 10% hydrochloric acid, cold saturated sodium bicarbonate solution, and cold saturated brine, dried ($MgSO_4$), and evaporated to yield a solid, m.p. 78°-80° C.

EXAMPLE 61

Preparation of
1-methoximino-2-(6,6-dicarbethoxyhexyl)-2-cyclopentene

To a suspension of sodiodiethylmalonate in 1,2-dimethoxyethane, prepared from 248 g. (1.55 moles) of diethyl malonate and 17.2 g. (0.95 mole) of mineral oil free sodium hydride in 1 l. of 1,2-dimethoxyethane under nitrogen, is added 170 g. (0.62 mole) of 1-methoximino-2-(5-methanesulfonyloxypentyl)-2-cyclopentene (Example 60) in 1.5 l. of 1,2-dimethoxyethane and the mixture is refluxed for 5 hours. The mixture is cooled, filtered, and the solvent is evaporated. The residue is partitioned between cold dilute hydrochloric acid and water, and the organic phase is washed with saturated brine, dried ($MgSO_4$), and evaporated to remove solvent and excess diethyl malonate to yield 209 g. of an oil.

EXAMPLE 62

Preparation of
1-methoximino-2-(6,6-dicarboxyhexyl)-2-cyclopentene

In the manner described in Example 20, 1-methoximino-2-(6,6-dicarbethoxyhexyl)-2-cyclopentene is treated with potassium hydroxide in 1:1 aqueous methanol and then hydrochloric acid to yield the desired compound as crystals from diethyl ether, m.p. 110°-115° C.

EXAMPLE 63

Preparation of
1-methoximino-2-(6-carboxyhexyl)-2-cyclopentene

A solution of 141 g. (0.50 mole) of 1-methoximino-2-(6,6-dicarboxyhexyl)-2-cyclopentene in 500 ml. of bis-(2-methoxyethyl) ether is refluxed for 2 hours, cooled, and evaporated to yeild an oil. The latter is crystallized from hexane to yield 92 g. of solid, m.p. 70°-72° C.

EXAMPLE 64

Preparation of 2-(6-carboxyhexyl)-2-cyclopentenone

In the manner described in Example 22, treatment of 1-methoximino-2-(6-carboxyhexyl)-2-cyclopentene (Example 63) with acetone and 2N hydrochloric acid at reflux provides the subject compound.

EXAMPLE 65

Preparation of 2-(6-carbethoxyhexyl)-2-cyclopentenone

Fischer estification of 2-(6-carboxyhexyl)-2-cyclopentenone (Example 64) in the manner of Example 23 provides the subject compound.

EXAMPLE 66

Preparation of 1-methoximino-2-(6-fluoro-6,6-dicarbethoxyhexyl)-2-cyclopentene

To a solution of sodiodiethyl fluoromalonate, prepared from 2.062 g. (0.0491 mole) of sodium hydride in mineral oil (57.2%), 40 ml. of dry N,N-dimethylformamide and 8.174 g. (0.0458 mole) of diethyl fluoromalonate is added dropwise 11.32 g. (0.0413 mole) of 1-methoximino-2-(5-methylsulfonyloxypentyl)-2-cyclopentene (Example 60) in 60 ml. of N,N-dimethylformamide. The mixture is refluxed for 2 hours under a nitrogen atmosphere. The mixture is concentrated and partitioned between cold dilute hydrochloric acid and diethyl ether, and the organic phase is washed with saturated brine, dried ($MgSO_4$), and evaporated to yield 13.631 g. (92%) of a yellow oil.

EXAMPLE 67

Preparation of 1-methoximino-2-(6fluoro,6,6-dicarboxyhexyl)-2-cyclopentene

A mixture of 13.631 g. of the diester of Example 66 and 16 g. of potassium hydroxide in 364 ml. of 1:1 aqueous methanol is refluxed for 5 hours, cooled, concentrated, and is partitioned between water and diethyl ether. The aqueous phase is acidified with hydrochloric acid, extracted with ether, and the organic phase is washed with saturated brine, dried ($MgSO_4$), and evaporated to yield a solid. The solid is crystallized free diethyl ether petroleum ether (30°–60° C.) to give 10 g. (90%) of white crystals, m.p. 143°–145° C. (—$CO_2$).

EXAMPLE 68

Preparation of 1-methoximino-2-(6-fluoro-6-carboxyhexyl)-2-cyclopentene

A solution of 10 g. of the diacid of Example 67 in 60 ml. of 2-methoxyethyl ether is refluxed for 7 hours, cooled, and evaporated to yield 8.5 g. (95%) of a tan solid. A sample is crystallized from diethyl ether-petroleum ether (30°–60° C.) to give white crystals, m.p. 98°–100° C.

EXAMPLE 69

Preparation of 2-(6-fluoro-6-carboxyhexyl)cyclopent-2-en-1-one

The acid methoxime (8.5 g.) from Example 68 is refluxed for 5 hours with 180 ml. of acetone and 64 ml. of 2N hydrochloric acid. The mixture is cooled, the solvent is evaporated, and the residue is partitioned between water and diethyl ether. The organic phase is washed with saturated brine, dried ($MgSO_4$), and evaporated to yield 7.4 g. (98%) of a light yellow oil.

EXAMPLE 70

Preparation of 2-(6-fluoro-6-carbethoxyhexyl)cyclopent-2-en-1-one

The acid ketone (7.4 g.) from Example 69 is Fisher esterified with 300 ml. of absolute ethanol and 400 mg. of p-toluenesulfonic acid for 18 hours, cooled and the solvent is evaporated. The resulting oil is dissolved in ether, washed with dilute sodium bicarbonate solution, and saline, dried ($MgSO_4$) and evaporated to give 7.306 g. (86%) of a light yellow oil.

EXAMPLE 71

Preparation of 2-(7-cyanoheptyl)-1-methoximino-2-cyclopentene

Treatment of 1-methoximino-2-(7-p-toluenesulfonyloxy)-2-cyclopentene (Example 18) with sodium cyanide in the manner of Example 50 is productive of the subject compound.

EXAMPLE 72

Preparation of 2-(7-carboxyheptyl)-1-methoximino-2-cyclopentene

Alkaline hydroylsis of 2-(7-cyanoheptyl)-1-methoximino-2-cyclopentene (Example 71) of th eprocedure of Example 51 is productive of the subject compound.

EXAMPLE 73

Preparation of 2-(7-carboxyheptyl)-2-cyclopenten-1-one

Hydrolysis of the methoxime of Example 72 with acetone-hydrochloric acid by the procedure of Example 52 is productive of the subject compound.

EXAMPLE 74

Preparation of 2-(7-carbethoxyheptyl)-2-cyclopenten-1-one

Fisher esterification of the carboxylic acid of Example 73 by the procedure of Example 53 is productive of the subject compound.

EXAMPLE 75

Preparation of 2-(6,6-dicarbethoxy-6-phenylhexyl)-1-methoximino-2-cyclopentene

Treatment of 1-methoximino-2-(5-methanesulfonyloxypentyl)-2-cyclopentene (Example 60) with sodio diethyl phenylmalonate by the procedure of Example 61 is productive of the subject compound.

EXAMPLE 76

Preparation of 2-(6,6-dicarboxy-6-phenylhexyl)-1-methoximino-2-cyclopentene

Alkaline hydrolysis of 2-(6,6-dicarbethoxy-6-phenylhexyl)-1-methoximino-2-cyclopentene (Example 75) by the procedure of Example 20 is productive of the subject diacid.

EXAMPLE 77

Preparation of
2-(6-carboxy-6-phenylhexyl)-1-methoximino-2-cyclopentene-dicarbethoxy Decarboxylation of 2-(6,6-dicarboxy-6-phenylhexyl)-1-methoximino-2-cyclopentene (Example 76) by the procedure of Example 63 is productive of the subject compound.

EXAMPLE 78

Preparation of
2-(6-carboxy-6-phenylhexyl)-2-cyclopentene-1-one

Methoxime cleavage of 2-(6-carboxy-6-phenylhexyl)-1-methoximino-2-cyclopentene (Example 77) in the manner of Example 69 is productive of the subject ketone.

EXAMPLE 79

Preparation of
2-(6-carbethoxy-6-phenylhexyl)-2-cyclopentene-1-one

Fisher esterification of the carboxylic acid of Example 78 in the manner of Example 70 is productive of the subject keto-ester.

EXAMPLE 80

Preparation of
2-(6-fluoro-6,6-dicarbethoxyhexyl)-1-methoximino-2-cyclopentene

An ethanolic solution of sodium ethoxide, prepared from 0.389 g. of sodium and 40 ml. of absolute ethanol, is treated at ambient temperatures with 5.05 g. of 2-(6,6-dicarbethoxyhexyl)-1-methoximino-2-cyclopentene (Example 61). The resulting solution is cooled to −20° C. and then treated with a stream of perchloryl fluoride until the mixture becomes neutral. The excess perchloryl fluoride is removed with a stream of nitrogen and the mixture is retreated with 10 ml. of an ethanol solution of sodium ethoxide (from 0.350 g. of sodium) and then with perchloryl fluoride until the mixture becomes neutral. The excess perchloryl fluoride is removed with a stream of nitrogen and the mixture is filtered an evaporated to an oil. The latter is partitioned between ether and water and the organic phase is washed with saturated saline, dried ($Na_2SO_4$) and evaporated to afford the subject compound.

EXAMPLE 81

Preparation of
2-(6-carbo-n-butoxyhexyl)cyclopent-2-en-1-one

A solution of 50 g. of 2-(6-carboxyhexyl)cyclopent-2-en-1-one [Bagli et al., Tertrahedron Letters, No. 5, 465 (1966)] in 400 ml. of n-butanol containing 2.7 g. of p-toluenesulfonic acid monohydrate is allowed to stand at room temperature in a stoppered flask for about 24 hours. The solution is taken to dryness. The residue is taken up in ether and the ethereal solution is washed several times with saline solution, dried with anhydrous magnesium sulfate, and taken to dryness to afford the subject butyl ester.

EXAMPLES 82–84

Treatment of 2-(6-carboxyhexyl)cyclopent-2-en-1-one by the procedure of Example 81 with the appropriate alcohol affords the esters of the following table.

TABLE IV

| Example | Alcohol | Product Ester |
|---|---|---|
| 82 | isopropanol | 2-(6-carboisopropoxyhexyl)cyclopent-2-en-1-one |
| 83 | methanol | 2-(6-carbomethyoxyhexyl)cyclopent-2-en-1-one |
| 84 | 1-hydroxy-n-decane | 2-(6-carbo-n-decyloxyhexyl)cyclopent-2-en-1-one |

EXAMPLE 85

Preparation of diethyl
(5-chloro-1,1-dimethylpentyl)malonate

To magnesium (71 g. 2.92 moles) under 1 l. of ether containing a few crystals of iodine is added dropwise 1-chloro-4-bromobutane (500 g., 2.92 moles) over a period of 30 minutes with stirring under nitrogen. The reaction is maintained at a temperature of 0° C. to 5° C. by immersing in an acetone-Dry Ice bath periodically. After stirring for 30 minutes at room temperature, the solution is chilled to below 0° C. and is then transferred to a dropping funnel from which it is added dropwise to diethyl isopropylidene malonate (440 g., 2.19 moles) [A.C. Cope and E. M. Hancock, J.A.C.S. 60, 2644 (1938)] dissolved in 1000 ml. of ether containing the tri(n-butyl)phosphine complex of copper (I) iodide (57 g.) [G. B. Kaufman and L. A. Teter, Inorganic Synthesis, 7, 9(1963)] at −10° C. with stirring under nitrogen over a period of 2 hours. After stirring at room temperature for 4 hours, the reaction mixture is poured into cold dilute hydrochloric acid and is extracted with ether. The combined ether extracts are washed with saline solution, dried over magnesium sulfate, and concentrated in vacuo to give 700 g. of crude amber oil, which is distilled under vacuum to yield two fractions: 212.4 g. with b.p. at 110°–135° C. at 0.3 mm. and 100.0 g. with b.p. at 135°–145° C. at 0.3 mm. The total yield is 312.4 g. (49%).

EXAMPLE 86

Preparation of 3,3-dimethyl-7-chloroheptanoic acid

A mixture containing diethyl 5-(5-chloro-1,1-dimethylpentyl)malonate (648 g., 2.22 moles) potassium hydroxide (460 g. and eight liters of 1:1 isopropanol:water is stirred at room temperature overnight. Most of the isopropanol is distilled and the residue is diluted with water, and then carefully acidified with conc. hydrochloric acid. The mixture is extracted with ether and the extracts are washed with water and saline, dried over magnesium sulfate and concentrated in vacuo to give 548 g. of crude oil. The oil is dissolved in three liters of diglyme which is heated under reflux for sixteen hours. About 2.7 l. of solvent is distilled, and the remainder is diluted with water and extracted with ether. The extracts are washed with saline, dried over magnesium sulfate and concentrated in vacuo to give 428 g. of crude oil (99%).

EXAMPLE 87

Preparation of ethyl 3,3-dimethyl-7-chloroheptanoate

To a solution of 3,3-dimethyl-7-chloroheptanoic acid (428 g., 2.21 moles) in 3 l. of chloroform containing 3 ml. of N,N-dimethylformamide is added 500 ml. of thionyl chloride and the resulting solution is tested under reflux for 3 hours. The reaction solution then is concentrated in vacuo and the residual acid chloride is dissolved in a minimum amount of benzene and added slowly to a solution containing 1260 ml. of 95% ethanol and 2520 ml. of benzene and 390 ml. of collidine. After heating under reflux for one hour, the solution is concentrated and the residue is dissolved in ether washed with water, dilute sodium bicarbonate solution and saline solution, dried over magnesium sulfate and concentrated to give 415 g. of crude oil, which is distilled under vacuum to yield two fraction 46.6 g. boiling at 75° C. (0.3 mm.) and 236.7 g. boiling at 75°-80° C. (0.3 mm). The total yield is 283.3 g. (60%) and the product is indicated to be 95% pure by g.l.c.

EXAMPLE 88

Preparation of methyl/ethyl 2-(6-carbethoxy-5,5-dimethylhexyl) cyclopentanone-2-carboxylate Sodium hydride (67 g., 1.55 moles) is placed in a three l. round-bottom flask and to this is added 1.1 liters of glyme from a dropping funnel under nitrogen flow and with stirring. To the resulting grayish mixture is added the 2-carbalkoxycyclopentanone (mixed methyl and ethyl esters) dropwise over a period of 45 minutes with nitrogen flow whilst the temperature is maintained in the range of 40°-55°. Ethyl 3,3-dimethyl-7-chloroheptanoate (283 g., 1.28 moles) and potassium iodide (195 g., 1.32 moles) are added and the mixture is heated at reflux overnight. After most of the solvent is distilled, the residue is made acidic with dilute hydrochloric acid and is then extracted with ether. The ether extracts are washed with water and saline solution, dried over magnesium sulfate, and concentrated in vacuo to 500 g. of crude yellow oil, which is distilled to give 405 g. (94% yield) of oil with b.p. 140°-180° (0.8 mm).

EXAMPLE 89

Preparation of 7-(2-cyclopentanone)-3,3-dimethylheptanoic acid

Methyl/Ethyl 2-(6-carbethoxy-5,5-dimethylhexyl) cyclopentanone-2-carboxylate (200 g., 0.6 moles), glacial acetic acid (180 ml) and 240 ml. of diluted hydrochloric acid, prepared from 100 ml. of conc. hydrochloric acid and 300 ml. of water, are placed in a 2 l. flask, containing a reflux condenser and a magnetic stirrer. The mixture then is stirred at reflux for 24 hours. The reaction mixture is cooled, 1 l. of water is added and the mixture is extracted several times with benzene. The organic extracts are combind, washed with saturated sodium chloride solution, dried over magnesium sulfate, filtered and concentrated to an oil (173.5 g.). The oil is rendered basic with sodium hydroxide solution, extracted with benzene and made acidic with hydrochloric acid and reextracted with benzene several times. The benzene layers are combined and washed with water, saturated sodium chloride solution, dried over magnesium sulfate, filtered and concentrated to yield 109.8 g. (78%) of crude oil, which was used without further purification in the next step.

EXAMPLE 90

Preparation of ethyl 7-(2-cyclopentanone)-3,3-dimethylheptanoate

To a solution of 7-(2-cyclopentanone)-3,3-dimethylheptanoic acid (45 g., 0.22 mol.) in 285 ml. of chloroform containing three drops of N,N-dimethylformamide is added dropwise 25 ml. of thionyl chloride. The solution is stirred at room temperature for 20 minutes, the solvent is removed at reduced pressure and the residual acid chloride is dissolved in a minimum amount of benzene and added slowly to a solution containing 115 ml. of ethanol, 230 ml. benzene and 30 ml. of collodine. This solution is heated under reflux for 15 minutes and then concentrated. The residue is dissolved in ether, washed with water, diluted sodium bicarbonate solution and saline solution, dried over magnesium sulfate and concentrated to give 51 g. of crude oil. Distillation gives 40 g. (67%) b.p. 135-145 (0.1 mm.) of oil.

EXAMPLE 91

Preparation of 1-acetoxy-2-(6-carbethoxy-5,5-dimethylhexyl)cyclopent-1-ene

A solution of ethyl 7-(2-cyclopentanone)-3,3-dimethylheptanoate (90g., 0.336 mol.) and p-toluenesulfonic acid (0.94 g.) in 250 ml. of acetic anhydride is heated to boiling under partial reflux, allowing distillate at 118° or less (i.e. acetic acid) to escape thru a Vigreux column equipped with a condenser to collect the distillate. After ten hours 130 ml. of distillate is collected. Another 50 ml. of acetic anhydride is added and the reaction is heated for 5 more hours; an additional 125 ml. of acetic anhydride is added, the reaction is heated for 7 more hours; finally another 50 ml. of acetic anhydride is added and heating is continued for 4 more hours. The solution is cooled and poured (cautiously) into a cold (0°-5°) mixture of saturated aqueous sodium bicarbonate (400 ml.) and hexane (250 ml.). The resulting cold mixture is stirred for 30 minutes during which time portions of solid sodium bicarbonate are added periodically until carbon dioxide evalution ceases. The hexane layer is separated and washed with saturated sodium chloride solution until the washings are neutral, dried over magnesium sulfate and treated with Darco decolorizing charcoal for clarification and then evaporated to dryness leaving an amber colored oil (87.5 g., 84%).

EXAMPLE 92

Preparation of 2-(6-carboxy-5,5-dimethylhexyl)cyclopent-2-en-1-one

To a rapidly stirred mixture of 1-acetoxy-2-(6-carbethoxy-5,5-dimethylhexyl)cyclopent-1-ene (35 g., 0.113 mole) chloroform (95 ml.), water (125 ml.) and calcium carbonate (11.8 g.) cooled in an ice-bath is added dropwise over a period of thirty minutes a solution of bromine (18.8 g.) in carbon tetrachloride (31 ml.). After stirring in the cold for an additional 45 minutes the orange colored chloroform layer is separated and washed with dilute sodium bisulfite and saturated saline solution, dried over magnesium sulfate and taken to dryness in vacuo (bath temperature: 35°-40°) leaving an amber colored oil. A slurry of 100 ml. of N,N-dimethylacetamide and 16.5 g. of $CaCO_3$ is stirred and heated to reflux under nitrogen flow. The above dried oil is added from a dropping funnel rapidly, maintaining reflux and nitrogen flow for 30 minutes. The cooled reaction mixture is filtered, and the precipitate is washed with ether. The filtrate is poured into two liters ice-cold water and is extracted with ether. The combined extracts and washing is washed with water, saturated saline, treated with decolorizing charcoal, filtered. The solvent evaporated in vacuo to give 24 g. (77%) of subject product.

EXAMPLE 93

Preparation of 4-bromo-2-(6-carboxyhexyl)cyclopent-2-en-1-one

A stirred mixture of 35.9 g. (0.171 moles) of 2-(6-carboxyhexyl)cyclopent-2-en-1-one [Bagli et al., Tetrahedron Letters, No. 5, 465 (1966)], 35.0 g. (0.197 moles) of N-bromosuccinimide, and 600 ml. of carbon tetrachloride is refluxed for 35 minutes. The mixture is cooled to 5° C. and filtered. The filtrate is washed with cold water, dried over magnesium sulfate, and taken to dryness to give an oil, $\lambda$ max.$^{MeOH}$ = 225 m$\mu$ (8850); $\nu$ max. = 1705 (carbonyl groups) and 1625. cm$^{-1}$ (olefin group).

EXAMPLES 94–118

In the manner of the preceding Example 93, the various cyclopentenones of Table V, which follows, are converted to the corresponding 4-bromo derivatives.

TABLE V

| Ex. | Starting Cyclopentenone of Example | Product 4-Bromocyclopentenone |
|---|---|---|
| 94 | 13 | 4-bromo-2-(6-carbethoxyhexyl)-cyclopent-2-en-1-one |
| 95 | 83 | 4-bromo-2-(6-carbomethoxyhexyl)-cyclopent-2-en-1-one |
| 96 | 15 | 4-bromo-2-(4-carbethoxybutyl)-cyclopent-2-en-1-one |
| 97 | 14 | 4-bromo-2-(3-carbethoxypropyl)-cyclopent-2-en-1-one |
| 98 | 2 | 4-bromo-2-(4-carboxybutyl)cyclopent-2-en-1-one |
| 99 | 5 | 4-bromo-2-(3-carboxypropyl)cyclopent-2-en-1-one |
| 100 | 22 | 4-bromo-2-(8-carboxyoctyl)cyclopent-2-en-1-one |
| 101 | 23 | 4-bromo-2-(8-carbethoxyoctyl)cyclopent-2-en-1-one |
| 102 | 30 | 4-bromo-2-(6-carboxyoctyl)cyclopent-2-en-1-one |
| 103 | 31 | 4-bromo-2-(6-carbethoxyoctyl)cyclopent-2-en-1-one |
| 104 | 92 | 4-bromo-2-(6-carboxy-5,5-dimethylhexyl)cyclopent-2-en-1-one |
| 105 | 41 | 4-bromo-2-(6-carbethoxy-5,5-dimethylhexyl)cyclopent-2-en-1-one |
| 106 | 45 | 4-bromo-2-(6-carboxy-5-oxahexyl)-cyclopent-2-en-1-one |
| 107 | 46 | 4-bromo-2-(6-carbethoxy-5-oxahexyl)-cyclopent-2-en-1-one |
| 108 | 69 | 4-bromo-2-(6-carboxy-6-fluorohexyl)-cyclopent-2-en-1-one |
| 109 | 70 | 4-bromo-2-(6-carbethoxy-6-fluorohexyl)cyclopent-2-en-1-one |
| 110 | 52 | 4-bromo-2-(5-carboxypentyl)cyclopent-2-en-1-one |
| 111 | 53 | 4-bromo-2-(5-carbethoxypentyl)cyclopent-2-en-1-one |
| 112 | 73 | 4-bromo-2-(7-carboxyheptyl)cyclopent-2-en-1-one |
| 113 | 74 | 4-bromo-2-(7-carbethoxyheptyl)-cyclopent-2-en-1-one |
| 114 | 78 | 4-bromo-2-(6-carboxy-6-phenylhexyl)cyclopent-2-en-1-one |
| 115 | 79 | 4-bromo-2-(6-carbethoxy-6-phenylhexyl)cyclopent-2-en-1-one |
| 116 | 81 | 4-bromo-2-(6-carbo-n-butoxyhexyl)-cyclopent-2-en-1-one |
| 117 | 82 | 4-bromo-2-(6-carbo-isopropoxyhexyl)-cyclopent-2-en-1-one |
| 118 | 84 | 4-bromo-2-(6-carbo-n-decyloxyhexyl)cyclopent-2-en-1-one |
| 118a | 272 | 4-bromo-2-(6-carboxyheptyl)-cyclopent-2-en-1-one |

EXAMPLE 119

Preparation of 4-hydroxy-2-(8-carboxyoctyl)cyclopent-2-en-1-one

To a stirred solution of 57.2 g. of crude 4-bromo-2-(8-carboxyoctyl)cyclopent-2-en-1-one (Example 100) in 500 ml. of acetone and 325 ml. of water at 3° C. is added 44.1 g. (0.226 moles) of silver fluoborate during a 15 minute period. The mixture is stirred at 0°–3° C. for 2 hours and filtered. The filtrate is diluted with water, saturated with solid sodium chloride, and extracted with ether. The extract is washed with saturated sodium chloride solution, dried over magnesium sulfate, and concentrated. Partition chromatography of the residue on Celite gives white crystals, m.p. 58°–66° C., $\lambda$ max.$^{MeOH}$ = 223 m$\mu$ (7800); $\nu$ max (KBR) = 3340 (hydroxyl groups), 1705 (carbonyl groups), and 1625 cm$^{-1}$ (olefin group).

EXAMPLE 120

Preparation of 4-acetoxy-2-(6-carbethoxyhexyl)cyclopent-2-en-1-one

A mixture of 51.6 g. (0.137 moles) of crude 4-bromo-2-(6-carbethoxyhexyl)cyclopent-2-en-1-one (Example 94), 27 g. (0.162 moles) of silver acetate, and 200 ml. of glacial acetic acid is stirred at reflux for 4.5 hours. The mixture is cooled, and solids are removed by filtration. The filtrate is concentrated and extracted with hot hexane. The extract is washed with saturated sodium bicarbonate solution and saturated sodium chloride solution, dried over magnesium sulfate, and concentrated to give an oil. The crude product is distilled at reduced pressure to give a liquid, b.p. 152°–163° C. (0.01 mm); $\lambda$ max.$^{MeOH}$ = 223 m$\mu$ (10700); $\nu$ max. = 1745 (ester carbonyl groups), 1725 (ketone carbonyl groups), and 1235 cm$^{-1}$ (acetoxy group).

EXAMPLE 121

Preparation of 4-hydroxy-2-(6-carboxyhexyl)cyclopent-2-en-1-one

To a stirred solution of 6.91 g. (50 mmoles) of potassium carbonate in 1400 ml. of methanol and 1400 ml. of water containing 100 mg. of hydroquinone is added 14.8 g. (50 mmoles) of 4-acetoxy-2-(6-carbethoxyhexyl)cyclopent-2-en-1-one (Example 120) during one minute at room temperature under nitrogen. The solution is stirred for 90 minutes and at this stage it contains 4-hydroxy-2-(6-carbethoxyhexyl)cyclopent-2-en-1-one. It is then treated with 23.6 g. (75 mmoles) of barium hydroxide octahydrate during one minute. The mixture is stirred for 60 minutes and then is concentrated at reduced pressure to a volume of 1800 ml. during one hour. The solution is diluted with 300 ml. of water, saturated with sodium chloride, and stirred with 400 ml. of ether while 70 ml. of 4N hydrochloric acid is added. The aqueous phase is extracted with additional ether, and the combined organic phases are washed with saturated sodium chloride solution. The extract is dried over magnesium sulfate. The crude product obtained after evaporation of the solvents is purified by chromatography on silica gel to give an oil, $\lambda$ max.$^{MeOH}$ = 223 m$\mu$ (7360); $\nu$ max. = 3380 (hydroxyl groups), 1710 (carbonyl groups), and 1632 cm$^{-1}$ (olefin group).

EXAMPLE 122

Preparation of 2-(6-carboxyhexyl)-4-hydroxy-cyclopent-2-en-1-one

To a stirred solution of 10.6 g. (ca. 34 mmoles) of crude 4-bromo-2-(6-carboxyhexyl)cyclopent-2-en-1-one (Example 93) in 100 ml. of acetone and 65 ml. of water is added 8.80 g. (45.2 mmoles) of silver fluoborate during 2 minutes. The temperature is maintained at 25°–30° C. by external cooling. The mixture is stirred for 90 minutes, filtered, saturated with sodium chloride, and extracted with ether. The extract is extracted with half saturated sodium bicarbonate solutions. The basic solutions is reacidified with dilute hydrochloric acid, saturated with sodium chloride, and extracted with ether. The extract is washed with water and saturated sodium chloride solution, dried over magnesium sulfate, and concentrated. The crude product is purified by partition chromatography on Celite to give an oil with the properties described in Example 121.

EXAMPLES 123–146

By the procedure of the preceding Example 122 the various 4-bromocyclopentenones of the following Table VI are solvolyzed in acetone-water in the presence of silver fluoborate to provide the 4-hydroxycyclopentenones of the Table.

TABLE VI

| Example | Starting cyclopentenones of Example | Product 4-hydroxycyclopente-2-en-ones |
|---|---|---|
| 123 | 94 | 4-hydroxy-2-(6-carbethoxyhexyl)-cyclopent-2-en-1-one |
| 124 | 95 | 4-hydroxy-2(6-carbomethoxyhexyl)-cyclopent-2-en-1-one |
| 125 | 96 | 4-hydroxy-2-(4-carbethoxybutyl)-cyclopent-2-en-1-one |
| 126 | 97 | 4-hydroxy-2-(3-carbethoxypropyl)-cyclopent-2-en-1-one |
| 127 | 98 | 4-hydroxy-2-(4-carboxybutyl)-cyclopent-2-en-1-one |
| 128 | 99 | 4-hydroxy-2-(3-carboxypropyl)-cyclopent-2-en-1-one |
| 129 | 101 | 4-hydroxy-2-(8-carbethoxyoctyl)-cyclopent-2-en-1-one |
| 130 | 102 | 4-hydroxy-2-(6-carboxyoctyl)-cyclopent-2-en-1-one |
| 131 | 103 | 4-hydroxy-2-(6-carbethoxyoctyl)-cyclopent-2-en-1-one |
| 132 | 104 | 4-hydroxy-2-(6-carboxy-5,5-dimethylhexyl)cyclopent-2-en-1-one |
| 133 | 105 | 4-hydroxy-2-(6-carbethoxy-5,5-dimethylhexyl)cyclopent-2-en-1-one |
| 134 | 106 | 4-hydroxy-2-(6-carboxy-5-oxahexyl)cyclopent-2-en-1-one |
| 135 | 107 | 4-hydroxy-2-(6-carbethoxy-5-oxahexyl)cyclopent-2-en-1-one |
| 136 | 108 | 4-hydroxy-2-(6-carboxy-6-fluorohexyl)cyclopent-2-en-1-one |
| 137 | 109 | 4-hydroxy-2-(6-carbethoxy-6-fluorohexyl)cyclopent-2-en-1-one |
| 138 | 110 | 4-hydroxy-2-(5-carboxypentyl)-cyclopent-2-en-1-one |
| 139 | 111 | 4-hydroxy-2-(5-carbethoxypentyl)-cyclopent-2-en-1-one |
| 140 | 112 | 4-hydroxy-2-(7-carboxyheptyl)-cyclopent-2-en-1-one |
| 141 | 113 | 4-hydroxy-2-(7-carbethoxyheptyl)-cyclopent-2-en-1-one |
| 142 | 114 | 4-hydroxy-2-(6-carboxy-6-phenylhexyl)cyclopent-2-en-1-one |
| 143 | 115 | 4-hydroxy-2-(6-carbethoxy-6-phenylhexyl)cyclopent-2-en-1-one |
| 144 | 116 | 4-hydroxy-2-(6-carbo-n-butoxyhexyl)cyclopent-2-en-1-one |
| 145 | 117 | 4-hydroxy-2-(6-carbo-isopropoxyhexyl)cyclopent-2-en-1-one |
| 146 | 118 | 4-hydroxy-2-(6-carbo-n-decyloxyhexyl)cyclopent-2-en-1-one |
| 146a | 118a | 4-hydroxy-2-(6-carboxyheptyl)-cyclopent-2-en-1-one |

EXAMPLE 147

Preparation of 4-tetrahydropyranyloxy-2-(6-tetrahydropyranylcarboxyhexyl)cylopent-2-en-1-one To a stirred solution of 5.59 g. (24.6 mmoles) of 4-hydroxy-2-(6-carboxyhexyl)cyclopent-2-en-1one (Example 122) and 20.7 g. (246 mmoles) of dihydropyran in 100 ml. of methylene chloride at 20° C. is added 47 mg. (0.246 mmoles) of p-toluenesulfonic acid monohydrate in one portion. The temperature is maintained at 20°-25° C. by cooling and is stirred for one hour at that temperature. The solution is diluted with 200 ml. of ether and poured into a mixture of 40 ml. of saturated sodium bicarbonate solution, 40 ml. of saturated sodium chloride solution, and 80 ml. of water. The phases are [seaparated] *separated*, and the aqueous phase is extracted with additional ether. The total extract is washed successively with water and saturated sodium chloride solution, dried over potassium carbonate, and freed of volatile matter by concentration at reduced pressure to give an oil, $\lambda$ max.$^{MeOH}$ = 223 m$\mu$ (9500); $\nu$ max. 1730 (ester carbonyl group), 1705 (ketone carbonyl group), and 1030 cm$^{-1}$ (tetrahydropyranyloxy groups).

EXAMPLES 148–157

By the procedure of Example 147, the various 4-hydroxycyclopentenones of Table VII, which follows, are converted to the tetrahydropyranyl 4-tetrahydropyranyloxycyclopentenone esters of the table.

TABLE VII

| Example | Starting 4-hydroxycyclopentenone of Example | Product Tetrahydropyran-2'-yl 4-tetrahydropyran-2'-yl'-oxycyclopent-2-en-1-ones |
|---|---|---|
| 148 | 127 | 4-tetrahydropyran-2'-yloxy-2-(4-carbotetrahydropyran-2-'-yloxybutyl)cyclopent-2-en-1-one |
| 149 | 128 | 4-tetrahydropyran-2'-yloxy-2-(3-carbotetrahydropyran-2'-yloxypropyl)cyclopent-2-en-1-one |
| 150 | 119 | 4-tetrahydropyran-2'-yloxy-2-(8-carbotetrahydropyran-2'-yloxyoctyl)cyclopent-2-en-1-one |
| 151 | 130 | 4-tetrahydropyran-2'-yloxy-2-(6-carbotetrahydropyran-2'-yloxyoctyl)cyclopent-2-en-1-one |
| 152 | 132 | 4-tetrahydropyran-2'-yloxy-2-(6-carbotetrahydropyran-2'-yloxy-5,5-dimethyl)-cyclopent-2-en-1-one |
| 153 | 134 | 4-tetrahydropyran-2'-yloxy-2-(6-carbotetrahydropyran-2'-yloxy-5-oxahexyl)cyclopent-2-en-1-one |
| 154 | 136 | 4-tetrahydropyran-2'-yloxy-2-(6-carbotetrahydropyran-2'-yloxy-6-fluorohexyl)cyclopent-2-en-1-one |
| 155 | 138 | 4-tetrahydropyran-2'-yloxy-2-(5-carbotetrahydropyran-2'-yloxypentyl)cyclopent-2-en-1-one |
| 156 | 140 | 4-tetrahydropyran-2'-yloxy-2-(7-carbotetrahydropyran-2'-yloxyheptyl)cyclopent-2-en-1-one |
| 157 | 142 | 4-tetrahydropyran-2'-yloxy-2-(6-carbotetrahydropyran-2'-yloxy-6-phenylhexyl)-cyclopent-2-en-1-one |
| 157a | 146a | 4-tetrahydropyran-2'-yloxy-2-(6-carbotetrahydropyran-2'-yloxyheptyl)-cyclopent-2-en-1-one |

EXAMPLE 158

Preparation of 4-tetrahydropyranyloxy-2-(6-carbethoxyhexyl)cyclopent-2-en-1-one To a stirred solution of 674 mg. (2.64 mmoles) of 4-hydroxy-2-(6-carbethoxyhexyl)cyclopent-2-en-1-one (Example 123) and 2.22 g. (26.4 mmoles) of dihydropyran in 2.6 ml. of methylene chloride is added 5.0 mg. (0.026 mmoles) of p-toluenesulfonic acid monohydrate. After stirring for 20 minutes at room temperature the solution is diluted with ether and poured into saturated sodium chloride solution containing a little sodium bicarbonate. The organic phase is separated and washed with saturated sodium chloride solution. The extract is dried over magnesium sulfate, and volatile matter is evaporated at reduced pressure to give an oil, $\lambda$ max.$^{MeOH}$ = 224 m$\mu$ (7950); $\nu$ max. = 1735 (ester carbonyl group), 1710 (ketone carbonyl group), and 1030 cm$^{-1}$ (tetrahydropyranyloxy group).

EXAMPLES 159–172

In the manner of Example 158 the alkyl 4-hydroxycyclopentenone esters of Table VIII, which follows, are converted to the corresponding 4-tetrahydropyranyloxy alkyl esters of the table.

TABLE VIII

| Example | Starting 4-hydroxycyclopentenone Esters of Example | Product 4-tetrahydropyran-2'-yloxy-cyclopent-2-en-1-one esters |
|---|---|---|
| 159 | 124 | 4-tetrahydropyran-2'-yloxy-2-(6-carbomethoxyhexyl)cyclopent-2-en-1-one |
| 160 | 125 | 4-tetrahydropyran-2'-yloxy-2-(4-carbethoxybutyl)cyclopent-2-en-1-one |
| 161 | 126 | 4-tetrahydropyran-2'-yloxy-2-(3-carbethoxypropyl)cyclopent-2-en-1-one |
| 162 | 129 | 4-tetrahydropyran-2'-yloxy-2-(8-carbethoxyoctyl)cyclopent-2-en-1-one |
| 163 | 131 | 4-tetrahydropyran-2'-yloxy-2-(6-carbethoxyoctyl)cyclopent-2-en-1-one |
| 164 | 133 | 4-tetrahydropyran-2'-yloxy-2-(6-carbethoxy-5,5-dimethylhexyl)cyclopent-2-en-1-one |
| 165 | 135 | 4-tetrahydropyran-2'-yloxy-2-(6-carbethoxy-5-oxahexyl)cyclopent-2-en-1-one |
| 166 | 137 | 4-tetrahydropyran-2'-yloxy-2-(6-carbethoxy-6-fluorohexyl)cyclopent-2-en-1-one |
| 167 | 139 | 4-tetrahydropyran-2'-yloxy-2-(5-carbethoxypentyl)cyclopent-2-en-1-one |
| 168 | 141 | 4-tetrahydropyran-2'-yloxy-2-(7-carbethoxyheptyl)cyclopent-2-en-1-one |
| 169 | 143 | 4-tetrahydropyran-2'-yloxy-2-(6-carbethoxy-6-phenylhexyl)cyclopent-2-en-1-one |
| 170 | 144 | 4-tetrahydropyran-2'-yloxy-2-(6-carbo-n-butoxyhexyl)cyclopent-2-en-1-one |
| 171 | 145 | 4-tetrahydropyran-2'-yloxy-2-(6-carbo-isopropxyhexyl)cyclopent-2-en-1-one |
| 172 | 146 | 4-tetrahydropyran-2'-yloxy-2-(6-carbo-n-decyloxyhexyl)-cyclo pent-2-en-1-one |

EXAMPLE 173

Preparation of 4-methoxy-2-(6-carboxyhexyl)cyclopent-2-en-1-one (Example 93) in 85 ml. of methanol at 0°–3° C. is added 4.40 g. (22.6 mmole) of silver fluoborate in one portion. After 2 minutes, the mixture is treated with 2.66 g. (24.8 mmoles) of 2,6-lutidine. After stirring for 30 minutes at 0°–3° C. the mixture is stirred at ambient temperature for 45 minutes. Silver bromide is removed by filtration, and the filtrate is concentrated to a volume of 40 ml. The solution is treated with saturated sodium chloride solution and extracted with ether. The extract is washed successively with 0.5N hydrochloric acid solution, water, and saturated sodium chloride solution; dried over magnesium sulfate; and concentrated. Partition chromatography of the residue on Celite gives an oil, $\lambda$ max.$^{MeOH}$ = 220 m$\mu$ (7450); $\nu$ max. = 1715 (carbonyl groups) and 1095 cm$^{-1}$ (methoxy group).

EXAMPLES 174–202

Alcoholysis with the appropriate alcohol of the 4-bromocyclopentenones listed in Table IX, directly following, in the manner of Example 173 provides the 4-alkoxycyclopentenones of the Table.

TABLE IX

| Example | Starting bromocyclopentenone of example | Product 4-alkoxycyclopent-2-en-ones |
|---|---|---|
| 174 | 94 | 4-ethoxy-2-(6-carbethoxyhexyl)-cyclopent-2-en-1-one |
| 175 | 95 | 4-methoxy-2-(6-carbomethoxyhexyl)-cyclopent-2-en-1-one |
| 176 | 96 | 4-propoxy-2-(4-carbethoxybutyl)-cyclopent-2-en-1-one |
| 177 | 97 | 4-isopropoxy-2-(3-carbethoxypropyl)cyclopent-2-en-1-one |
| 178 | 98 | 4-methoxy-2-(4-carboxybutyl)cyclopent-2-en-1-one |
| 179 | 99 | 4-ethoxy-2-(3-carboxypropyl)cyclopent-2-en-1-one |
| 180 | 100 | 4-methoxy-2-(8-carboxyoctyl)cyclopent-2-en-1-one |
| 181 | 101 | 4-isopropoxy-2-(8-carbethoxyoctyl)-cyclopent-2-en-1-one |
| 182 | 102 | 4-methoxy-2-(6-carboxyoctyl)cyclopent-2-en-1-one |
| 183 | 103 | 4-n-butoxy-2-(6-carbethoxyoctyl)-cyclopent-2-en-1-one |
| 184 | 104 | 4-methoxy-2-(6-carboxy-5,5-dimethylhexyl)cyclopent-2-en-1-one |
| 185 | 105 | 4-methoxy-2-(6-carbethoxy-5,5-dimethylhexyl)cyclopent-2-en-1-one |
| 186 | 106 | 4-methoxy-2-(6-carboxy-5-oxahexyl)-cyclopent-2-en-1-one |
| 187 | 107 | 4-ethoxy-2-(6-carbethoxy-5-oxahexyl)cyclopent-2-en-1-one |
| 188 | 108 | 4-methoxy-2-(6-carboxy-6-fluorohexyl)cyclopent-2-en-1-one |
| 189 | 109 | 4-propoxy-2-(6-carbethoxy-6-fluorohexyl)cyclopent-2-en-1-one |
| 190 | 110 | 4-methoxy-2-(5-carboxypentyl)cyclopent-2-en-1-one |
| 191 | 111 | 4-sec-butoxy-2-(5-carbethoxypentyl)-cyclopent-2-en-1-one |
| 192 | 112 | 4-methoxy-2-(7-carboxyheptyl)-cyclopent-2-en-1-one |
| 193 | 113 | 4-methoxy-2-(7-carbethoxyheptyl)-cyclopent-2-en-1-one |
| 194 | 114 | 4-methoxy-2-(6-carboxy-6-phenylhexyl)cyclopent-2-en-1-one |
| 195 | 115 | 4-ethoxy-2-(6-carbethoxy-6-phenylhexyl)cyclopent-2-en-1-one |
| 196 | 116 | 4-methoxy-2-(6-carbo-n-butoxyhexyl)cyclopent-2-en-1-one |
| 197 | 117 | 4-methoxy-2-(6-carbo-isopropoxyhexyl)cyclopent-2-en-1-one |
| 198 | 118 | 1-methoxy-2-(6-carbo-n-decyloxyhexyl)cyclopent-2-en-1-one |
| 199 | 93 | 4-ethoxy-2-(6-carboxyhexyl)cyclopent-2-en-1-one |
| 200 | 93 | 4-propoxy-2-(6-carboxyhexyl)cyclopent-2-en-1-one |
| 201 | 93 | 4-isopropoxy-2-(6-carboxyhexyl)-cyclopent-2-en-1-one |
| 202 | 93 | 4-n-butoxy-2-(6-carboxyhexyl)-cyclopent-2-en-1-one |

EXAMPLE 203

Preparation of 4-tert-butoxy-2-(6-carbethoxyhexyl)cyclopent-2-en-1-one

A stirred mixture of 6.35 g. (20 mmoles) of 4-bromo-2-(carbethoxyhexyl)cyclopent-2-en-1-one (Example 94), 3.01 g. (11 moles) of silver carbonate, and 40 ml. of t-butanol is heated at 70° C. for 17 hours. The mixture is cooled and filtered. After evaporation of t-butanol the residue is treated with aq. sodium chloride and extracted with 3:1 ether-hexane. The extract is washed with saturated sodium chloride solution, dried over magnesium sulfate, and concentrated. The crude product is purified by chromatography on silica gel to give, in order of elution; the subject compound as an oil; $\lambda$ max.$^{MeOH}$ = 219 m$\mu$ (8860); $\nu$ max. = 1735 (ester carbonyl group), 1725 ketone carbonyl group), and 1365 cm$^{-1}$(tert.-butyl group); and 4-hydroxy-2-(6-carbethoxyhexyl)cyclopent-2-en-1-one also as an oil.

EXAMPLE 204

Preparation of 4-(2-hydroxyethyoxy)-2-(6-carboxyhexyl)cyclopent-2-en-1-one

To a stirred solution of 19.1 g. of crude 4-bromo-2-(6-carboxyhexyl)cyclopent-2-en-1-one (Example 93) in 310 ml. of ethylene glycol is added 15.6 g. (80 mmole) of silver fluoborate during 2 minutes. The exothermic reaction is controlled to give a temperature of 29° C., and after 1 minute the mixture is treated during 1 minute with 8.6 g. (80 mmole) of 2,6-lutidine. The mixture is stirred at ambient temperature for 2 hours, diluted with water, and filtered. The filtrate is diluted with saturated sodium chloride solution and extracted with ether. The extract is washed with half-saturated sodium chloride solution containing a little hydrochloric acid and saturated sodium chloride solution. The extract is dried over magnesium sulfate and concentrated. Column chromatograph of the residue on silica gel gives an oil, $\lambda$ max$^{MeOH}$ = 216 m$\mu$ (8350); $\nu$ max = 3340 (hydroxyl groups), 1700 (carbonyl groups), and 1620 cm$^{-1}$ (olefin group).

EXAMPLES 205–228

By the procedure described in Example 204 the various 4-bromocyclopentenones listed in Table X, which follows, are converted, to the corresponding 4($\omega$-hydroxyalkyl)cyclopentenones of the table.

TABLE X

| Example | Starting 4-bromo-cyclopentenene of example | Product 4-($\omega$-hydroxyalkoxy)cyclopent-2-en-1-ones |
|---|---|---|
| 205 | 94 | 4-$\beta$-hydroxyethoxy-2-(6-carbethoxyhexyl)cyclopent-2-en-1-one |
| 206 | 95 | 4-$\beta$-hydroxyethoxy-2-(6-carbomethoxyhexyl)cyclopent-2-en-1-one |
| 207 | 96 | 4-$\mu$-hydroxypropoxy-2-(4-oarbethoxybutyl(cyclopent-2-en-1-one |
| 208 | 97 | 4-$\beta$-hydroxyethoxy-2-(3-carbethoxypropyl(cyclopent-2-en-1-one |
| 209 | 98 | 4-$\beta$-hydroxyethoxy-2-(4-carboxybutyl(cyclopent-2-en-1-one |
| 210 | 99 | 4-$\beta$-hydroxyethoxy-2-(3-carboxypropyl)cyclopent-2-en-1-one |
| 211 | 100 | 4-$\beta$hydroxyethoxy-2-(8-carboxyoctyl)cyclopent-2-en-1-one |
| 212 | 101 | 4-$\beta$-hydroxyethoxy-2-(8-oarbethoxyoctyl)cyclopent-2-en-1-one |
| 213 | 102 | 4-$\beta$-hydroxyethoxy-2-(6-oarboxyoctyl)cyclopent-2-en-1-one |
| 214 | 103 | 4-$\gamma$-hydroxypropoxy-2-(6-carbethoxyoctyl)cyclopent-2-en-1-one |
| 215 | 104 | 4-$\beta$-hydroxyethoxy-2-(6-carboxy-5,5-dimethylhexyl)cyclopent-2-en-1-one |
| 216 | 105 | 4-$\beta$-hydroxyethoxy-2-(6-carbethoxy-5,5,-dimethylhexyl)-cyclopent-2-en-1-one |
| 217 | 106 | 4-$\beta$-hydroxyethoxy-2-(6-carboxy-5-oxahexyl)cyclopent-2-en-1-one |
| 218 | 107 | 4$\gamma$-hydroxypropoxy-2-(6-carbethoxy-5-oxahexyl)cyclopent-2-en-1-one |
| 219 | 108 | 4-$\beta$-hydroxyethoxy-2-(6-carboxy-6-fluorohexyl)cyclopent-2-en-1-one |
| 230 | 109 | 4-$\beta$-hydroxyethoxy-2-(6-carbethoxy-6-fluorohexyl)cyclopent-2-en-1-one |
| 221 | 110 | 4-$\beta$-hydroxyethoxy-2-(5-carboxypentyl)cyclopent-2-en-1-one |
| 222 | 112 | 4-$\beta$-hydroxyethoxy-2-(7-carboxyheptyl)cyclopent-2-en-1-one |
| 223 | 114 | 4-$\beta$-hydroxyethoxy-2-(6-carboxy-6-phenylhexyl)cyclopent-2-en-1-one |
| 224 | 115 | 4-$\beta$-hydroxyethoxy-2-(6-carbethoxy-6-phenylhexyl)cyclopent-2-en-1-one |
| 225 | 116 | 4-$\beta$-hydroxyethoxy-2-(6-carbon-butoxyhexyl)cyclopent-2-en-1-one |
| 236 | 117 | 4-$\beta$-hydroxyethoxy-2-(carboisopropoxyhexyl)cyclopent-2-en-1-one |
| 227 | 118 | 4-$\beta$-hydroxyethoxy-2-(6-carbon-decyloxyhexyl)cyclopent-2-en-1-one |
| 228 | 93 | 4-$\beta$-hydroxypropoxy-2-(6-carboxyhexyl)cyclopent-2-en-1-one |

EXAMPLES 229–242

By the procedure described in Example 147 the 4-alkoxycyclopentenone carboxylic [acis] *acids* listed in Table XI were converted to the corresponding tetrahydropyran-2'-yl esters of the table.

TABLE XI

| Example | Starting 4 alkoxy-cyclopentenone carboxylic acid of example | Product Tetrahydropyran-2'yl ester 4-alkocycyclopent-1-ones |
|---|---|---|
| 229 | 178 | 4-methoxy-2-(4-carbotetrahydropyran-2'yloxybutyl)-cyclopent-2-en-1-one |
| 230 | 179 | 4-ethoxy-2-(3-carbotetrahydropyran-2'yloxypropyl)-cyclopent-2-en-1-one |
| 231 | 180 | 4-methoxy-2-(8-carbotetrahydropyran-2'yloxyoctyl)-cyclopent-2-en-1-one |
| 232 | 182 | 4-methoxy-2-(6-carbotetrahydropyran-2'-yloxyoctyl)-cyclopent-2-en-1-one |
| 233 | 184 | 4-methoxy-2-(6-carbotetrahydropyran-2'-yloxy-5,5-dimethylhexyl)cyclopent-2-en-1-one |
| 234 | 186 | 4-methoxy-2-(6-carbotetrahydroxypyran-2'-yloxy-5-oxahexyl)cyclopent-2-en-1-one |
| 235 | 188 | 4-methoxy-2-(6-carbotetrahydropyran-2'-yloxy-6-fluorohexyl)-cyclopent-2-en-1-one |
| 236 | 190 | 4-methoxy-2-(5-carbotetrahydropyran-2'-yloxy-pentyl)-cyclopent-2-en-1-one |
| 237 | 192 | 4-methoxy-2-(7-carbotetrahydropyran-2'-yloxyheptyl)-cyclopent-2-en-1-one |
| 238 | 194 | 4-methoxy-2-(6-carbotetrahydropyran-2'-yloxy-6-phenylhexyl)-cyclopent-2-en-1-one |
| 239 | 199 | 4-ethoxy-2-(6-carbotetrahydropyran-2'-yloxyhexyl)cyclopent-2-en-1-one |
| 240 | 200 | 4-propoxy-2-(6-carbotetrahydropyran-2'-yloxyhexyl)cyclopent-2-en-1-one |
| 241 | 201 | 4-isopropoxy-2-(6-carbotetra- |

TABLE XI-continued

| Example | Starting 4 alkoxy-cyclopentenone carboxylic acid of example | Product Tetrahydropyran-2'yl ester 4-alkocyclopent-1-ones |
|---|---|---|
| | | hydropyran-2'-yloxyhexyl)cyclopent-2-en-1-one |
| 242 | 202 | 4-n-butoxy-2-(6-carbotetrahydropyran-2'-yloxyhexyl)cyclopent-2-en-1-one |
| 242a | 173 | 4-methoxy-2-(6-carbotetrahydropyran-2'-yloxyhexyl)cyclopent-2-en-1-one |

EXAMPLES 243–266

Treatment of the 4-(ω-hydroxyalkoxy)cyclopentenones of Table XII below with dihydropyran in the manner of Example 147 provides the 4-(ω-tetrahydropyranyloxyalkoxy)-cyclopentenone esters listed in the table.

TABLE XII

| Example | Starting 4-(ω-hydroxyalkoxy)-cyclopentenone of example | Product 4-(ω-tetrahydropyran-2'-yloxy-alkoxy)-cyclopent-2-en-1-one esters |
|---|---|---|
| 243 | 205 | 4-β-tetrahydropyrany-2'-yloxy-ethoxy-2-(6-carbethoxyhexyl)-cyclopent-2-en-1-one |
| 244 | 206 | 4-β-tetrahydropyrany-2'-yloxy-ethoxy-2-(6-carbomethoxyhexyl)-cyclopent-2-en-1-one |
| 245 | 207 | 4-γ-tetrahydropyran-2'-yloxy-propoxy-2-(4-carbethoxybutyl)-cyclopent-2-en-1-one |
| 246 | 208 | 4-β-tetrahydropyran-2'-yloxy-ethoxy-2-(3-carbethoxypropyl)-cyclopent-2-en-1-one |
| 247 | 204 | 4-β-tetrahydropyran-2'-yloxy-ethoxy-2-(6-carbotetrahydropyran-2'-yloxyhexyl)cyclopent-2-en-1-one |
| 248 | 209 | 4-β-tetrahydropyran-2'-yloxy-ethoxy-2-(4-carbotetrahydropyran-2'-yloxybutyl)cyclopent-2-en-1-one |
| 249 | 210 | 4-β-tetrahydropyran-2'-yloxy-ethoxy-2-(3-carbotetrahydropyran-2'-yloxypropyl)cyclopent-2-en-1-one |
| 250 | 212 | 4-β-tetrahydropyran-2'-yloxy-ethoxy-2-(8-carbethoxyoctyl)-cyclopent-2-en-1-one |
| 251 | 211 | 4-β-tetrahydropyran-2'-yloxy-ethoxy-2-(8-carbotetrahydropyran-2'-yloxyoctyl)cyclopent-2-en-1-one |
| 252 | 213 | 4-β-tetrahydropyran-2'-yloxy-ethoxy-2-(6-carbotetrahydropyran-2'-yloxyoctyl)cyclopent-2-en-1-one |
| 253 | 214 | 4-γ-tetrahydropyran-2'-yloxy-propoxy-2-(6-carbethoxyoctyl)-cyclopent-2-en-1-one |
| 254 | 215 | 4-β-tetrahydropyran-2'-yloxy-ethoxy-2-(6-carbotetrahydropyran-2'-yloxy-5,5-dimethylhexyl)cyclopent-2-en-1-one |
| 255 | 216 | 4-β-tetrahydropyran-2'-yloxy-ethoxy-2-(6-carbethoxy-5,5-dmethylhexyl)cyclopent-2-en-1-one |
| 256 | 217 | 4-β-tetrahydropyran-2'-yloxy-ethoxy-2-(6-carbotetrahydropyran-2-yloxy-5-oxahexyl)cyclopent-2-en-1-one |
| 257 | 218 | 4-γ-tetrahydropyran-2'-yloxy-propoxy-2-(6-carbethoxy-5-oxahexyl(cyclopent-2-en-1-one |
| 258 | 219 | 4-β-tetrahydropyran-2'-yloxy-ethoxy-2-(6-carbotetrahydropyran-2'-yloxy-6-fluorohexyl)-cyclopent-2-en-1-one |
| 259 | 220 | 4-β-tetrahydropyran-2'-yloxy-ethoxy-2-(6-carbethoxy-6-fluorohexyl)cyclopent-2-en-1-one |
| 260 | 221 | 4-β-tetrahydropyran-2'-yloxy-ethoxy-2-(5-carbotetrahydropyran-2'-yloxpentyl(cyclopent-2-en-1-one |
| 261 | 222 | 4-β-tetrahydropyran-2'-yloxy-ethoxy-2-(7-carbotetrahydropyran-2'-yloxheptyl)cyclopent-2-en-1-one |
| 262 | 223 | 4-β-tetrahydropyran-2'-yloxy-ethoxy-2-(6-carbotetrahydropyran-2'-yloxy-6-phenylhexyl)-cyclopent-2-en-1-one |
| 263 | 224 | 4-β-tetrahydropyran-2'-yloxy-ethoxy-2-(6-carbethoxy-6-phenylhexyl)cyclopent-2-en-1-one |
| 264 | 225 | 4-β-tetrahydropyran-2'-yloxy-ethoxy-2-(6-carbo-n-butoxyhexyl)cyclopent-2-en-1-one |
| 265 | 226 | 4-β-tetrahydropyran-2'-yloxy-ethoxy-2-(6-carbo-isopropoxyhexyl)cyclopent-2-en-1-one |
| 266 | 227 | 4-β-tetrahydropyran-2'-yloxy-ethoxy-2-(6-carbo-n-decyloxyhexyl)cyclopent-2-en-1-one |
| 267 | 228 | 4-β-tetrahydropyran-2'-yloxy-propoxy-2-(6-carbotetrahydropyran-2'-yloxhexyl)cyclopent-2-en-1-one |

EXAMPLE 268

Preparation of 4-(4-hydroxybutoxy)-2-(6-carboxyhexyl)-cyclopent-2-en-1-one

To a stirred solution of 56.0 g. of crude 4-bromo-2-(6-carboxyhexyl)cyclopent-2-en-1-one (Example 93) in 400 ml. of tetrahydrofuran and 133 ml. of water at 3° C. is added 44.1 g. (0.226 moles) of silver fluoborate during 25 minutes. The mixture is stirred at 0°–5° C. for 60 minutes, diluted with water and ether, and filtered. The aqueous portion of the filtrate is saturated with solid sodium chloride and extracted with additional ether. The combined organic phases and washed successively with water and saturated sodium chloride solution, dried over magnesium sulfate, and concentrated. Column chromatography of the residue gives the subject compound as a mixture with 4-hydroxy-2-(6-carboxyhexyl)cyclopent-2-en-1-one. NMR ($CDCl_3$) 3.60 (multiplet, O-methylene hydrogens) and 4.60 f (multiplet, O-methine hydrogen).

EXAMPLE 269

Preparation of 4-(4-tetrahydropyranyloxybutoxy)-2-(6-tetrahydropyranylcarboxyhexyl)cyclopent-2-en-1-one In the manner of Example 147 the mixture of 4-hydroxy-2-(6-carboxyhexyl)cyclopent-2-en-1-one and 4-(4-hydroxybutoxy)-2-(6-carboxyhexyl)cyclopent-2-en-1-one (Example 268) is converted to a mixture of the subject compound and 4-tetrahydropyranyloxy-2-(6-tetrahydropyranylcarboxyhexyl)cyclopent-2-en-1-one with dihydropyran and p-toluenesulfonic acid monohydrate in methylene chloride.

EXAMPLE 270

Preparation of 2-(6,6-dicarbethoxyheptyl)-2-cyclopentenone methoxime

The subject compound is prepared from sodio diethyl methylmalonate and 2-(5-methanesulfonyloxypentyl)-2-cyclopentenone methoxime (Example 60) by the procedure described in Example 61.

EXAMPLE 271

Preparation of 2-(6-carboxyheptyl)-2-cyclopentenone methoxime

Saponification of 2-(6,6-dicarbethoxyheptyl)-2-cyclopentenone methoxime (Example 270) with potassium hydroxide by the method of Example 20 is productive of 2-(6,6-dicarboxyheptyl)-2-cyclopentenone methoxime, decarboxylation of which in the manner of Example 63 provides the subject compound.

EXAMPLE 272

Preparation of 2-(6-carboxyheptyl)-2-cyclopentenone

Methoxime cleavage of 2-(6-carboxyheptyl)-2 (Example 271) in the manner of Example 22 provides the subject ketone.

EXAMPLE 273

Preparation of 2-(6-carbethoxyheptyl)-2-cyclopentenone

Esterification with ethanol of the acid chloride derived from 2-(6-carboxyheptyl)-2-cyclopentenone in the manner of Example 31 is productive of the subject compound.

EXAMPLE 274

Preparation of 2-(6-carbethoxy-5-thiahexyl)-1-methoximino-2-cyclopentene

To a stirred mixture of 1.465 g. (0.0348 mole) of sodium hydride (57.2% in mineral oil) in 50 ml. of dimethoxyethane, under nitrogen, is added slowly 4.8 g. (0.0347 mole) of ethyl-2-mercaptoacetate. The reaction mixture is stirred at room temperature for one hour and then a solution of 7.8 g. (0.0231 mole) of 2-(4p-toluenesulfonyloxybutyl)-1-methoximino-2-cyclopentene in 30 ml. of dimethoxyethane is added dropwise and stirred at room temperature for 18 hours. The solution is heated at reflux for 1 hour, cooled and poured into cold dilute hydrochloric acid and then extracted with ether. The combined ether extracts are washed with saline, dried over magnesium sulfate and evaporated to give 7.6 g. of subject product as a yellow oil.

EXAMPLE 275

Preparation of 2-(6-carboxy-5-thiahexyl)-2-cyclopentenone

In the manner described in Example 22, treatment of 2-(6-carbethoxy-5-thiahexyl)-1-methoximino-2-cyclopentene with acetone and 2N hydrochloric acid at reflux gives the subject product as a yellow oil.

EXAMPLE 276

Preparation of 2-(6-carbethoxy-5-thiahexyl)-2-cyclopentenone

In the manner described in Example 23, treatment of 2-(6-carboxy-5-thiahexyl)-2-cyclopentenone with p-toluenesulfonic acid in ethanol gives the subject ester as a yellow oil.

EXAMPLE 277

Preparation of 1-triphenylmethoxy-5-hexyne

A stirred mixture of 9.81 g. (0.10 moles) of 5-hexyn-1-ol, 33.5 g. (0.12 moles) of triphenylmethyl chloride, and 200 ml. of dry pyridine is refluxed for 60 minutes. The cooled mixture is poured into water and extracted with ether. The extract is washed successively with water, ice-cold N hydrochloric acid, water, saturated sodium bicarbonate solution, and saturated sodium chloride solution. The extract is dried with magnesium sulfate. The crude product obtained after evaporation of the solvent is purified by chromatography on Florisil to give an oil, $\nu$ max. 3290 (acetylenic hydrogen), 1600, 1072, and 705 $cm^{-1}$ (triphenylmethoxy group).

EXAMPLE 278

Preparation of 4-triphenylmethoxy-1-octyne

A mixture of 10 g. (0.08 moles) of 4-hydroxy-1-octyne [L. Crombie and A. G. Jacklin, J. Chem. Soc., 1632 (1957)] and 30.75 g. (0.09 moles) of triphenylmethyl bromide in 85 ml. of dry pyridine is heated on the steam bath for 2 hours. The cooled mixture is treated with water and extracted with ether. The extract is washed successively with ice cold 2% hydrochloric acid, saturated sodium chloride solution, dried with magnesium sulfate, and taken to dryness. Column chromatography of the residue on Florisil affords an oil; $\lambda$ max 3.01, 4.72 (acetylenic hydrogen), 6.28, 9.65 and 14.25 m$\mu$ (triphenylmethoxy group).

EXAMPLE 279

Preparation of 4-triphenylmethoxy-1hexyne

A stirred solution of 9.81 g. (0.10 moles) of 4-hydroxy-1hexyne and 33.5 g. (0.12 moles) of triphenylmethyl chloride in 100 ml. of dry pyridine is heated at reflux for 2 hours. The cooled mixture is treated with water and extracted with a hexane-ether mixture. The extract is washed successively with water and saturated sodium chloride solution, dried over magnesium sulfate, and concentrated. Column chromatography of the residue on Florisil gives an oil, $\nu$ max. 3290 (acetylenic hydrogen), 1600, 1030, and 705 $cm^{-1}$ (triphenylmethoxy group).

EXAMPLE 280

Preparation of Tetrahydropyran-2-yl-9-oxo-11$\alpha$-tetrahydropyranyloxy-20-triphenylmethoxy-8$\xi$-13-trans-prostenoate In the manner described in Example 281, 36.8 g. (100 mmoles) of 8-triphenylmethoxy-1-octyne (Example 304) contained in 50 ml. of benzene is converted to an alanate reagent by treatment with 83.5 ml. of 1.2 M diisobutylaluminum hydride in hexane and 45 ml. of 2.2 M methyl lithium in ether. To the stirred reagent is added 80 mmoles of crude 2-(6-tetrahydropyranylcarboxyhexyl)-4-tetrahydropyranyloxycyclopent-2-en-1-one (Example 147) in 40 ml. of ether at 5°–10° during 10 minutes. The mixture is stirred at ice temperature for 1 hour and at ambient temperature for 15 hours. The mixture is diluted with ether and poured into a stirred mixture of ice and hydrochloric acid. The organic phase is separated, and the aqueous phase is extracted with ether. The combined extracts are washed with cold N HCl, water, and saturated sodium chloride solution. The extract is dried over magnesium sulfate, and the solvents are evaporated at reduced pressure to give the crude product as an oil, $\nu$ max, 1730 (carbonyl groups), 1035 (tetrahydropyranyloxy groups), 975 (trans vinyl group), and 705 $cm^{-1}$ (triphenylmethoxy group).

EXAMPLE 280 a

Preparation of
11α,20-dihydroxy-9-oxo-13-trans-prostenoic acid

A 0.05 M solution of crude tetrahydropyran-2-yl-9-oxy-11-tetrahydropyranyloxy-20-triphenylmethoxy-8ξ-13-trans-prostenoate (Example 280) in glacial acetic acid-tetrahydrofuran-water (4:2:1) is heated at 45° for 7 hours. The solution is diluted with aqueous sodium chloride solution and extracted with ether. The extract is washed with water and concentrated using toluene for azeotropic removal of aqueous acetic acid. The residue is purified by column chromatography on silica gel to give an oil ν max, 1735 (ketone carbonyl group), 1710 (acid carbonyl group), and 967 $cm^{-1}$ (transvinyl group).

EXAMPLE 281

Preparation of ethyl
20-triphenylmethoxy-9-oxo-18,19-dinor-8-13-trans-prostenoate A stirred solution of 16.35 g. (48.0 mmoles) of 1-triphenylmethoxy-5-hexyne (Example 277) in 24 ml. of benzene is treated with 40 ml. of 1.2 M diisobutylaluminum hydride in hexane, and the resulting solution is heated at 50° for 2 hours. The solution is cooled, diluted with 35 ml. of ether, and treated at 3°-10° with 27.5 ml. of 1.6 M n-butyl lithium in hexane. After 20 minutes at ambient temperature the alanate solution is cooled to 0° and treated with a solution of 9.53 g. (40 mmoles) of 2-(6-carbethoxyhexyl)-cyclopent-2-en-1-one (Example 13), in 10 ml. of ether. The reaction mixture is stirred at ambient temperature for 18 hours, diluted with ether, and poured into a stirred mixture of ice and 4N hydrochloric acid. The mixture is stirred for 1 hour at ambient temperature, and the ether phase is separated, washed successively with water and saturated sodium chloride solution, and dried over magnesium sulfate. The residue obtained after evaporation of the solvent is purified by chromatography on silica gel to give an oil, ν max. 1735 (carbonyl groups), 968 (trans vinyl group), and 705 $cm^{-1}$ (triphenylmethoxy group).

EXAMPLE 282

Preparation of ethyl
20-hydroxy-9-oxo-18,19-dinor-13trans-prostenoate

A 0.05 M solution of ethyl 20-triphenyl-methoxy-9-oxo-18,19-dinor-13-trans-prostenoate (Example 281) in glacial acetic acid-tetrahydrofuran-water (4:2:1) is heated at 45° for 9 hours. The residue obtained after evaporation of the solvent is purified by chromatography on silica gel to give an oil, ν max. 3450 (hydroxyl group), 1735 (carbonyl groups), and 967 $cm^{-1}$ (trans vinyl group).

EXAMPLE 283

Preparation of
20-hydroxy-9-oxo-18,19-dinor-13-trans-prostenoic acid

A solution of 2.54 g. (7.5 mmoles) of ethyl 20-hydroxy-9-oxo-18,19-dinor-13-trans-prostenoate (Example 282), 1.49 g. (22.5 mmoles) of 85% potassium hydroxide, 45 ml. of water is allowed to stand at room temperature for 20 hours. The solution is concentrated, diluted with water, extracted with ether, acidified with 4N hydrochloric acid, and extracted with ether. The final extract is washed successively with water and saturated sodium chloride solution, dried over magnesium sulfate, and concentrated to give an oil, ν max. 1735 (ketone carbonyl group), 1710 (acid carbonyl group), and 967 $cm^{-1}$ (trans vinyl group).

EXAMPLE 284

Preparation of ethyl
16-triphenylmethoxy-9-oxo-8ξ-13-trans-prostenoate

Treatment of the alanate solution, prepared by the addition of 24 ml. (0.05 moles) of 2.1 M methyl lithium in ether to a solution of 18.4 g. (0.05 moles) of 4-triphenylmethoxy-1-octyne (Example 278) in 25 ml. of dry benzene treated with 34.6 ml. (0.05 moles) of 1.45 M diisobutyl aluminum hydride in benzene, with 9.5 g. (0.04 moles) of 2-(6-carbethoxyhexyl)-cyclopent-2-en-1one (Example 13) according to the procedure, except for chromatography, described in Example 281 gave 27.65 g. of oily material; λ max. 5.78 (carbonyl groups), 10.25 (trans vinyl group), and 14.20 (triphenyl-methoxy group).

EXAMPLE 285

Preparation of ethyl
16-hydroxy-9-oxo-13-trans-prostenoate

A solution of 26.65 g. of ethyl 16-triphenylmethoxy-9-oxo-8ξ-13-trans-prostenoate (Example 284) in glacial acetic acid-tetrahydrofuran-water (4:2:1) is heated at 45° C for 3.5 hours. The residue obtained after evaporation of the solvent is partially purified by chromatography on silica gel. Total purification by partition chromatography affords an oil; ν max. 2.88 (hydroxyl group), 5.77 (carbonyl group), and 10.25 (trans vinyl group).

EXAMPLE 286

Preparation of 16-hydroxy-9-oxo-13-trans-prostenoic acid

Treatment of 3.2 g. of ethyl 16-hydroxy-9-oxo-13-trans-prostenoate (Example 285) in 50 ml. of methanol water (1:1) containing 1.37 g. of potassium hydroxide according to the procedure described in Example 283 gives 2.76 g. of oil; 5.80 (carbonyl groups) and 10.25 M (trans vinyl group).

EXAMPLES 287-303

The triphenylmethoxy substituted 1-alkynes listed in the table below are prepared by the method of Example 278 from triphenylmethyl bromide and the corresponding hydroxy substituted 1-alkynes, appropriate literature references to which are provided in the table.

TABLE 13

| Example | Reference to starting hydroxy substituted 1-alkyne | Product triphenylmethoxy substituted 1-alkyne |
|---|---|---|
| 287 | Reference 1 | 4-triphenylmethoxy-1-pentyne |
| 288 | Reference 1 | 4-triphenylmethoxy-1-heptyne |
| 289 | Reference 1 | 4-triphenylmethoxy-5-methyl-1-hexyne |
| 290 | Reference 2 | 4-triphenylmethoxy-1-nonyne |
| 291 | Reference 3 | 4-triphenylmethoxy-1-decyne |
| 292 | Reference 4 | 5-triphenylmethoxy-1-pentyne |
| 293 | Reference 5 | 7-triphenylmethoxy-1-heptyne |
| 294 | Reference 6 | 9-triphenylmethoxy-1-nonyne |
| 295 | Reference 7 | 10-triphenylmethoxy-1-decyne |
| 296 | Reference 8 | 11-triphenylmethoxy-1-undecyne |
| 297 | Reference 9 | 5-triphenylmethoxy-1-hexyne |
| 298 | Reference 10 | 4-triphenylmethoxy-7-methyl- |

TABLE 13-continued

| Example | Reference to starting hydroxy substituted 1-alkyne | Product triphenylmethoxy substituted 1-alkyne |
|---|---|---|
| | | 1-octyne |
| 299 | Reference 10 | 4-triphenylmethoxy-5-ethyl-1-heptyne |
| 300 | Reference 11 | 5-triphenylmethoxy-4-methyl-1-pentyne |
| 301 | Reference 11 | 5-triphenylmethoxy-4-ethyl-1-pentyne |
| 302 | Reference 11 | 5-triphenylmethoxy-4-methyl-1-hexyne |
| 303 | Reference 11 | 5-triphenylmethoxy-4-ethyl-1-hexyne |

References:

1. G. Fontaine et al., Bull. Soc. Chem. France, 1447 (1963).
2. S. Abe and K. Sato, Bull. Chem. Soc. Japan, 29, 88 (1956); Chem. Abstr., 50, 13737 (1956).
3. L. Crombie and A. G. Jacklin, J. Chem. Soc., 1622 (1957); 1740 (1955).
4. R. Paul and S. Tehelitcheff, Compt, rend., 232, 2230 (1951).
5. C. Crisan, Ann. Chim (Paris), [13] 1, 436 (1956).
6. R. Riemschneider, G. Kasang, and C. Boehme, Montashefte Chem., 96, 1766 (1965).
7. Ames, J. Chem. Soc. (C), 1556 (1967).
8. L. D. Bergel' son et al., Zh. Obschei Khim., 32, 58 (1962); Chem. Abstr., 57, 14930a (1962).
9. N. V. Egorov and A. S. Atavin, Chem. Abstr., 71, 61473u (1969).
10. Nobuharra Akio, Agr. Biol. Chem. (Tokyo), 32, 1016 (1968); Chem. Abstr., 70, 3219j (1969).
11. J. Colonge and R. Gelin, Bull. Soc. Chem., France, 799 (1954).

EXAMPLE 304

Preparation of 8-triphenylmethoxy-1octyne

To a stirred suspension of 68.1 g. (0.18 moles) of 1-chloro-6-triphenymethoxyhexane, prepared from 1-chloro-6-hydroxyhexane and triphenylmethyl chloride in the manner of Example 277, in 60 ml. of dimethylsulfoxide is added a solution of 19.9 g. (0.216 moles) of lithium acetylideethylenediamine complex in 120 ml. of dimethylsulfoxide during 20 minutes. The temperature is maintained at 25° C. with an ice bath during the addition, after which the mixture is stirred at ambient temperature for 3.5 hours and then at 30° C. for 15 minutes. The mixture is diluted with 100 ml. of ether and treated dropwise with 150 ml. of water with ice bath cooling. The mixture is diluted with 400 ml. of water and 250 ml. of 2:1 ether-pet ether and acidified with 120 ml. of 4N hydrochloric acid in the ice bath. The phases are separated, and the aqueous phase is extracted with 3:1 ether-pet ether. The combined extracts are washed successively with water and saturated sodium chloride solution, dried over magnesium sulfate, and concentrated. Column chromatography of the residue on Florisil affords the subject compound as white crystals, m.p. 43°-45° C. after recrystallization from pet-ether, $\nu$ max 3300 (acetylenic hydrogen), 2360 (triple bond), 1600, 1068, and 706 $cm^{-1}$ (triphenylmethoxy group).

EXAMPLES 305-450

Conjugate addition of the alanates obtained by treatment of the triphenylmethoxy (trityloxy)-1-alkyne (indicated in the following table) with diisobutylaluminum hydride followed by methyl lithium, to the cyclopentenones of the table according to the method described in Example 280 followed by de-O-tritylation of the intermediate triphenylmethoxyprostenoates according to the method of Example 280a is productive of the prostenoic acids and esters of the table.

Those compounds isolated and identified in the table as prostenoic acids are prepared via the corresponding tetrahydropyran-2-yl esters and these compounds bearing a free hydroxy function at the 11$\alpha$-position or as part of an 11$\alpha$-($\omega$-hydroxyalkoxy) moiety are prepared via the corresponding tetrahydropyran-2-yl ethers. The hydroxy function in the $\beta$-side chain (that portion of the molecule deriving from the triphenylmethoxy-1-alkyne) of all compounds in the table are initially present in the molecule as the corresponding triphenylmethyl ethers. During the acetic acid treatment (de-O-tritylation step) the triphenylmethyl ether as well as the tetrahydropyran-2-yl ethers and esters functions are hydrolyzed to provide the corresponding free hydroxy and carboxylic acid groups of the compounds listed in the table.

TABLE 14

| Example | Starting cyclopentenone of Example | Starting trityloxy-1-alkyne of Example | Product Hydroxy Prostenoic Acid or Ester |
|---|---|---|---|
| 305 | 13 | 304 | Ethyl 9-oxo-20-hydroxy-13-trans-prostenoate |
| 306 | 13 | 288 | Ethyl 9-oxo-16-hydroxy-20-nor-13-trans-prostenoate |
| 307 | 13 | 290 | Ethyl 9-oxo-16-hydroxy-20-methyl-13-trans-prostenoate |
| 308 | 13 | 297 | Ethyl 9-oxo-17-hydroxy-19,20-dinor-13-trans-prostenoate |
| 309 | 13 | 294 | Ethyl 9-oxo-20-hydroxymethyl-13-trans-prostenoate |
| 310 | 81 | 298 | Butyl 9-oxo-16-hydroxy-19-methyl-13-trans-prostenoate |
| 311 | 82 | 303 | Isopropyl 9-oxo-17-hydroxy-16-ethyl-13-trans-prostenoate |
| 312 | 83 | 296 | Methyl 9-oxo-20-(3-hydroxypropyl)-13-trans-prostenoate |
| 313 | 84 | 278 | Decyl 9-oxo-16-hydroxy-13-trans-prostenoate |
| 314 | 14 | 295 | Ethyl 5,6,7-trinor-9-oxo-20-(2-hydroxyethyl)-13-trans-prostenoate |
| 315 | 23 | 278 | Ethyl 7a,7b-bishomo-9-oxo-16-hydroxy-13-trans-prostenoate |
| 316 | 23 | 279 | Ethyl 7a,7b-bishomo-9-oxo-19,20-dinor-16-hydroxy-13-trans-prostenoate |
| 317 | 41 | 291 | Ethyl 3,3-dimethyl-9-oxo-16-hydroxy-20-ethyl-13-trans-prostenoate |
| 318 | 46 | 278 | Ethyl 3-oxo-9-oxo-16-hydroxy-13-trans-prostenoate |
| 319 | 46 | 293 | Ethyl 3-oxa-9-oxo-19-hydroxy-20-nor-13 trans-prostenoate |

TABLE 14-continued

| Example | Starting cyclo-pentenone of Example | Starting trityloxy--1-alkyne of Example | Product Hydroxy Prostenoic Acid or Ester |
|---|---|---|---|
| 320 | 53 | 278 | Ethyl 7-nor-9-oxo-16-hydroxy-13-trans-prostenoate |
| 321 | 53 | 300 | Ethyl 7-nor-9-oxo-16-methyl-17-hydroxy-18,19,20-trinor-13-trans-prostenoate |
| 322 | 70 | 278 | Ethyl 2-fluoro-9-oxo-16-hydroxy-13-trans-prostenoate |
| 323 | 74 | 277 | Ethyl 7-a-homo-9-oxo-18-hydroxy-19,20-dinor-13-trans-prostenoate |
| 324 | 74 | 278 | Ethyl 7a-homo-9-oxo-16-hydroxy-13-trans-prostenoate |
| 325 | 79 | 278 | Ethyl 2-phenyl-9-oxo-16-hydroxy-13-trans-prostenoate |
| 326 | 79 | 299 | Ethyl 2-phenyl-9-oxo-16-hydroxy-17-ethyl-20-nor-13-trans-prostenoate |
| 327 | 31 | 304 | Ethyl 2-ethyl-9-oxo-20-hydroxy-13-trans-prostenoate |
| 328 | 273 | 278 | Ethyl 2-methyl-9-oxo-16-hydroxy-13-trans-prostenoate |
| 329 | 276 | 278 | Ethyl 3-thia-9-oxo-16-hydroxy-13-trans-prostenoate |
| 330 | 276 | 304 | Ethyl 3-thia-9-oxo-20-hyroxy-13-trans-prostenoate |
| 331 | 276 | 302 | Ethyl 3 thia-9-oxo-17-hydroxy-16-methyl-19,20-dinor-13-trans-prostenoate |
| 332 | 174 | 278 | Ethyl 9-oxo-11α-ethoxy-16-hydroxy-13-trans-prostenoate |
| 333 | 175 | 278 | Methyl 9-oxo-11α-methoxy-16-hydroxy-13-trans-prostenoate |
| 334 | 175 | 304 | Methyl 9-oxo-11α-methoxy-20-hydroxy-13-trans-prostenoate |
| 335 | 175 | 292 | Ethyl 9-oxo-11α-propoxy-6,7,18,19,20-pentanor-17-hydroxy-13-trans-prostenoate |
| 336 | 177 | 289 | Ethyl 9-oxo-11α-isopropoxy-5,6,7,19,20-pentanor-16-hydroxy-17-methyl-13-trans-prostenoate |
| 337 | 181 | 287 | Ethyl-9-oxo-7a,7b-bishomo-11α-isopropoxy-16-hydroxy-18,19,20-trinor-13-trans-prostenoate |
| 338 | 183 | 301 | Ethyl 2-ethyl-9-oxo-11α-butoxy-16-ethyl-17-hydroxy-18,19,20-trinor-13-trans-prostenoate |
| 339 | 185 | 304 | Ethyl 3,3-dimethyl-9-oxo-11α-methoxy-20-hydroxy-13-trans:prostenoate |
| 340 | 187 | 278 | Ethyl 3-oxa-9-oxo-11α-ethoxy-16-hydroxy-13-trans-prostenoate |
| 341 | 189 | 293 | Ethyl 2-fluoro-9-oxo-11α-propoxy-19-hydroxy-20-nor-13-trans-prostenoate |
| 342 | 191 | 298 | Ethyl 7-nor-9-oxo-11α-sec-butoxy-16-hydroxy-19-methyl-13-trans-prostenoate |
| 343 | 193 | 297 | Ethyl 7a-homo-9-oxo-11α-methoxy-17-hydroxy-19,20-dinor-13-trans-prostenoate |
| 344 | 195 | 290 | Ethyl 2-phenyl-9-oxo-11α-ethoxy-16-hydroxy-20-methyl-13-trans-prostenoate |
| 345 | 196 | 278 | Butyl 9-oxo-11α-methoxy-16-hydroxy-13-trans-prostenoate |
| 346 | 197 | 278 | Isopropyl 9-oxo-11α-methoxy-16-hydroxy-13-trans-prostenoate |
| 347 | 198 | 278 | Decyl 9-oxo-11α-methoxy-16-hydroxy-13-trans-prostenoate |
| 348 | 242a | 278 | 9-oxo-11α-methoxy-16-hydroxy-13-trans-prostenoic acid |
| 349 | 242a | 340 | 9-oxo-11α-methoxy-20-hydroxy-13-trans-prostenoic acid |
| 350 | 229 | 291 | 6,7-dinor-9-oxo-11α-methoxy-16-hydroxy-20-ethyl-13-trans-prostenoic acid |
| 351 | 230 | 294 | 5,6,7-trinor-9-oxo-11α-ethoxy-20-hydroxymethyl-13-trans-prostenoic acid |
| 352 | 231 | 302 | 7a,7b-bishomo-9-oxo-11α-methoxy-16-methyl-17-hydroxy-19,20-dinor-13-trans-prostenoic acid |
| 353 | 232 | 288 | 2-ethyl-9-oxo-11α-methoxy-16-hydroxy-20-nor-13-trans-prostenoic acid |
| 354 | 233 | 293 | 3,3-dimethyl-9-oxo-11α-methoxy-19-hydroxy-20-nor-13-trans-prostenoic acid |
| 355 | 234 | 278 | 3-oxa-9-oxo-11α-methoxy-16-hydroxy-13-trans-prostenoic acid |
| 356 | 235 | 295 | 2-fluoro-9-oxo-11α-methoxy-20-(2-hydroxyethyl)-13-trans-prostenoic acid |
| 357 | 236 | 296 | 7-nor-9-oxo-11α-methoxy-20-(3-hydroxypropyl)-13-trans-prostenoic acid |
| 358 | 237 | 298 | 7a-homo-9-oxo-11α-methoxy-16-hydroxy-19-methyl-13-trans-prostenoic acid |
| 359 | 238 | 303 | 2-phenyl-9-oxo-11α-methoxy-16-ethyl-17-hydroxy-19,20-dinor-13-trans-prostenoic acid |
| 360 | 239 | 278 | 9-oxo-11α-ethoxy-16-hydroxy-13-trans-prostenoic acid |
| 361 | 240 | 278 | 9-oxo-11α-propoxy-16-hydroxy-13-trans-prostenoic acid |
| 362 | 241 | 304 | 9-oxo-11α-isopropoxy-20-hydroxy-13-trans-prostenoic acid |
| 363 | 242 | 279 | 9-oxo-11α-n-butoxy-16-hydroxy-19,20-dinor-13-trans-prostenoic acid |
| 364 | 147 | 278 | 9-oxo-11α-hydroxy-16-hydroxy-13-trans-prostenoic acid |
| 365 | 147 | 288 | 9-oxo-11α-hydroxy-16-hydroxy-20-nor-13-trans- |

TABLE 14-continued

| Example | Starting cyclo-pentenone of Example | Starting trityloxy--1-alkyne of Example | Product Hydroxy Prostenoic Acid or Ester |
|---|---|---|---|
| | | | prostenoic acid |
| 366 | 147 | 289 | 9-oxo-11α-hydroxy-16-hydroxy-17-methyl-19,20-dinor-13-trans-prostenoic acid |
| 367 | 147 | 297 | 9-oxo-11α-hydroxy-17-hydroxy-19,20-dinor-13-trans-prostenoic acid |
| 368 | 147 | 298 | 9-oxo-11α-hydroxy-16-hydroxy-19-methyl-13-trans-prostenoic acid |
| 369 | 147 | 299 | 9-oxo-11α-hydroxy-16-hydroxy-17-ethyl-20-nor-13-trans-prostenoic acid |
| 370 | 147 | 277 | 9-oxo-11α-hydroxy-18-hydroxy-19,20-dinor-13-trans-prostenoic acid |
| 371 | 147 | 293 | 9-oxo-11α-hydroxy-19-hydroxy-20-nor-13-trans-prostenoic acid |
| 372 | 147 | 294 | 9-oxo-11α-hydroxy-20-hydroxymethyl-13-trans-prostenoic acid |
| 373 | 147 | 296 | 9-oxo-11α-hydroxy-20-(3-hydroxypropyl)-13-trans-prostenoic acid |
| 374 | 147 | 302 | 9-oxo-11α-hydroxy-16-methyl-17-hydroxy-19,20-dinor-13-trans-prostenoic acid |
| 375 | 148 | 291 | 9-oxo-11α-hydroxy-6,7-dinor-16-hydroxy-20-ethyl-13-trans-prostenoic acid |
| 376 | 149 | 304 | 9-oxo-11α-hydroxy-5,6,7-trinor-20-hydroxy-13-trans-prostenoic acid |
| 377 | 150 | 278 | 9-oxo-11α-hydroxy-7a,7b-bishomo-16-hydroxy-13-trans-prostenoic acid |
| 378 | 150 | 304 | 9-oxo-11α-hydroxy-7a,7b-bishomo-20-hydroxy-13-trans-prostenoic acid |
| 379 | 150 | 294 | 9-oxo-11α-hydroxy-7a,7b-bishomo-20-hydroxymethyl-13-trans-prostenoic acid |
| 380 | 151 | 287 | 9-oxo-11α-hydroxy-2-ethyl-16-hydroxy-18,19,20-trinor-13-trans-prostenoic acid |
| 381 | 152 | 278 | 9-oxo-11α-hydroxy-3,3-dimethyl-16-hydroyx-13-trans-prostenoic acid |
| 382 | 152 | 304 | 9-oxo-11α-hydroxy-3,3-dimethyl-20-hydroxy-13-trans-prostenoic acid |
| 383 | 153 | 278 | 9-oxo-11α-hydroxy-3-oxa-16-hydroxy-13-trans-prostenoic acid |
| 384 | 154 | 300 | 9-oxo-11α-hydroxy-2-fluoro-16-methyl-17-hydroxy-18,19,20-trinor-13-trans-prostenoic acid |
| 385 | 155 | 278 | 9-oxo-11α-hydroxy-7-nor-16-hydroxy-13-trans-prostenoic acid |
| 386 | 156 | 278 | 9-oxo-11α-hydroxy-7a-homo-16-hydroxy-13-trans-prostenoic acid |
| 387 | 157 | 291 | 9-oxo-11α-hydroxy-2-phenyl-16-hydroxy-20-ethyl-13-trans-prostenoic acid |
| 388 | 157a | 278 | 9-oxo-11α-hydroxy-2-methyl-16-hydroxy-13-trans-prostenoic acid |
| 389 | 157a | 304 | 9-oxo-11α-hydroxy-2-methyl-20-hydroxy-13-trans-prostenoic acid |
| 390 | 158 | 278 | Ethyl 9-oxo-11α-hydroxy-16-hydroxy-13-trans-prostenoate |
| 391 | 158 | 304 | Ethyl 9-oxo-11α-hydroxy-20-hydroxy-13-trans-prostenoate |
| 392 | 159 | 278 | Methyl 9-oxo-11α-hydroxy-16-hydroxy-13-trans-prostenoate |
| 393 | 160 | 294 | Ethyl 9-oxo-11α-hydroxy-6,7-dinor-20-hydroxy-methyl-13-trans-prostenoate |
| 394 | 161 | 298 | Ethyl 9-oxo-11αhydroxy-5,6,7-trinor 16-hydroxy-19-methyl-13-trans-prostenoate |
| 395 | 162 | 293 | Ethyl 9-oxo-11α-hydroxy-7a,7b-bishomo-19-hydroxy-20-nor-13-trans-prostenoate |
| 396 | 163 | 299 | Ethyl 9-oxo-11α-hydroxy-2-ethyl-16-hydroxy-17-ethyl-20-nor-13-trans-prostenoate |
| 397 | 164 | 297 | Ethyl 9-oxo-11α-hydroxy-3,3-dimethyl-17-hydroxy-19,20-dinor-13-trans-prostenoate |
| 398 | 165 | 294 | Ethyl 9-oxo-11α-hydroxy-3-oxa-20-hydroxy-methyl-13-trans-prostenoate |
| 399 | 166 | 304 | Ethyl 9-oxo-11α-hydroxy-2-fluoro-20-hydroxy-13-trans-prostenoate |
| 400 | 167 | 290 | Ethyl 9-oxo-11α-hydroxy-7-nor-16-hydroxy-20-methyl-13-trans-prostenoate |
| 401 | 168 | 289 | Ethyl 9-oxo-11α-hydroxy-7a-homo-16-hydroxy-17-methyl-19,20-dinor-13-trans-prostenoate |
| 402 | 169 | 297 | Ethyl 9-oxo-11α-hydroxy-2-phenyl-17-hydroxy-19,20-dinor-13-trans-prostenoate |
| 403 | 170 | 278 | Butyl 9-oxo-11α-hydroxy-16-hydroxy-13-trans-prostenoate |
| 404 | 170 | 304 | Butyl-9-oxo-11α-hydroxy-20-hydroxy-13-trans-prostenoate |
| 405 | 171 | 278 | Isopropyl 9-oxo-11α-hydroxy-16-hydroxy-13-trans-prostenoate |
| 406 | 171 | 304 | Isopropyl 9-oxo-11α-hydroxy-20-hydroxy-13-trans-prostenoate |
| 407 | 172 | 278 | Decyl 9-oxo-11α-hydroxy-16-hydroxy-13-trans-prostenoate |
| 408 | 172 | 304 | Decyl 9-oxo-11α-hydroxy-20-hydroxy-13-trans-prostenoate |
| 409 | 203 | 278 | Ethyl 9-oxo-11α-t-butyloxy-16-hydroxy-13-trans-prostenoate |
| 410 | 243 | 278 | Ethyl 9-oxo-11α(β-hydroxyethyoxy)-16-hydroxy-13-trans-prostenoate |

TABLE 14-continued

| Example | Starting cyclopentenone of Example | Starting trityloxy--1-alkyne of Example | Product Hydroxy Prostenoic Acid or Ester |
|---|---|---|---|
| 411 | 244 | 304 | Methyl 9-oxo-11α(β-hydroxyethoxy)-20-hydroxy-13-trans-prostenoate |
| 412 | 245 | 294 | Ethyl 9-oxo-11α(γ-hydroxypropoxy)-6,7-dinor-20-hydroxymethyl-13-trans-prostenoate |
| 413 | 246 | 298 | Ethyl 9-oxo-11α(β-hydroxyethoxy)-5,6,7-trinor-16-hydroxy-19-methyl-13-trans-prostenoate |
| 414 | 247 | 278 | 9-oxo-11α-(β-hydroxyethoxy)-16-hydroxy-13-trans-prostenoate |
| 415 | 247 | 304 | 9-oxo-11α-(β-hydroxyethoxy)-20-hydroxy-13-trans-prostenoic acid |
| 416 | 247 | 292 | 9-oxo-11α(β-hydroxyethoxy)-17-hydroxy-18,19,20-trinor-13-trans-prostenoic acid |
| 417 | 247 | 293 | 9-oxo-11α(βhydroxyethoxy)-19-hydroxy-20-nor-13-trans-prostenoic acid |
| 418 | 247 | 294 | 9-oxo-11α-(β-hydroethoxy)-20-hydroxymethyl-13-trans-prostenoic acid |
| 419 | 247 | 298 | 9-oxo-11α-(β-hydroxyethoxy)-16-hydroxy-19, methyl-13-trans-prostenoic acid |
| 420 | 248 | 296 | 9-oxo-11α-(β-hydroxyethoxy)-6,7-dinor-20-(3-hydroxypropyl)-13-trans-prostenoic acid |
| 421 | 249 | 299 | 9-oxo-11α-(β-hydroxyethoxy)-5,6,7,20-tetranor-16-hydroxy-17-ethyl-13-trans-prostenoic acid |
| 422 | 251 | 278 | 9-oxo-11α-(β-hydroxyethoxy)-7a,7b-bishomo-16-hydroxy-13-trans-prostenoic acid |
| 423 | 251 | 277 | 9-oxo-11α-(β-hydroxyethoxy)-7a,7b-bishomo-18-hydroxy-19,20-dinor-13-trans-prostenoic acid |
| 424 | 250 | 297 | Ethyl 9-oxo-11α-(β-hydroxyethoxy)-7a,7b-bishomo-17-hydroxy-19,20-dinor-13-trans-prostenoate |
| 425 | 253 | 287 | Ethyl 9-oxo-11α(γ-hydroxypropoxy)-2-ethyl-16-hydroxy-18,19,20-trinor-13-trans-prostenoate |
| 426 | 252 | 278 | 9-oxo-11α-(β-hydroxyethoxy)-2-ethyl-16-hydroxy-13-trans-prostenoic acid |
| 427 | 252 | 304 | 9-oxo-11α-(β-hydroxyethoxy)-2-ethyl-20-hydroxy-13-trans-prostenoic acid |
| 428 | 254 | 278 | 9-oxo-11α-(βhydroxyethoxy)-3,3-dimethyl-16-hydroxy-13-trans-prostenoic acid |
| 429 | 254 | 297 | 9-oxo-11α-(β-hydroxyethoxy)-3,5-dimethyl-17-hydroxy-19,20-dinor-13-trans-prostenoic acid |
| 430 | 255 | 293 | Ethyl 9-oxo-11α-(β-hydroxyethoxy)-3,3-dimethyl-19-hydroxy-20-nor-13-trans-prostenoate |
| 431 | 257 | 302 | Ethyl 9-oxo-11α-(γ-hydroxypropoxy)-3-oxa-16-methyl-17-hydroxy-19,20-dinor-13-trans-prostenoate |
| 432 | 256 | 278 | 9-oxo-11α-(β-hyddroxyethoxy)-3-oxa-16-hydroxy-13-trans-prostenoic acid |
| 433 | 258 | 278 | 9-oxo-11α-(β-hydroxyethoxy)-2-fluoro-16-hydroxy-13-trans-prostenoic acid |
| 434 | 258 | 304 | 9-oxo-11α-(β-hydroxyethoxy)-2-fluoro-20-hydroxy-13-trans-prostenoic acid |
| 435 | 258 | 291 | 9-oxo-11α-(β-hydroxyethoxy)-2-fluoro-16-hydroxy-20-ethyl-13-trans-prostenoic acid |
| 436 | 259 | 295 | Ethyl 9-oxo-11α-(β-hydroxyethoxy)-2-fluoro-20-(2-hydroxyethyl)-13-trans-prostenoate |
| 437 | 260 | 290 | 9-oxo-11α-(β-hydroxyethoxy)-7-nor-16-hydroxy-20-methyl-13-trans-prostenoic acid |
| 438 | 261 | 278 | 9-oxo-11α-(β-hydroxyethoxy)-7a-homo-16-hydroxy-13-trans-prostenoic acid |
| 439 | 262 | 293 | 9-oxo-11α-8β-hydroxyethoxy)-2-phenyl-19-hydroxy-20-nor-13-trans-prostenoic acid |
| 440 | 263 | 278 | Ethyl 9-oxo-11α-(β-hydroxyethoxy)-2-phenyl-16-hydroxy-13-trans-prostenoate |
| 441 | 264 | 278 | Butyl 9-oxo-11α-(β-hydroxyethoxy)-16-hydroxy-13-trans-prostenoate |
| 442 | 264 | 304 | Butyl 9-oxo-11α-(β-hydroxyethoxy)-20-hydroxy-13-trans-prostenoate |
| 443 | 265 | 278 | Isopropyl 9-oxo-11α-(βhydroxtyethoxy)-16-hydroxy-13-trans-prostenoate |
| 444 | 265 | 304 | Isopropyl 9-oxo-11α-(β-hydroxyethoxy)-20-hydroxy-13-trans-prostenoate |
| 445 | 266 | 278 | Decyl 9-oxo-11α-(β-hydroxyethoxy)-16-hydroxy-13-trans-prostenoate |
| 446 | 266 | 304 | Decyl 9-oxo-11α-(β-hydroxyethoxy)-20-hydroxy-13-trans-prostenoate |
| 447 | 267 | 278 | 9-oxo-11α-(β-hydroxypropoxy)-16-hydroxy-13-trans-prostenoic acid |
| 448 | 267 | 304 | 9-oxo-11α-(β-hydroxypropoxy)-20-hydroxy-13-trans-prostenoic acid |
| 449 | 267 | 303 | 9-oxo-11α-(β-hydroxypropoxy)-16-ethyl-17-hydroxy-19,20-dinor-13-trans-prostenoic acid |
| 450 | 269 | 278 | 9-oxo-11α-(4-hydroxybutoxy)-16-hydroxy-3-trans-prostenoic acid |
| 451 | 269 | 304 | 9-oxo-11α-(4-hydroxybutoxy)-20-hydroxy-13-trans-prostenoic acid |

EXAMPLES 451a–474

Saponification of the alkyl esters listed in Table 15 below by the method described in Example 283 is productive of the prostenoic acids of the table.

TABLE 15

| Example | Starting alkyl prostenoate of Example | Product Hydroxy Prostenoic Acid |
|---|---|---|
| 451a | 305 | 9-oxo-20-hydroxy-13-trans-prostenoic acid |
| 452 | 306 | 9-oxo-16-hydroxy-20-nor-13-trans-prostenoic acid |
| 453 | 307 | 9-oxo-16-hydroxy-20-methyl-13-trans-prostenoic acid |
| 454 | 308 | 9-oxo-17-hydroxy-19,20-dinor-13-trans-prostenoic acid |
| 455 | 309 | 9-oxo-20-hydroxymethyl-13-trans-prostenoic acid |
| 456 | 312 | 9-oxo-20-(3-hydroxypropyl)-13-trans-prostenoic acid |
| 457 | 314 | 5,6,7-trinor-9-oxo-20-(2-hydroxyethyl)-13-trans-prostenoic acid |
| 458 | 315 | 7a,7b-bishomo-9-oxo-16-hydroxy-13-trans-prostenoic acid |
| 459 | 316 | 7a,7b-bishomo-9-oxo-19,20-dinor-16-hydroxy-13-trans-prostenoic acid |
| 460 | 317 | 3,3-dimethyl-9-oxo-16-hydroxy-20-ethyl-13-trans-prostenoic acid |
| 461 | 318 | 3-oxa-9-oxo-16-hydroxy-13-trans-prostenoc acid |
| 462 | 319 | 3-oxa-9-oxo-19-hydroxy-20-nor-13-trans-prostenoic acid |
| 463 | 320 | 7-nor-9-oxo-16-hydroxy-13-trans-prostenoic acid |
| 464 | 321 | 7-nor-9-oxo-16-methyl-17-hydroxy-18,19,20-trinor-13-trans-prostenoic acid |
| 465 | 322 | 2-fluoro-9-oxo-16-hydroxy-13-trans-prostenoic acid |
| 466 | 323 | 7a-homo-9-oxo-18-hydroxy-19,20-dinor-13-trans-prostenoic acid |
| 467 | 324 | 7a-homo-9-oxo-16-hydroxy-13-trans-prostenoic acid |
| 468 | 325 | 2-phenyl-9-oxo-16-hydroxy-13-trans-prostenoic acid |
| 469 | 326 | 2-phenyl-9-oxo-16-hydroxy-17-ethyl-20-nor-13-trans-prostenoic acid |
| 470 | 327 | 2-ethyl-9-oxo-20-hydroxy-13-trans-prostenoic acid |
| 471 | 328 | 2-methyl-9-oxo-16-hydroxy-13-trans-prostenoic acid |
| 472 | 329 | 3 thia-9-oxo-16-hydroxy-13-trans-prostenoic acid |
| 473 | 330 | 3-thia-9-oxo-20-hydroxy-13-trans-prostenoic acid |
| 474 | 331 | 3-thia-9-oxo-17-hydroxy-16-methyl-19,20-dinor-13-trans-prostenoic acid |

EXAMPLE 475

Preparation of 16-hydroxy-9-oxo-prostanoic acid

A solution containing 1.4 g. (4.3 mmoles) of 16-hydroxy-9-oxo-13-trans-prostenoic acid (Example 286) in 45 ml. of absolute ethanol is hydrogenated using 650 mg. of 10% palladium or carbon. Filtration followed by evaporation of the solvent gives 1.31 g. of subject compound as an oil; $\nu$ max 5.78 (ketone carbonyl group) and 5.82 m$\mu$ (acid carbonyl group).

EXAMPLES 476–574

Hydrogenation of the 13-prostenoic acids and esters listed in the table below by the procedure described in Example 475 is productive of the prostanoic acids and esters of the table.

TabLE 16

| Example | Starting 13-prostenoic acid or ester of example | Product Prostanoic acid or ester |
|---|---|---|
| 476 | 318 | Ethyl 3-oxa-9-oxo-16-hydroxy-prostanoate |
| 477 | 319 | Ethyl 3-oxa-9-oxo-19-hydroxy-20-nor-prostanoate |
| 478 | 320 | Ethyl 7-nor-9-oxo-16-hydroxy-prostanoate |
| 479 | 321 | Ethyl 7-nor-9-oxo-16-methyl-17-hydroxy-18,19,20-trinor-prostanoate |
| 480 | 322 | Ethyl 2-fluoro-9-oxo-16-hydroxy-prostanoate |
| 481 | 324 | Ethyl 7a-homo-9-oxo-16-hydroxy-prostanoate |
| 482 | 325 | Ethyl 2-phenyl-9-oxo-16-hydroxy-prostanoate |
| 483 | 327 | Ethyl 2-ethyl-9-oxo-20-hydroxy-prostanoate |
| 484 | 328 | Ethyl 2-methyl-9-oxo-16-hydroxy-prostanoate |
| 485 | 305 | Ethyl 9-oxo-20-hydroxy-prostanoate |
| 486 | 306 | Ethyl 9-oxo-16-hydroxy-20-nor-prostanoate |
| 487 | 307 | Ethyl 9-oxo-16-hydroxy-20-methyl-prostanoate |
| 488 | 308 | Ethyl 9-oxo-17-hydroxy-19,20-dinor-13-prostanoate |
| 489 | 309 | Ethyl 9-oxo-20-hydroxymethyl-prostanoate |
| 490 | 310 | Butyl 9-oxo-16-hydroxy-19-methyl-prostanoate |
| 491 | 311 | Isopropyl 9-oxo-17-hydroxy-16-ethyl-prostanoate |
| 492 | 312 | Methyl 9-oxo-20-(3-hydroxy-propyl)-prostanoate |
| 493 | 313 | Decyl 9-oxo-16-hydroxy-prostanoate |
| 494 | 314 | Ethyl 5,6,7-trinor-9-oxo-20-(2-hydroxyethyl)-prostanoate |
| 495 | 315 | Ethyl 7a,7b-bishomo-9-oxo-16-hydroxy-prostanoate |
| 496 | 316 | Ethyl 7a,7b-bishomo-9-oxo-19,20-dinor-16-hydroxy-prostanoate |
| 497 | 317 | Ethyl 3,3-dimethyl-9-oxo-16-hydroxy-20-ethyl-prostanoate |
| 498 | 332 | Ethyl 9-oxo-11α-ethoxy-16-hydroxy-prostanoate |
| 499 | 333 | Methyl 9-oxo-11α-methoxy-16-hydroxy-prostanoate |
| 500 | 337 | Ethyl 9-oxo-7a,7b-bishomo-11α-isopropoxy-16-hydroxy-18,19,20-trinor-prostanoate |
| 501 | 338 | Ethyl 2-ethyl-9-oxo-11α-butoxy-16-ethyl-17-hydroxy-18,19,20-rinor-prostanoate |
| 502 | 339 | Ethyl 3,3-dimethyl-9-oxo-11α-methoxy-20-hydroxy-prostanoate |
| 503 | 340 | Ethyl 3-oxa-9-oxo-11α-ethoxy-16-hydroxy-prostanoate |
| 504 | 341 | Ethyl 2-fluoro-9-oxo-11α-propoxy-19-hydroxy-20-nor-prostanoate |
| 505 | 342 | Ethyl 7-nor-9-oxo-11α-sec-butoxy-16-hydroxy-19-methyl-prostanoate |
| 506 | 347 | Decyl 9-oxo-11α-methoxy-16-hydroxy-prostanoate |
| 507 | 348 | 9-oxo-11α-methoxy-16-hydroxy-prostanoic acid |
| 508 | 349 | 9-oxo-11α-methoxy-20-hydroxy-prostanoic acid |
| 509 | 352 | 7a,7b-bishomo-9-oxo-11α-methoxy-16-methyl-17-hydroxy-19,20-dinor-prostanoic acid |
| 510 | 353 | 2-ethyl-9-oxo-11α-methoxy-16-hydroxy-20-nor-prostanoic acid |
| 511 | 354 | 3,3-dimethyl9-oxo-11α-methoxy-19-hydroxy-20-nor-prostanoic acid |
| 512 | 355 | 3-oxa-9-oxo-11α-methoxy-16-hydroxy-prostanoic acid |
| 513 | 356 | 2-fluoro-9-oxo-11α-methoxy-20-(2-hydroxyethyl) prostanoic acid |
| 514 | 357 | 7-nor-9-oxo-11α-methoxy-20-(3-hydroxypropyl)-prostanoic acid |
| 515 | 358 | 7a-homo-9-oxo-11α-methoxy-16- |

TabLE 16-continued

| Example | Starting 13-prostenoic acid or ester of example | Product Prostanoic acid or ester |
|---|---|---|
| | | hydroxy-19-methyl-prostanoic acid |
| 516 | 359 | 2-phenyl-9-oxo-11α-methoxy-16-ethyl-17-hydroxy-19,20-dinor-prostanoic acid |
| 517 | 360 | 9-oxo-11α-ethoxy-16-hydroxy-prostanoic acid |
| 518 | 361 | 9-oxo-11α-propoxy-17-hydroxy-prostanoic acid |
| 519 | 362 | 9-oxo-11α-isopropoxy-20-hydroxy-prostanoic acid |
| 520 | 363 | 9-oxo-11α-n-butoxy-16-hydroxy-19,20-dinor-prostanoic acid |
| 521 | 364 | 9-oxo-11α-hydroxy-16-hydroxy-prostanoic acid |
| 522 | 365 | 9-oxo-11α-hydroxy-16-hydroxy-20-nor-prostanoic acid |
| 523 | 367 | 9-oxo-11α-hydroxy-17-hydroxy-19,20-dinor-prostanoic acid |
| 524 | 368 | 9-oxo-11α-hydroxy-16-hydroxy-19-methyl-prostanoic acid |
| 525 | 370 | 9-oxo-11α-hydroxy-18-hydroxy-19,20-dinor-prostanoic acid |
| 526 | 371 | 9-oxo-11α-hydroxy-19-hydroxy-20-nor-prostanoic acid |
| 527 | 372 | 9-oxo-11α-hydroxy-20-hydroxy-methyl-prostanoic acid |
| 528 | 373 | 9-oxo-11α-hydroxy-20-(3-hydroxypropyl)-prostanoic acid |
| 529 | 374 | 9-oxo-11α-hydroxy-16-methyl-17-hydroxy-19,20-dinor-prostanoic acid |
| 530 | 375 | 9-oxo-11α-hydroxy-6,7-dinor-16-hydroxy-20-ethyl-prostanoic acid |
| 531 | 377 | 9-oxo-11α-hydroxy-7a,7b-bishomo-16-hydroxy-prostanoic acid |
| 532 | 378 | 9-oxo-11α-hydroxy-7a,7b-bishomo-20-hydroxy-prostanoic |
| 533 | 381 | 9-oxo-11α-hydroxy-3,3-dimethyl-16-hydroxy-prostanoic acid |
| 534 | 382 | 9-oxo-11α-hydroxy-3,3-dimethyl-20-hydroxy-prostanoic acid |
| 535 | 383 | 9-oxo-11α-hydroxy-3-oxa-16-hydroxy-prostanoic acid |
| 536 | 384 | 9-oxo-11α-hydroxy-2-fluoro-16-methyl-17-hydroxy-18,19,20-trinor-prostanoic acid |
| 537 | 385 | 9-oxo-11α-hydroxy-7-nor-16-hydroxy-prostanoic acid |
| 538 | 386 | 9-oxo-11α-hydroxy-7a-homo-16-hydroxy-prostanoic acid |
| 539 | 387 | 9-oxo-11α-hydroxy-2phenyl-16-hydroxy-20-ethyl-prostanoic acid |
| 540 | 388 | 9-oxo-11α-hydroxy-2-methyl-16-hydroxy-prostanoic acid |
| 541 | 389 | 9-oxo-11α-hydroxy-2-methyl-20-hydroxy-prostanoic acid |
| 542 | 390 | Ethyl 9-oxo-11α-hydroxy-16-hydroxy-prostanoate |
| 543 | 391 | Ethyl 9-oxo-11α-hydroxy-20-hydroxy-prostanoate |
| 544 | 400 | Ethyl 9-oxo-11α-hydroxy-7-nor-16-hydroxy-20-methyl-prostanoate |
| 546 | 403 | Butyl 9-oxo-11α-hydroxy-16-hydroxy-prostanoate |
| 547 | 407 | Decyl 9-oxo-11α-hydroxy-16-hydroxy-prostanoate |
| 548 | 408 | Decyl 9-oxo-11α-hydroxy-20-hydroxy-prostanoate |
| 549 | 409 | Ethyl 9-oxo-11α-t-butoxy-16-hydroxy-prostanoate |
| 550 | 410 | Ethyl 9-oxo-11α-(β-hydroxyethoxy)-16-hydroxy-prostanoate |
| 551 | 411 | Methyl 9-oxo-11α-(β-hydroxyethoxy-20-hydroxy-prostanoate |
| 552 | 414 | 9-oxo-11α-(β-hydroxyethoxy)-16-hydroxy-prostanoic acid |
| 553 | 415 | 9-oxo-11α-(β-hydroxyethoxy)-20-hydroxy-prostanoic acid |
| 554 | 417 | 9-oxo-11α-(β-hydroxyethoxy)-19-hydroxy-20-nor-prostenoic acid |
| 555 | 419 | 9-oxo-11α-(β-hydroxyethoxy-16-hydroxy-19-methyl-prostanoic acid |

TabLE 16-continued

| Example | Starting 13-prostenoic acid or ester of example | Product Prostanoic acid or ester |
|---|---|---|
| 556 | 422 | 9-oxo-11α-(β-hydroxyethoxy)-7a,7b-bishomo-16-hydroxy-prostanoic acid |
| 557 | 423 | 9-oxo-11α-(β-hydroxyethoxy-7a,7b-bishomo-18-hydroxy-29,20-dinor-prostanoic acid |
| 558 | 424 | Ethyl 9-oxo-11α-(β-hydroxyethoxy)-7a,7b-bishomo-17-hydroxy-19,20-dinor-prostanoate |
| 559 | 426 | 9-oxo-11α-(β-hydroxyethoxy)-2-ethyl-16-hydroxy-prostanoic acid |
| 560 | 427 | 9-oxo-11α-(β-hydroxyethoxy)-2-ethyl-20-hydroxy-prostanoic acid |
| 561 | 428 | 9-oxo-11α-(β-hydroxyethoxy)-3,3-dimethyl-16-hydroxy-prostanoic acid |
| 562 | 429 | 9-oxo-11α-(β-hydroxyethoxy)-3,3-dimethyl-17-hydroxy-19,20-dinor-prostanoic acid |
| 563 | 432 | 9-oxo-11α-(β-hydroxyethoxy)-3-oxa-16-hydroxy-prostanoic acid |
| 564 | 433 | 9-oxo-11α-(β-hydroxyethoxy)-2-fluoro-16-hydroxy-prostanoic acid |
| 565 | 434 | 9-oxo-11α-(β-hydroxyethoxy)-2-fluoro-20-hydroxy-prostanoic acid |
| 566 | 437 | 9-oxo-11α-(β-hydroxyethoxy)-7-nor-16-hydroxy-20-methyl-prostanoic acid |
| 567 | 438 | 9-oxo-11α-(β-hydroxyethoxy)-7a-homo-16-hydroxy-prostanoic acid |
| 568 | 439 | 9-oxo-11α-(β-hydroxyethoxy)-2-phenyl-19-hydroxy-20-nor-prostanoic acid |
| 569 | 445 | Decyl 9-oxo-11α-(β-hydroxyethoxy)-16-hydroxy-prostanoate |
| 570 | 446 | Decyl 9-oxo-11α-(β-hydroxyethoxy)-20-hydroxy-prostanoate |
| 571 | 447 | 9-oxo-11α-(β-hydroxypropoxy)-16-hydroxy-prostanoic acid |
| 572 | 448 | 9-oxo-11α-(β-hydroxypropoxy)-20-hydroxy-prostanoic acid |
| 573 | 450 | 9-oxo-11α-(4-hydroxybutoxy)-16-hydroxy-prostanoic acid |
| 574 | 451 | 9-oxo-11α-(4-hydroxybutoxy)-20-hydroxy-prostanoic acid |

EXAMPLE 575

Preparation of 9α,11α,20-trihydroxy-13-trans-prostenoic acid

To a stirred solution of 459 mg. (1.29 mmoles) of 11α,20-dihydroxy-9-oxo-13-trans-prostenoic acid (Example 280a) in 4.0 ml. of tetrahydrofuran is added 5.2 ml. of a 0.65M solution of lithium perhydro 9b-boraphenalyl hydride in tetrahydrofuran at −78° C. under nitrogen. The solution is stirred at −78° C. for 45 minutes and at ambient temperatures for 15 minutes. The solution is diluted with 10 ml. of water and extracted with ether. The extract is back-extracted with N/4 sodium bicarbonate solution. The combined aqueous phases are acidified with 4N hydrochloric acid, saturated with sodium chloride, and extracted with ether. The extract is washed with saturated sodium chloride solution, dried over magnesium sulfate, and concentrated. The residue is purified by thin layer chromatography on silica gel to give a colorless oil, ν max. = 3310 (hydroxyl groups), 1705 (acid carbonyl group), and 970 $cm^{-1}$ (trans-vinyl group).

EXAMPLES 576–678a

Reduction of the 9-oxo derivative listed in the table below with lithium perhydro-9β-boraphenyalyl hydride by the method described in Example 575 is productive of the 9α-hydroxy derivative of the table.

When the starting 9-oxo-derivative is an ester, the original ether extract is washed with brine, dried over magnesium sulfate, and concentrated. Chromatography of the residue on silica gel to separate the boron-containing compounds affords the product esters of the table.

TABLE 17

| Example | Starting 9-oxo derivative of Example | Product 9α-hydroxy Derivative |
|---|---|---|
| 576 | 305 | Ethyl 9α,20-dihydroxy-13-trans-prostenoate |
| 577 | 306 | Ethyl 9α,16-dihydrox-20-nor-13-trans-prostenoate |
| 578 | 307 | Ethyl 9α,16-dihydroxy-20-methyl-13-trans-prostenoate |
| 579 | 308 | Ethyl 9α,17-dihydroxy-19,20-dinor-13-trans-prostenoate |
| 580 | 309 | Ethyl 9αhydroxy-20-hydroxy-methyl-13-trans-prostenoate |
| 581 | 310 | Butyl 9α,16-dihydroxy-19-meythyl-13-trans-prostenoate |
| 582 | 311 | Isopropyl 9α,17-dihydroxy-16-ethyl-13-trans-prostenoate |
| 583 | 313 | Decyl 9α,16-dihydroxy-13-trans-prostenoate |
| 584 | 315 | Ethyl 7a,7b-bishomo-9α,16-dihydroxy-13-trans-prostenoate |
| 585 | 317 | Ethyl 3,3-dimethyl-9α,16-dihydroxy-20-ethyl-13-trans-prostenoate |
| 586 | 318 | Ethyl 3-oxa-9α,16-dihydroxy-13-trans-prostenoate |
| 587 | 320 | Ethyl 7-nor-9α,16-dihydroxy-13-trans-prostenoate |
| 588 | 323 | Ethyl 7a-homo-9α,18-dihydroxy-19,20-dinor-13-trans-prostenoate |
| 589 | 324 | Ethyl 7a-homo-9α,16-dihydroxy-13-trans-prostenoate |
| 590 | 326 | Ethyl 2-phenyl-9α,16-dihydroxy-17-ethyl-20-nor-13-trans-prostenoate |
| 591 | 328 | Ethy l2-methyl-9α,16-dihydroxy-13-trans-prostenoate |
| 592 | 329 | Ethyl 3-thia-9α,16-dihydroxy-13-trans-prostenoate |
| 593 | 330 | Ethyl 3-thia-9α,20-dihydroxy-13-trans-prostenoate |
| 594 | 332 | Ethyl 11α-ethoxy-9α,16-dihydroxy-13-trans-prostenoate |
| 595 | 333 | methyl 11α-methoxy-9α,16-dihydroxy-13-trans-prostenoate |
| 596 | 334 | Methyl 11α-methoxy-9α,20-dihydroxy-13-trans-prostenoate |
| 597 | 337 | Ethyl 7a,7b-bishomo-11α-isopropoxy-9α,16-dihydroxy-18,19,20-trinor-13-transprostenoate |
| 598 | 338 | Ethyl 2-ethyl-11α-butoxy-16-ethyl-9α,17-dihdroxy-18,19,20-trinor-13-trans-prostenoate |
| 599 | 339 | Ethyl 3,3-dimethyl-11α-methoxy-9α,20-dihydroxy-13-trans-prostenoate |
| 600 | 341 | Ethyl 2-fluoro-9-oxo-11α-propoxy-9α,19-dihydroxy-20-nor-13-trans-prostenoate |
| 601 | 342 | Ethyl 7-nor-11α-sec-butoxy-9α,16-dihydroxy-19-methyl-13-trans-prostenoate |
| 602 | 343 | Ethyl 7a-homo-11α-methoxy-9α,17-dihydroxy-19,20-dinor-13-trans-prostenoate |
| 603 | 347 | Decyl 11α-metoxy-9α,16-dihydroxy-13-trans-prostenoate |
| 604 | 348 | 11α-methyl-9α,16-dihydroxy-13-trans prostenoic acid |
| 605 | 349 | 11α-methoxy-9α,20-dihydroxy-13-trans-prostenoic acid |
| 606 | 351 | 5,6,7-trinor-9α-hydroxy-11α-ethoxy-20-hydroxymethyl-13-trans-prostenoic acid |

TABLE 17-continued

| Example | Starting 9-oxo derivative of Example | Product 9α-hydroxy Derivative |
|---|---|---|
| 607 | 352 | 7a,7b-bishomo-11α-methoxy-16-methyl-9α,17-dihydroxy-19,20-dinor-13-trans-prostenoic acid |
| 608 | 353 | 2-ethyl-11α-methoxy-9α,16-dihydroxy-20-nor-13-trans-prostenoic acid |
| 609 | 355 | 3-oxa-11α-methoxy-9α,16-dihydroxy-13-trans-prostenoic acid |
| 610 | 356 | 2-fluoro-9α-hydroxy-11α-methoxy-20-(2-hydroxyethyl)-13-trans-prostenoic acid |
| 611 | 357 | 7-nor-9α-hydroxy-11α-methoxy-20-(3-hydroxypropyl)-13-trans-prostenoic acid |
| 612 | 358 | 7a-homo-9-oxo-11α-methoxy-9α,16-dihydroxy-19-methyl-13-trans-prostenoic acid |
| 613 | 360 | 11α-ethoxy-9α,16-dihydroxy-13-trans-prostenoic acid |
| 614 | 361 | 11α-propoxy-9α,16-dihydroxy-13-trans-prostenoic acid |
| 615 | 362 | 11α-isopropoxy-9α,20-dihydroxy-13-trans-prostenoic acid |
| 616 | 363 | 11α-n-butoxy-9α,16-dihydroxy-19,20-dinor-13-trans-prostenoic acid |
| 617 | 364 | 9α,11α,16-trihydroxy-13-trans-prostenoic acid |
| 618 | 365 | 9α,11α,16-trihydroxy-20-nor-13-trans-prostenoic acid |
| 619 | 366 | 9α,11α,16-trihydroxy-17-methyl-19,20-dinor-13-trans-prostenoic acid |
| 620 | 367 | 9α,11α,17-trihydroxy-19,20-dinor-13-trans-prostenoic acid |
| 621 | 368 | 9α,11α,16-trihydroxy-19-methyl-13-trans-prostenoic acid |
| 622 | 369 | 9α,11α,16-trihydroxy-17-ethyl-20-nor-13-trans-prostenoic acid |
| 623 | 370 | 9α,11α,18-trihydroxy-19,20-dinor-13-trans-prostenoic acid |
| 624 | 371 | 9α,11α,19-trihydroxy-20-nor-13-trans-prostenoic acid |
| 625 | 372 | 9α,11α-dihydroxy-20-hydroxy-methyl-13-trans-prostenoic acid |
| 626 | 373 | 9α,11α-dihydroxy-20-(3-hydroxy-propyl)-13-trans-prostenoic acid |
| 627 | 374 | 9α,11α,117-trihydroxy-16-methyl-19,20-dinor-13-trans-prostenoic acid |
| 628 | 375 | 9α,11α,16-trihydroxy-6,7-dinor-20-ethyl-13-trans-prostenoic acid |
| 629 | 376 | 9α,11α,20-trihydroxy-5,6,7-trinor-13-trans-prostenoic acid |
| 630 | 377 | 9α,11α,16-trihydroxy-7a,7b-bishomo-13-trans-prostenoic acid |
| 631 | 378 | 9α,11α,20-trihydroxy-7a,7b-bishomo-13-trans-prostenoic acid |
| 632 | 380 | 9α,11,16-trihydroxy-2-ethyl-18,19,20-trinor-13-trans-prostenoic acid |
| 633 | 381 | 9α,11α,16-trihydroxy-3,3-dimethyl-13-trans-prostenoic acid |
| 634 | 382 | 9α,11α,20-trihydroxy-3,3-dimethyl-13-trans-prostenoic acid |
| 635 | 383 | 9α,11α,16-trihydroxy-3-oxa-13-trans-prostenoic acid |
| 636 | 384 | 9α,11α,17-trihydroxy-2-fluoro-16-methyl-18,19,20-trinor-13-trans-prostenoic acid |
| 637 | 385 | 9α,11α,16-trihydroxy-7-nor-13-trans-prostenoic acid |
| 638 | 386 | 9α,11α,16-trihydroxy-7a-homo-13-trans-prostenoic acid |
| 639 | 387 | 9α,11α,16-trihydroxy-2-phenyl-20-ethyl-13-trans-prostenoic-acid |
| 640 | 388 | 9α,11α,16-trihydroxy-2-methyl-13-trans-prostenoic acid |

TABLE 17-continued

| Example | Starting 9-oxo derivative of Example | Product 9α-hydroxy Derivative |
|---|---|---|
| 641 | 389 | 9α,11α,20-trihydroxy-2-methyl-13-trans-prostenoic acid |
| 642 | 390 | Ethyl 9α,11α,16-trihydroxy-13-trans-prostenoate |
| 643 | 391 | Ethyl 9α,11α,20-trihydroxy-13-trans-prostenoate |
| 644 | 403 | Butyl 9α,11α,16-trihydroxy-13-trans-prostenoate |
| 645 | 407 | Decyl 9α,11α,16-trihydroxy-13-trans-prostenoate |
| 646 | 408 | Decyl9α.11α.20-trihydroxo-13-trans-prostenoate |
| 647 | 409 | Ethyl 11α-t-butoxy-9α.15-dihydroxy-13-trans-prostenoic acid |
| 648 | 410 | Ethyl 11α-(β-hydroxyethoxy)-9α16-dihydroxy-13-trans-prostenoate |
| 649 | 411 | Methyl 11α-(β-hydroxyethoxy)-9α.20-dihydroxy-13-trans-prostenoate |
| 650 | 414 | 9α.16-dihydroxy-11α-(β-hydroxyethoxy)-13-trans-prostenoic acid |
| 651 | 415 | 9α.20-dihydroxy-11-60 -(β-hydroxyethoxy)-13-trans-prostenoic acid |
| 652 | 416 | 9α,17-dihydroxy-(β-hydroxyethoxy)-18,19,20-trinor-13-trans-prostenoic acid |
| 653 | 417 | 9α.19-dihydroxy-(β-hydroxyethoxy)-20-nor-13-trans-prostenoic acid |
| 654 | 418 | 9α-hydroxy-(β-hydroxyethoxy)-20-hydroxymethyl-13-trans-prostenoic acid |
| 655 | 419 | 9α,16-dihydroxy-(β-hydroxyethoxy)-19-methyl-13-trans-prostenoic acid |
| 656 | 422 | 9α.16-dihydroxy-(β-hydroxyethoxy)-7a, 7b-bishomo-13-trans-prostenoic acid |
| 657 | 426 | 9α,16-dihydroxy-11α-(β-hydroxyethoxy)-2-ethyl-13-trans-prostenoic acid |
| 658 | 427 | 9α,20-dihydroxy-11α-(β-hydroxyetoxy)-2-ethyl-13-trans-prostenoic acid |
| 659 | 428 | 9α,16-dihydroxy-11α-(β-hydroxyethoxy)-3,3-dimethyl-13-trans-prostenoic acid |
| 660 | 432 | 9α,16-dihydroxy-11α-(β-hydroxyethoxy)-3-oxa-13-trans-prostenoic acid |
| 661 | 433 | 9α,16-dihydroxy-11α-(β-hydroxyethoxy)-2-fluoro-13-trans-prostenoic acid |
| 662 | 437 | 9α,16-dihydroxy-11α-(β-hydroxyethoxy)-7-nor-20-methyl-13-trans-prostenoic acid |
| 663 | 438 | 9α.16-dihydroxy-11α-(β-hydroxyethoxy)-7a-homo-13-trans-prostenoic acid |
| 664 | 440 | Ethyl9α,16-dihydroxy-11-α-(β-hydroxyethoxy)-2-phenyl-13-trans-prostenoic acid |
| 665 | 443 | Isoproyl 9α,16-dihydroxy-11α-β-hydroxyethoxy)-13-trans-prostenoic acid |
| 666 | 445 | Decyl 9α.16-dihydroxy-11-60 -(β-hydroxyethoxy)-13-trans-prostenoic acid |
| 667 | 446 | Decyl 9α-20-dihydroxy-11α-(β-Hydroxyethoxy)-13-trans-prostenoic acid |
| 668 | 447 | 9α.16-dihydroxy-11α-(β-hydroxypropoxy)-13-trns-prostenoic acid |
| 669 | 450 | 9α.16-dihydroxy-11-60 -(4-hydroxybutoxy)-13-trans-prostenoic acid |
| 670 | 507 | 9α.16-dihydroxy-11α-methoxyprostanoic acid |
| 671 | 511 | 9α.19-dihyroxy-3,3-dimethyl-11α-methoxy-20-nor-prostanoate |
| 672 | 531 | 9α,11α,16-trihydroxy-7a, 7b-bishomo-prostanoic acid |
| 673 | 527 | 9α,11α-dihydroxy-20-hydroxymethyl-prostanoic acid |
| 674 | 534 | 9α,11α,20-trihydroxy-3,3-dimethyl-prostanoic acid |
| 675 | 538 | 9α,11α,6-trihydroxy-7a-homoprostanoic acid |
| 676 | 547 | Decyl 9α,11α,16-trihydroxyprostanoate |
| 677 | 558 | hydroxyethoxy) prostanoic acid |
| 678 | 560 | 9α,20-dihydroxy-2-ethyl-11α-(β-hydroxyethoxy)-prostaoic acid |
| 678a | 745 | 9α,20-dihydroxy-13-trans-prostenoic acid |

EXAMPLE 679

Preparation of 9α/9β,11,20-trihydroxy-13-trans-prostenoic acid

To a stirred, ice-cold solution of 355 mg. (1.00 mmoles) of 11α,20-dihydroxy-9-oxo-13-trans-prostenoic acid (Example 280a) in 50 ml. of ethanol is added 409 mg. (10.8 mmoles) of sodium borohydride in small portions during 1 minute. The mixture is stirred at 0° C. for 5 minutes and at ambient temperature for 1.5 hour. The bulk of the ethanol is evaporated at room temperature, and the residue is treated with ether followed by dilute hydrochloric acid while cooling in an ice bath. The organic phase is separated and washed with water and saturated sodium chloride solution. The solution is dried over magnesium sulfate and concentrated. The residue is purified by thin layer chromatography on silica gel to give an oil, ν max. 3310 (hydroxyl groups), 1705 (acid carbonyl group), and 970 $cm^{-1}$ (trans vinyl group).

EXAMPLES 680–685

Treatment of the 9-oxo-derivatives listed in the table below with sodium borohydride in accordance with the procedure described in Example 674 is productive of the 9-hydroxy derivatives of the table. Each of these derivatives represents a mixture of 9α- and 9β-hydroxy compounds.

TABLE 18

| Example | Startng 9-oxo-derivative of Example | Product 9α/9β-hydroxy derivative |
|---|---|---|
| 680 | 305 | Ethyl9α/9β,20-dihydroxy-13-trans-prostenoate |
| 681 | 329 | Ethyl9α/9β,16-dihydroxy-3-thia-13-trans-prostenoate |
| 682 | 355 | 3-oxa 9α/9β16-dihyroxy-11α-methoxy-13-trans-prostanoic acid |
| 683 | 364 | 9α/9β,11α,16-trihydroxy-13-trans-prostenoic acid |
| 684 | 378 | 9α/9β,11α20-trihydroxy-7a,7b-bisheo-13-trans-prostenoic acid |
| 685 | 414 | 9α/9β16-dihydroxy-11-60 -(β-hydroxyethoxy)-13-trans-prostenoic acid |

EXAMPLE 686

Preparation of 20-hydroxy-9-oxo-10,13-trans-prostadienoic acid

A solution of 355 mg. (1.00 mmoles) of 11α,20-dihydroxy-9-oxo-13-trans-prostenoic acid (Example 280a) in 6.67 ml. of 1.5N hydrochloric acid and 13.3 ml. of tetrahydrofuran is allowed to stand at room temperature for 70 hours. The solution is treated with saturated sodium chloride solution and extracted with ether. The extract is washed successively with water and saturated sodium chloride solution and dried over magnesium sulfate. The crude product obtained after evaporation of the solvent is purified by chromatography on silica gel to give an oil, $\nu$ max$^{MeOH}$ = 217 m$\mu$ (9500); $\nu$ max = 1700 (acid carbonyl group), 1690 (ketone carbonyl group), 1585 (conjugated olefin group), and 965 cm$^{-1}$ (trans vinyl group).

EXAMPLES 687–737

Acid treatment by the procedure described in Example 686 of the 11$\alpha$-hydroxy-9-oxo derivatives listed in the table below is productive of the $\Delta^{10}$ derivatives of the table.

TABLE 19

| Example | Starting 11$\alpha$-hydroxy-9-oxo-derivative of Example | Product 9-0x0-10-prostenoic acids and esters |
|---|---|---|
| 687 | 387 | 9-oxo-2-phenyl-16-hydroxy-20-ethyl-10,13-trans-prostadienoic acid |
| 688 | 388 | 9-oxo-methyl-15-hydroxy-10,13-trans-prostadienoic acid |
| 689 | 389 | 9-oxo-2-methyl-20-hydroxy-10,13-trans-prostadienoic acid |
| 690 | 390 | Ethyl 9-oxo-16-hydroxy-10,13-trans-prostadienoate |
| 691 | 391 | Ethyl 9-oxo-20 hydroxy-10,13-trans-prostadienoate |
| 692 | 392 | Methyl 9-oxo-16-hydroxy-10,13-trans-prostadienoate |
| 693 | 393 | Ethyl9-oxo-6,7-dinor-20-hydroxy-methyl-10,13-trans-prostadienoate |
| 694 | 394 | Ethyl-9-oxo-5,6,7-trnor-16-hydroxy-19-methyl-10,13-trans-prostadienoate |
| 695 | 395 | Ethyl 9-oxo-7a,7b-bishomo-19-hydroxy-20-nor-10,13-trans-prostadienoate |
| 696 | 396 | Ethyl 9-oxo-2-ethyl-16-hydroxy-17-ethyl-20-nor-10,13-trans-prostadienoate |
| 697 | 397 | Ethyl 9-oxo-3,3-dimethyl-17-hydroxy-19,20-dinor-10,13-trans-prostadienoate |
| 698 | 398 | Ethyl 9-oxo-3-oxa-20-hydroxy-methyl-10,13-trans-prostadienoate |
| 699 | 399 | Ethyl 9-oxo-2-fluoro-20-hydroxy-10,13-trans-prostadienoate |
| 700 | 400 | Ethyl 9-oxo-7-nor-16-hydroxy-20-methyl-10,13-trans-prostadienoate |
| 701 | 401 | EThyl9-oxo-7a,homo-16-hydroxy-17-methyl-19,20-dinor-10,13-trans-prostadienoate |
| 702 | 402 | Ethyl 9-oxo-2-phenyl-17-hydroxy-19,20-dinor-10,13-trans-prostadienoate |
| 703 | 403 | Butyl 9-oxo-16-hydroxy-10,13-trans-prostadienoate |
| 704 | 404 | Butyl 9-oxo-20-hyroxy-10,13-trans-prostadienoate |
| 705 | 405 | Isopropyl 9-oxo-16-hydroxy-10,13-trans-prostadienoate |
| 706 | 406 | Isopropyl 9-oxo-20-hydroxy-10,13-trans-prostadienoate |
| 707 | 407 | Decyl 9-oxo-16-hydroxy-10,13-trans-prostadienoate |
| 708 | 408 | Decyl 9-oxo-20-hydroxy-10,13-trans-prostadienoate |
| 709 | 364 | 9-oxo-16-hyroxy-10,13-trans-prostadienoic acid |
| 710 | 365 | 9-oxo-16-hydroxy-20-nor-10,13-trans-prostadienoic acid |
| 711 | 366 | 9-oxo-16-hydroxy-17-methyl-19-20-dinor-10,13-trans-prostadienoic acid |
| 712 | 367 | 9-oxo-17-hydroxy-19,20-dinor-10,13-trans-prostadienoic acid |
| 713 | 368 | 9-oxo16-hydroxy-19-methyl-10-13-trans-prostadienoic acid |
| 714 | 369 | 9-oxo-16-hyroxy-17-ethyl-20-nor-10,13-trans-prostadienoic acid |
| 715 | 370 | 9-oxo-18-hydroxy-10,20-dinor-10,13-trans-prostadienoic acid |
| 716 | 371 | 9-oxo-19-hydroxy-nor-10,13-trans-prostadienoic acid |
| 717 | 372 | 9-oxo-20-hyroxymethyl-10,13-trans-prostadienoic acid |
| 718 | 373 | 9-oxo-20-(3-hydroxypropyl)-10-13-trans-prostadienoic acid |
| 719 | 374 | 9-oxo-16-methyl-17-hydroxy-19-20-dinor-10,13-trans-prostadienoic acid |
| 720 | 375 | 9-oxo-6,7-dinor-16-hydroxy-20-ethyl-10,13-trans-prostadienoic acid |
| 721 | 376 | 9-oxo-5,6,7-trinor-20-hyroxy-10,13-trans-prostadienoic acid |
| 722 | 377 | 9-oxo-7a,7b-bishomo-16-hydroxy-10,13-trans-prostadienoic acid |
| 723 | 378 | 9-oxo-7a,7b-bishomo-20-hydroxy-10,13-trans-prostadienoic acid |
| 724 | 380 | 9-oxo-2-ethyl-16-hydroxy-18,19.20-trinor-10,13-trans-prostdienoic acid |
| 725 | 381 | 9-oxo-3,3-dimethyl-16-hyroxy-10,13-trans-prostadienoic acid |
| 726 | 382 | 9-oxo-3,3-dimethyl-20-hydroxy-10,13-trans-prostadienoic acid |
| 727 | 383 | 9-oxo-3-oxa-16-hydroxy-10,13-trans-protadienoic acid |
| 728 | 384 | 9-oxo-2-fluoro-16-methyl-17-hydroxy-18,19,20-trinor-10,13-trans-prostadienoic acid |
| 729 | 385 | 9-oxo-7-nor-16-hyroxy-10,13-trans-oprostadienoic acid |
| 730 | 386 | 9-oxo-7a-homo-16-hydroxy-10,13-trans-prostadienoic acid |
| 731 | 521 | 9-oxo-16-hydroxy-10-prostenoic acid |
| 732 | 523 | 9-oxo-17-hydroxy-10,20-dinor-10-prostenoic acid |
| 733 | 526 | 9-oxo-19-hydroxy-20-nor-10-prostenoic acid |
| 734 | 529 | 9-oxo-17-hydroxy-16-methyl-10-20-dinor-10-prostenoic acid |
| 735 | 531 | 9-oxo-16-hydroxy 7a,7b-bishomo-10-prostenoic acid |
| 736 | 534 | 9-oxo-20-hydroxy-3,3-dimethy-10-prostenoic acid |
| 737 | 535 | 9-oxo-16-hydroxy-3-oxa-10-prostenoic acid |

EXAMPLE 738

Preparation of ethyl 9-oxo-13-trans-prostenoate

A solution of 1.102 g. of 1-octyne in 2 ml. of benzene is treated with 11.5 ml. of 15% diisobutylaluminum hydride in toluene and the solution is heated to 50° C. for 2 hours. The solution is cooled, its solvent is removed in vacuo, and the resulting oil is treated with 5.45 ml. of 5.10% methyl lithium in diethyl ether with ice cooling. To the resulting solution is added 1.830 g. of 2-(6-carbethoxyhexyl)-2-cyclopentenone (Example 13) and the solution is stirred at ambient temperatures for 18 hours. The solution is poured onto ice and dilute hydrochloric acid, and the mixture is extracted with diethyl ether. The organic phase is washed with dilute sodium bicarbonate, water, and saturated brine, dried, and evaporated. The residue is purified by chromatography on Florisil and distilltion to yield 1.878 g. of an oil, IR 1736 cm$^{-1}$ (ester and ketone carbonyls) 969 cm$^{-1}$ (trans vinyl group); NMR ($CDCl_3$) $\delta$ 5.14–5.87 (multiplet, 2H, vinyl protons, J trans = 15 Hz); Mass Spectrum, parent peak at 350 m$\mu$.

EXAMPLE 739

Preparation of ethyl 20-chloro-9-oxo-13-trans-prostenoate

In the manner described in Example 738, 2-(6-carbethoxyhexyl)-2-cyclopentenone (Example 13) is added to the reagent prepared from 8-chloro-1-octyne [W. J. Gensler and G. R. Thomas, J. Amer. Chem. Soc., 73, 4601 (1951)], diisobutylaluminum hydride, and methyl lithium. The crude product obtained by acid hydrolysis is purified by silica gel chromatography to give an oil, IR 1740 $cm^{-1}$ (ester and ketone carbonyls), 967 $cm^{-1}$ (trans vinyl group).

EXAMPLE 740

Preparation of ethyl 20-iodo-9-oxo-13-trans-prostenoate

A stirred mixture of 30 g. of ethyl 20-chloro-9-oxo-13-trans-prostenoate (Example 739), 25 g. of sodium iodide and 225 ml. of acetone is refluxed for 12 hours. The reaction mixture is concentrated, diluted with water, and extracted with ether. The extract is washed with saturated sodium chloride, dried, and evaporated to give an oil.

EXAMPLE 741

Preparation of 9-oxo-13-trans-prostenoic acid

A mixture of 0.140 g. of ethyl 9-oxo-13-trans-prostenoate (Example 738) and 0.072 g. of potassium hydroxide in 6 ml. of 1:1 aqueous methanol is stirred at ambient temperature for 17 hours. The resulting solution is acidified with hydrochloric acid, extracted with diethyl ether, and the organic phase is washed with water and saturated brine, dried, and the solvent removed to yield 0.128 g. of an oil, IR 1739 $cm^{-1}$ (ketone carbonyl) 1706 $cm^{-1}$ (acid carbonyl), 969 $cm^{-1}$ (trans vinyl group); NMR ($CDCl_3$) 5.34–5.67 (multiplet, 2H, vinyl protons, J trans = 15 Hz), 10.47 (broad singlet, 1H, carboxyl proton, exchangeable); Mass spectrum, parent peak at 322 mμ.

EXAMPLE 742

Preparation of ethyl 9,9-ethylenedioxy-20-iodo-13-trans-prostenoate

A solution of 25.2 g. of ethyl 20-iodo-9-oxo-13-trans-prostenoate (Example 740), 5.6 ml. of ethylene glycol and 110 mg. of p-toluenesulfonic acid monohydrate in 170 ml. of benzene is refluxed for 4 hours with azeotropic removal of water. The solution is concentrated to a volume of 50 ml. Column chromatography of the solution on Florisil with benzene gives a liquid, IR 1740 (ester carbonyl), 967 (trans vinyl group), and 952 $cm^{-1}$ (ethylene ketal).

EXAMPLE 743

Preparation of ethyl 20-benzoyloxy-9,9-ethylenedioxy-13-trans-prostenoate

A stirred mixture pf 7.80 g. (15 mmoles) of ethyl 9,9-ethylenedioxy-20-iodo-13-trans-prostenoate, (Example 742), 8.65 g. (60 mmoles) of sodium benzoate, and 100 ml. of dry methylformamide is maintained at 115° C. for 2 hours. The mixture is cooled, diluted with water and extracted with ether. The extract is washed successively with water, saturated sodium bicarbonate solution, and saturated sodium chloride solution. The extract is dried over magnesium sulfate. The crude product obtained by evaporation of the solvent is purified by chromatography on silica gel to give an oil, ν max. 1745 (alkanoate ester group), 1730 (benzoate ester group), 967 (trans vinyl group), and 948 $cm^{-1}$ (ethylenedioxy group).

EXAMPLE 744

Preparation of ethyl 20-benzoyloxy-9-oxo-13-trans-prostenoate

A solution of 5.35 g. (10.4 mmoles) of ethyl 20-benoyloxy-9,9-ethylenedioxy-13-trans-prostenoate (Example 743), 99 mg. (0.52 mmoles) of p-toluenesulonic acid monohydrate, and 40 ml. of acetone is allowed to stand at room temperature for 41 hours. The acetone is evaporated, and the residue is dissolved in ether. The solution is washed successively with sodium chloride solution, dilute sodium bicarbonate solution, and saturated sodium chloride solution. The solution is dried over magnesium sulfate and concentrated to give an oil, ν max. 1740 (ketone and alkanoate ester groups), 1730 benzoate ester group), and 967 $cm^{-1}$ (trans vinyl group).

EXAMPLE 745

Preparation of 20-hydroxy-9-oxo-13-trans-prostenoic acid

A solution of 4.75 g. (10.1 mmoles) of ethyl 20-benzoyloxy-9-oxo-13-trans-prostenoate (Example 744), 3.31 g. (50 mmoles) of 85% potassium hydroxide, 90 ml. of methanol, and 9 ml. of water is allowed to stand at room temperature for 24 hours. The solution is concentrated, diluted with water, and extracted with ether. The extract is washed with saturated sodium chloride solution, dried over magnesium sulfate, and concentrated. Column chromatography of the crude product on silica gel gives an oil, ν max. 1735 (ketone carbonyl group), 1710 (acid carbonyl group), and 967 $cm^{-1}$ (trans vinyl group).

EXAMPLE 746

Preparation of 9-oxo-18-hydroxy-19-hydroxy-13-trans-prostenoic acid

Inoculum Preparation:

A typical medium used to grow the inoculum was prepared according to the following formula:

| | |
|---|---|
| Sodium Nitrate | 3 grams |
| Dipotassium Hydrogen Phosphate | 1 gram |
| Magnesium Sulfate Heptahydrate | 5 grams |
| Potassium Chloride | 5 grams |
| Ferrous Sulfate Heptahydrate | 0.01 grams |
| Sucrose | 30 grams |
| Water to | 1000 milliliters |

The washed or scraped spores from an agar slant of Lederle Culture V89 (a strain of Diplodia malorum received from Centraalbureau voor Schirnmel cultures Baarn, Netherlands) is used to inoculate a flask containing 50 milliliters of the above medium in a 250 milliliter flask. The flask is placed on a rotary shaker and agitated vigorously for 5 days at 22° C.

Ten milliliters of the above first stage inoculum is introduced into two additional 250 milliliter flasks each containing 50 milliliters of medium, using 5 milliliters per flask. The flasks are incubated from 72 hours under the same conditions described for the first stage inoculum.

The 100 milliliters of second stage inoculum is used to inoculate a 4 liter glass fermentor containing 2 liters of sterile medium. The fermentor is aerated with sterile air while growth is continued for 72 hours at 25° C. This 2 liters of inoculum is used to inoculate a 40 liter tank fermentor containing 20 liters of liquid medium.

Fermentation:

A fermentation medium is prepared according to the same formula used for the inoculum medium. The fermentation medium is sterilized at 120° C. with steam at 20 pounds pressure for 45–60 minutes. The pH of the medium after sterilization is 6.6. Twenty liters of sterile medium in a 40 liter tank fermentor is inoculated with 2 liters of inoculum and the fermentation is carried out at 22° C. using lard oil, as necessary, as a defoaming agent. Aeration is supplied at the rate of 1.0 liters of sterile air per liter of mash per minute. The mash is agitated by air impeller driven at 400 revolutions per minute. At the end of 42 hours of fermentation time, a 5.15 gram sample of CL82, 680 dissolved in 150 milliliters of acetone is added to the fermentation. The fermentation is continued for an additional 5 hours whereupon the mash is harvested.

Isolation:

Twenty liters of fermentation mash (pH 7.5) is clarified by filtration through Hyflo, and the filtrate is extracted with three one-fifth volumes of chloroform after prior adjustment to pH 2.8 with hydrochloric acid. The combined chloroform extract is concentrated to a residue (4.85 g.) in vacuo, which after trituration with two 100 milliliter portions of cold hexane gives 4.28 g. residue.

This residue is further purified by adsorption chromatography on 100 grams of Davison Grade No. 62 silica gel slurry-packed in chloroform. The residue is dissolved in a small volume of chloroform, applied to the column and the column developed with a linear gradient between 1 liter each of chloroform and 10% ethanol-in-chloroform. Fractions of about 15 milliliters each are collected automatically. The progress of development is followed by monitoring the column effluent at 240 nanometers and also by thin layer chromatography of appropriate fractions. The fractions (47–80) containing the subject product are combined and concentrated to a residue (3.55 g.) in vacuo.

This residue is further purified by means of partition chromatography on 300 grams Celite. The column support is prepared by mixing 0.5 milliliters of the lower phase from the solvent system hexane-ethyl acetate-methanol-water (9:3:2:1) with each 1 gram of Celite. The residue from above, dissolved in 5 milliliters of lower phase is treated similarly and packed on top of the column which is then eluted with this upper phase. Fractions of about 60 milliliters each are collected automatically. The progress of development is followed by monitoring the column effluent at 270 nanometers and also by thin layer chromatography of appropriate fractions. The fractions (16–36) containing the desired compound are combined and concentrated to a residue (2.93 g.) in vacuo. This is dissolved in some chloroform, poured over 50 grams of Davison Grade No. 62 silica gel slurry-packed in chloroform, and, following washing the column with chloroform, it is eluted with 10% ethanol-in-chloroform to give, following evaporation, 2.9 grams product, which by nmr analysis contains a mixture of the 18-hydroxy and 19-hydroxy derivative in a ratio of about 3:1 to 1:1.

EXAMPLE 747

Preparation of 9-oxo-18,19-oxo-13-trans-prostenoic acid

A 1.5 gram sample of the product from Example 746 is dissolved in 20 milliliters of acetone and Jones Reagent (6.68 grams $CrO_3$ in 5.75 milliliters concentrated $H_2SO_4$ diluted to 25 milliliters with water) is added slowly with stirring until the color persist. The reaction mixture is stirred an additional 15 minutes whereupon the excess reagent is destroyed by the addition of methanol. The mixture is diluted to about 200 milliliters with water and extracted with three 50 milliliter portions of chloroform, which is then dried with anhydrous sodium sulfate and evaporated to give 1.5 grams of a pale yellow oil. This dissolved in some chloroform, poured over 30 grams of Davison Grade No. 62 silica gel slurry-packed in chloroform and, following washing the column with chloroform it is eluted with 5% ethanol-in-chloroform to give, following evaporation, 1.46 grams of subject product ketones.

EXAMPLES 748–750

Treatment of the 3-hydroxymethyl-1-alkynes, listed in Table 20 below, with triphenylmethyl bromide by the procedure described in Example 278 is productive of the 3-triphenylmethoxymethyl-1-alkynes of the Table.

TABLE 20

| Example | Starting 3-hydroxymethyl-1-alkyne | Product 3-triphenylmethoxymethyl-1-alkyne |
|---|---|---|
| 748 | 3-hydroxymethyl-1-hexyne* | 3-triphenylmethoxymethyl-1-hexyne |
| 749 | 3-hydroxymethyl-1-heptyne* | 3-triphenylmethoxymethyl-1-heptyne |
| 750 | 3-hydroxymethyl-1-octyne* | 3-triphenylmethoxymethyl-1-octyne |

*A. Schaap, L. Brandsma and J.F. Arens, Rec. trav. chim., 86. 393 (1967).

EXAMPLE 750a

Preparation of 1-chloro-3-triphenylmethoxy hexane

A stirred solution of 27.3 g. (0.20 moles) of 1-chloro-3-hexanol, 77.6 g. (0.24 moles) of triphenylmethyl bromide, 30.0 g. (0.28 moles of 2,6-lutidine, and 200 ml. of chlorobenzene is heated at 95° C. for 1 hour. The cooled mixture is treated with water, and the organic phase is washed successively with water and saturated sodium chloride solution. The solution is dried over magnesium sulfate and concentrated. Column chromatography of the residue on Florisil affords the subject compound as an oil, $\nu$ max. 1600, 1030, and 705 $cm^{-1}$ (triphenylmethoxy group).

EXAMPLE 751

Preparation of 5-triphenylmethoxy-1-octyne

To a stirred solution of 32.2 g. (85 mmoles) of 1-chloro-3-triphenylmethoxyhexane (Example 750a) in 25 ml. of dimethylsulfoxide (DMSO) is added a solution of 9.4 g. (102 mmoles) of lithium acetylide-ethylene diamine complex in 60 ml. of DMSO during 10 minutes while maintaining a temperature of 25°–30° C. After 3.5 hours the mixture is diluted with ether and treated successively with water and 4N hydrochloric acid while cooling in an ice bath. The phases are separated, and the aqueous phase is extracted with ether-petroleum ether. The combined extracts are washed successively with water and saturated sodium chloride solution dried over magnesium sulfate, and concentrated. The product is then purified by column chromtography of the residue of Florisil.

EXAMPLE 752–775

Conjugate addition of the alanates obtained by treatment of the triphenylmethoxy (trityloxy)-1-alkynes (indicated in the following table) with diisobutylaluminum hydride followed by methyl lithium, to the cyclopentenones of the table according to the method described in Example 280 followed by de-O-tritylation of the intermediate triphenylmethoxyprostenoates according to the method of Example 280a is productive of the prostenoic acids and esters of the table.

Those compounds isolated and identified in the table as prostenoic acids are prepared via the corresponding tetrahydropyran-2-yl esters and these compounds bearing a free hydoxy function at the 11α-position or as part of an 11α-(ω-hydroxyalkoxy) moiety are prepared via the corresponding tetrahydropyran-2-yl ethers. The hydroxy function in the β-side chain (that portion of the molecule deriving from the triphenylmethoxy-1-alkyne) of all compounds in the table are initially present in the molecule as the corresponding triphenylmethyl ethers. During the acetic acid treatment (de-O-tritylation step) the triphenylmethyl ether as well as the tetrahydropyran-2-yl ethers and esters functions are hydrolyzed to provide the corresponding free hydroxy and carboxylic acid groups of the compounds listed in the table.

TABLE 21

| Example | Starting cyclopentenones of Example | Starting trityloxy 1-alkyne of Example | Product Hydroxy Prostenoic Acid or Ester |
|---|---|---|---|
| 752 | 13 | 748 | Ethyl 9-oxo-15-hydroxymethyl-19,20-dinor-13-trans-prostenoate |
| 753 | 13 | 749 | Ethyl 9-oxo-15-hydroxymethyl-20-nor-13-trans-prostenoate |
| 754 | 13 | 750 | Ethyl 9-oxo-15-hydroxymethyl-13-trans-prostenoate |
| 755 | 13 | 751 | Ethyl 9-oxo-17-hydroxy-13-trans-prostenoate |
| 756 | 23 | 751 | Ethyl 9-oxo-17-hydroxy-7a,7b-bishomo-13-trans-prostenoate |
| 757 | 41 | 750 | Ethyl 9-oxo-15-hydroxymethyl-3,3-dimethyl-13-trans-prostenoate |
| 758 | 276 | 750 | Ethyl 9-oxo-15-hydroxymethyl-3-thia-13-trans-prostenoate |
| 759 | 276 | 751 | Ethyl 9-oxo-17-hydroxy-3-thia-13-trans-prostenoate |
| 760 | 147 | 751 | 9-oxo-11α,17-dihydroxy-13-trans-prostenoic acid |
| 761 | 147 | 748 | 9-oxo-11α-hydroxy-15-hydroxymethyl-19,20-dinor-13-trans-prostenoic acid |
| 762 | 147 | 749 | 9-oxo-11α-hydroxy-15-hydroxymethyl-20-nor-13-trans-prostenoic acid |
| 763 | 147 | 750 | 9-oxo-11α-hydroxy-15-hydroxymethyl-13-trans-prostenoic acid |
| 764 | 151 | 750 | 9-oxo-11α-hydroxy-15-hydroxymethyl-2-ethyl-13-trans-prostenoic acid |
| 765 | 152 | 751 | 9-oxo-11α,17-dihydroxy-3,3-dimethyl-13-trans-prostenoic acid |
| 766 | 153 | 751 | 9-oxo-11α,17-dihydroxy-3-oxa-13-trans-prostenoic acid |
| 767 | 153 | 750 | 9-oxo-11α-hydroxy-15-hydroxymethyl-3-oxa-13-trans-prostenoic acid |
| 768 | 154 | 750 | 9-oxo-11α-hydroxy-15-hydroxymethyl-2-fluoro-13-trans-prostenoic acid |
| 769 | 155 | 749 | 9-oxo-11α-hydroxymethyl-7,20-dinor-13-trans-prostenoic acid |
| 770 | 157 | 750 | 9-ox-11α-hydroxy-15-hydroxymethyl-2-phenyl-13-trans-prostenoic acid |
| 771 | 157a | 750 | 9-oxo-11α-hyddroxy-15-hydroxynethyl-7a-homo-13-trans-prostenoic acid |
| 772 | 242a | 750 | 9-oxo-11α-methoxy-15-hydroxymethyl-13-trans prostenoic acid |
| 773 | 242a | 751 | 9-oxo-11α-methoxy-17-hydroxy-13-trans-prostenoic acid |
| 774 | 247 | 750 | 9-oxo-11α-(2-hydroxyethoxy)-15-hydroxymethyl-13-trans-prostenoic acid |
| 775 | 247 | 751 | 9-oxo-11α-(2-hydroxyethoxy)-17-hydroxy-13-trans-prostenoic acid |

EXAMPLES 776–783

Saponification of the designated esters in Table 22 below by the method described in Example 283 is productive of the prostenoic acids of the table.

TABLE 22

| Example | Starting alkyl prostenoate of Example | Product Prostenoic Acid |
|---|---|---|
| 776 | 752 | 9-oxo-15-hydroxymethyl-19,20-dinor-13-trans-prostenoic acid |
| 777 | 753 | 9-oxo-15-hydroxymethyl-20-mor-13-trans-prostenoic acid |
| 778 | 754 | 9-oxo-15-hydroxymethyl-13,trans-prostenoic acid |
| 779 | 755 | 9-oxo-17-hydroxy-13-trans-prostenoic acid |
| 780 | 756 | 9-oxo-17-hydroxy-7a,7b-bishomo-13-trans-prostenoic acid |
| 781 | 757 | 9-oxo-15-hydroxymethyl-3,3-dimethyl-13-trans-prostenoic acid |
| 782 | 758 | 9-oxo-15-hydroxymethyl-3-thia-13-trans-prostenoic acid |
| 783 | 759 | 9-oxo-17-hydroxy-3-thia-13-trans-prostenoic acid |

EXAMPLES 784–815

Hydrogenation of the 13-prostenoic acids and esters listed in Table 23 below furnishes the prostanoic acids and esters of the table.

TABLE 23

| Example | Starting 13-prostanoic acid or ester of Example | Product Prostanoic Acid or Ester |
|---|---|---|
| 784 | 752 | ethyl 9-oxo-15-hydroxymethyl-19,20-dinor prostanoate |
| 785 | 753 | ethyl 9-oxo-15-hydroxymethyl-20-nor-prostanoate |
| 786 | 754 | ethyl 9-oxo-15-hydroxymethyl-prostanoate |
| 787 | 755 | ethyl 9-oxo-17-hydroxy-prostanoate |
| 788 | 757 | ethyl 9-oxo-17-hydroxymethyl-7a,7b-bishomo-prostanoate |
| 789 | 757 | ethyl 9-oxo-15-hydroxymethyl-3,3-dimethyl-prostanoate |
| 790 | 758 | ethyl 9-oxo-15-hydroxymethyl-3-thia-prostanoate |
| 791 | 759 | ethyl 9-oxo-17-hydroxy-3-thia-prostanoate |
| 792 | 760 | 9-oxo-11α,17-dihydroxy-prostanoic acid |
| 793 | 761 | 9-oxo-11α-hydroxy-16-hydroxy-methyl-19,20-dinor-prostanoic acid |
| 794 | 762 | 9-oxo-11α-hydroxy-15-hydroxy-methyl-20-nor-prostanoic acid |
| 795 | 763 | 9-oxo-11α-hydroxy-15-hydroxy-methyl-prostanoic acid |
| 796 | 764 | 9-oxo-11α-hydroxy-15-hydroxy-methyl-2-ethyl-prostanoic acid |
| 797 | 765 | 9-oxo-11α,17-dihydroxy-3,5-dimethyl-prostanoic acid |
| 798 | 766 | 9-oxo-11α,17-dihydroxy-3-oxa-prostanoic acid |
| 799 | 767 | 9-oxo-11α-hydroxy-15-hydroxy-methyl-3-oxa-prostanoic acid |
| 800 | 768 | 9-oxo-11α-hydroxy-15-hydroxymethyl-2-fluoro-prostanoic acid |
| 801 | 769 | 9-oxo-11α-hydroxy-15-hydroxy-methyl-7,20-dinor prostanoic acid |
| 802 | 770 | 9-oxo-11α-hydroxy-15-hydroxymethyl-2-phenyl-prostanoic acid |
| 803 | 771 | 9-oxo-11α-hydroxy-15-hydroxymethyl-7a-homo-prostanoic acid |
| 804 | 772 | 9-oxo-11α-methoxy-15-hydroxymethyl-prostanoic acid |
| 805 | 773 | 9-oxo-11α-methoxy-17-hydroxy-prostanoic acid |
| 806 | 774 | 9-oxo-11α-(2-hydroxyethoxy)-15-hydroxymethyl-prostanoic acid |
| 807 | 775 | 9-oxo-11α-(2-hydroxyethoxy)-17-hydroxy-prostanoic acid |
| 808 | 776 | 9-oxo-15-hydroxymethyl-19,20-dinor-prostanoic acid |
| 809 | 777 | 9-oxo-15-hydroxymethyl-20-nor |
| 810 | 778 | 9-oxo-15-hydroxymethyl-prostanoic acid |
| 811 | 779 | 9-oxo-17-hydroxy-prostanoic acid |
| 812 | 780 | 9-oxo-17-hydroxy-7a,7b-bishomo-prostanoic acid |
| 813 | 781 | 9-oxo-15-hydroxymethyl-3,3-dimethyl-prostanoic acid |
| 814 | 782 | 9-oxo-15-hydroxymethyl-3-thia-prostanoic acid |
| 815 | 783 | 9-oxo-17-hydroxy-3-thia-prostanoic acid |

EXAMPLES 816–868

Reduction of the 9-oxo-derivatives listed in Table 24 below with lithium perhydro-9β-boraphenalyl hydride by the procedure described in Example 575 is productive of the 9α-hydroxy derivative of the Table.

TABLE 24

| Example | Starting 9-oxo derivative of Example | Product 9α-hydroxy derivative |
|---|---|---|
| 816 | 752 | Ethyl 9α-hydroxy-15-hydroxy-methyl-19,20-dinor-13-trans-prostenoate |
| 817 | 753 | Ethyl 9α-hydroxy-15-hydroxy-methyl-20-nor-13-trans-prostenoate |
| 818 | 754 | Ethyl 9α-hydroxy-16-hydroxy-methyl-13-trans-prostenoate |
| 819 | 755 | Ethyl 9α,17-dihydroxy-13-trans-prostenoate |

TABLE 24-continued

| Example | Starting 9-oxo derivative of Example | Product 9α-hydroxy derivative |
|---|---|---|
| 820 | 756 | Ethyl 9α,17-dihydroxy 7a,7b-bishomo-113-trans-prostenoate |
| 821 | 757 | Ethyl 9α-hydroxy-15-hydroxy-methyl-3,3-dimethyl-13-trans-prostenoate |
| 822 | 758 | Ethyl 9α-hydroxy-15-hydroxy-methyl-3-thia-13-trans-prostenoate |
| 823 | 759 | Ethyl 9α,17-dihydroxy-3-thia-13-trans-prostenoate |
| 824 | 760 | 9α,11α,17-trihydroxy-13-trans-prostenoic acid |
| 825 | 761 | 9α,11α-dihydroxy-15-hydroxy-methyl-19,20-dinor-13-trans-prostenoic acid |
| 826 | 762 | 9α,11α-dihydroxy-15-hydroxy-methyl-20-nor-13-trans-prostenoic acid |
| 827 | 763 | 9α,11α-dihydroxy-15-hydroxy-methyl-13-trans-prostenoic acid |
| 828 | 764 | 9α,11α-dihydroxy-15-hydroxy-methyl-2-ethyl-13-trans-prostenoic acid |
| 829 | 765 | 9α,11α,17-trihydroxy-3,3-di-methyl-13-trans-prostenoic acid |
| 830 | 766 | 9α,11α,17-trihydroxy-3-oxa-13-trans-prostenoic acid |
| 831 | 767 | 9α,11α-dihydroxy-15-hydroxy-methyl-3-oxa-13-trans-prostenoic acid |
| 832 | 768 | 9α,11α-dihydroxy-15-hydroxy-methyl-2-fluoro-13-trans-prostenoic acid |
| 833 | 769 | 9α,11α-dihydroxy-15-hydroxy-methyl-7,20-dinor-13-trans-prostenoic acid |
| 834 | 770 | 9α,11α-dihydroxy-15-hydroxy-methyl-2-phenyl-13-trans-prostenoic acid |
| 835 | 771 | 9α,11α-dihydroxy-15-hydroxy-methyl-7a-homo-13-trans-prostenoic acid |
| 836 | 772 | 9α-hydroxy-11α-methoxy-15-hydroxymethyl-13-trans-prostenoic acid |
| 837 | 773 | 9α-hydroxy-11α-methoxy-9α,117-dihydroxy-13-trans-prostenoic acid |
| 838 | 774 | 9α-hydroxy-11α-(2-hydroxy-ethoxy)-15-hydroxymethyl-13-trans-prostenoic acid |
| 839 | 775 | 9α-hydrox-11α-(2-hydroxy-ethoxy)-17-hydroxy-13-trans-prostenoic acid |
| 840 | 776 | 9α-hydroxy-15-hydroxymethyl-19,20-dinor-13-trans-prostenoic acid |
| 841 | 777 | 9α-hydroxy-15-hydroxymethyl-20-nor-13-trans-prostenoic |
| 842 | 778 | 9α-hydroxy-15-hydroxymethyl-13-trans-prostenoic acid |
| 843 | 779 | 9α,17-dihydroxy-13-trans-prostenoic acid |
| 844 | 780 | 9α,17-dihydroxy-7a,7b-bishomo-13-trans-prostenoic acid |
| 845 | 781 | 9α-hydroxy-15-hydroxymethyl-3,3-dimethyl-13-trans-prostenoic acid |
| 846 | 782 | 9α-hydroxy-15-hydroxymethyl-3-thia-13-trans-prostenoic acid |
| 847 | 809 | 9α-hydroxy-15-hydroxymethyl-19,20-dinor-prostanoic acid |
| 848 | 809 | 9α-hydroxy-15-hydroxymethyl-20-nor-prostanoic acid |
| 849 | 810 | 9α-hydroxy-15-hydroxymethyl-prostanoic acid |
| 850 | 811 | 9α,17-dihydroxy-prostanoic acid |
| 851 | 812 | 9α,17-dihydroxy-7a,7b-bishomo-prostanoic acid |
| 852 | 813 | 9α-hydroxy-15-hydroxymethyl-3,3-dimethyl-prostanoic acid |
| 853 | 792 | 9α,11α,17-trihydroxy-prostanoic acid |
| 854 | 793 | 9α,11-dihydroxy-15-hydroxy-methyl-19,20-dinor-prostanoic acid |
| 855 | 794 | 9α,11-dihydroxy-15-hydroxy- |

TABLE 24-continued

| Example | Starting 9-oxo derivative of Example | Product 9α-hydroxy derivative |
|---|---|---|
| | | methyl-20-nor-prostanoic acid |
| 856 | 795 | 9α,11-dihydroxy-15-hydroxy-methyl-prostanoic acid |
| 857 | 796 | 9α,11-dihydroxy-15-hydroxy-methyl-2-ethyl-prostnoc acid |
| 858 | 798 | 9α,11α,17-trihydroxy-3-oxa-methyl-prostanoic acid |
| 859 | 798 | 9α,11α,17-trihydroxy-3-oxa-prostanoic acid |
| 860 | 799 | 9α,11α-dihydroxy-15-hydroxy-methyl-3-oxa-prostanoic acid |
| 861 | 800 | 9α,11α-dihydroxy-15-hydroxy-methyl-2-fluoro-prostanoic acid |
| 862 | 801 | 9α,11α-dihydroxy-15-hydroxy-methyl-7,20-dinor-prostanoic acid |
| 863 | 802 | 9α,11α-dihydroxy-15-hydroxy-methyl-2-phenyl-prostanoic acid |
| 864 | 803 | 9α,11α-dihydroxy-15-hydroxy-methyl-7a-homo-prostanoic acid |
| 865 | 804 | 9α-hydroxy-11α-methoxy-15-hydroxymethyl-prostanoic acid |
| 866 | 805 | 9α-hydroxy-11α-methyl-17-hydroxy-prostanoic acid |
| 867 | 806 | 9α,11α-(2-hydroxyethoxy)-15-hydroxymethyl-prostanoic acid |
| 868 | 807 | 9α,11α-(2-hydroxyethoxy)-17-hydroxy-prostanoic acid |

EXAMPLES 869–893

Acid treatment of the method described in Example 686 of the 11α-hydroxy-9-oxo derivatives listed in the table below furnishes the $\Delta^{10}$-derivatives of the table.

TABLE 25

| Example | Starting 11α-hydroxy-9-oxo-derivative of Example | Product 9-oxo-10-prostenoic acids and esters |
|---|---|---|
| 869 | 760 | 9-oxo-17-hydroxy-10,13-trans-prostadienoic acid |
| 870 | 761 | 9-oxo-15-hydroxymethyl-19,20-dinor-10,13-trans-prostadienoic acid |
| 871 | 762 | 9-oxo-15-hydroxymethyl-20-nor-10,13-trans-prostadienoic acid |
| 872 | 763 | 9-oxo-15-hydroxymethyl-10,13-trans-prostadienoic acid |
| 873 | 764 | 9-oxo-15-hydroxymethyl-2-ethyl-10,13-trans-prostadienoic acid |
| 874 | 765 | 9-oxo-17hydroxy-3,3-dimethyl-10,13trans-prostadienoic acid |
| 875 | 766 | 9-oxo-17-hydroxy-3-oxa-10,13-trans-prostadienoic acid |
| 876 | 767 | 9-oxo-15-hydroxymethyl3-oxa-10,13-trans-prostadienoic acid |
| 877 | 768 | 9-oxo-15-hydroxymethyl-2-fluoro-10,13-trans-prostadienoic acid |
| 878 | 770 | 9-oxo-15-hydroxymethyl-2-phenyl-10,13-trans-prostandienoic acid |
| 879 | 770 | 9-oxo-15-hydroxymethyl-2-phenyl-10,13-trans prostandienoic acid |
| 880 | 771 | 9-oxo-15-hydroxymethyl-7a-homo-10,13-trans- prostadienoic acid |
| 881 | 792 | 9-oxo-17-hydroxy-10-prostenoic acid |
| 882 | 793 | 9-oxo-15-hydroxymethyl-19,20-dinor-prostenoic acid |
| 883 | 794 | 9-oxo-15-hydroxymethyl-20-nor-prostenoic acid |
| 884 | 795 | 9-oxo-15-hydroxymethyl-prostenoic acid |
| 885 | 796 | 9-oxo-15-hydroxymethyl-2-ethyl-prostenoic acid |
| 886 | 797 | 9-oxo-17-hydroxy-3,3-dimethyl-prostenoic acid |
| 887 | 798 | 9-oxo-17-hydroxy-3-oxa-prostenoic acid |
| 888 | 799 | 9-oxo-15-hydroxymethyl-3-oxa-prostenoc acid |
| 889 | 800 | 9-oxo-15-hydroxymethyl-2-fluoro-prostenoic acid |
| 890 | 801 | 9-oxo-15-hydroxymethyl-7,20-dinor-prostenoic acid |
| 891 | 802 | 9-oxo-15-hydroxymethyl-2-phenyl-prostenoic acid |
| 892 | 803 | 9-oxo-15-hydroxymethyl-7a-homo-prostenoic acid |

EXAMPLE 893

Preparation of 4-hydroxy-1-octyne

A suspension of 24.3 g. (1.0 mole) of magnesium in 90 ml of dry ether is stirred at room temperature under nitrogen with 100 mg. of mercuric chloride. The reaction is initiated by the addition of 2 ml. of propargyl bromide and maintained by the dropwise addition of a solution of 119.5 g. (1.0 mole) of propargyl bromide and 107.7 g. (1.25 mole) of valeraldehyde in 300 ml. of dry ether. While the initial reaction is quite vigorous and is maintained at 30° C. only by cooling in an ice bath it may become necessary to heat the mixture to reflux temperature after about a third of the ether solution is added in order to maintain the reaction. After the addition is complete the reaction mixture is refluxed until most of the magnesium is dissolved (several hours) and the reaction mixture is decanted from excess magnesium into 1500 ml. of stirred ice-cold ammonium chloride solution. The ether layer is separated and the aqueous layer is extracted three times with 300 ml. portions of ether. The combined ether extract is washed with saturated sodium chloride solution, dried over magnesium sulfate and filtered. Evaporation of the ether under vacuum leaves about 115 mg. of yellow oil, which is distilled through a 15 cm. Vigreaux column at 18 mm. The fraction boiling at 81°–82° C. is collected (36 g.) and the higher-boiling and lower-boiling distillates may be redistilled to yield additional product. The infrared absorption spectrum shows at most a trace of allene (5.1 μ) and gas-liquid partition chromatography shows a purity of about 98% for the main fraction.

EXAMPLES 894–897

The product 1-alkyn-4-ols of Table 26 below are prepared by treatment of the aldehydes or ketones in Table 26 with propargyl magnesium bromide by the procedure described above in Example 893.

Table 26

| Example | Starting Aldehyde or Ketone | Product 1-Alkyn-4-ol |
|---|---|---|
| 894 | 2-trans-hexen-aldehyde | 4-hydroxy-5-trans-ene-1-nonyne |
| 895 | 3-cis-hexen-aldehyde* | 4-hydroxy-6-cis-ene-1-nonyne |
| 896 | 2-methylvaler-aldehyde | 4-hydroxy-5-methyl-1-octyne |
| 897 | 2-hexanone | 4-hydroxy-4-methyl-1-octyne |

*M. Winter, Melv. Chim. Acta, 46, 1792 (1963).

EXAMPLE 898

Preparation of 4-benzoyloxy-1-octyne

To a stirred solution of 63 g. (0.50 moles) of 4-hydroxy-1-octyne (Example 893) in 500 ml. of pyridine is added 77 g. (0.55 moles) of benzoyl chloride. After stirring for 1.5 hours the mixture is treated with 10 ml.

of water, allowed to stand for 15 minutes, and concentrated. A solution of the residue in ether is washed successively with ice-cold hydrochloric acid, water, sodium bicarbonate solution, and brine. The solution is dried over magnesium sulfate, filtered through Celite, and concentrated to give an oil, $\nu$ max. 3240 (terminal acetylene) and 1730 $cm^{-1}$ (benzoyloxy group).

EXAMPLE 899

Stereoselective hydrolysis of racemic 4-benzoyloxy-1-octyne by Rhizopus arrhizus An agar slant of R. arrhizus (MUMF 1638) is used to inoculate 7 shake flasks (250 ml. Erlenmeyer). Each flask contains 50 ml. of a medium consisting of 2% Edamine, 2% glucose, and 0.72% corn steep liquor in water with pH adjusted to 7.0. A total of 14 such flasks are incubated on a rotary shaker at 28° C. After 72 hours incubation, 50 mg. of racemic 4-benzoyloxy-1-octyne (Example 898) in 0.1 ml. of acetone is added to each flask. After 28 hours the flasks are harvested and worked up by extraction of the whole mash with an equal volume of chloroform. The combined extracts are dried over magnesium sulfate and concentrated. The resulting oil is chromatographed on a column of silica gel with hexane progressively enriched in ethyl acetate.

From fractions 3–6 is obtained 150 mg. of colorless oil, identical to 4-benzoyloxy-1-octyne, $[\alpha]_{D^{25}} = 5 \pm 1.0°$(C=0.91, ethyl acetate). This compound has the (S)-configuration.

From fractions 13–20 is obtained 75 mg. of colorless oil, identical to 4-hydroxy-1-octyne, $[\alpha]_{D^{25}} = -17 \pm 1.0°$(C=0.77, ethyl acetate). This compound has the (R)-configuration.

The strain of R. arrhizus utilized in this experiment is a higher fungus which grows steadily on a variety of artificial media at 20°–25° C. In this study of the taxonomic aspects of the culture, Petri dishes of potato-dextrose, malt extract, and cornmeal agars were inoculated and incubated at ambient room temperature for 10 days. Observations of cultural and morphological characteristics are recorded in the description below:

Colonies on Petri dishes of Potato-dextrose agar growing rapidly, covering the agar surface in 3–5 days and producing a thick, loose mat of grayish mycelium. Colony surface characterized by abundant black sporangia. Colony reverse grayish white. Colonies on Malt extract agar growing rapidly, covering the agar surface in 3–5 days. Mycelial mat thick, grayish-yellow. Colony surface becoming brownish-black from masses of sporangia. Colony reverse yellowish. Colonies on Cornmeal Agar very thin, whitish; spreading across agar surface. Cultures transparent with relatively few sporangia produced. Visibility of micromorphology is good on this medium. Rhizoids produced sparingly along stoloniferous hyphae. Generally two to three sporangiophores arose from rhizoids. Walls of sporangiophores olive brown, 14.0–20.0 $\mu$M in width at base, tapering slightly to apex; 0.5–1.5 mm in length. Sporangiophores terminated by spherical sporangia, 130–225 $\mu$M in diameter. Columellae hemispherical, 3–50 $\mu$M high by 50–70 $\mu$M wide. Spores brownish when mature, 6.0–8.5 $\mu$M $\times$ 4.5–6.0 $\mu$M. Spore walls conspicuously marked by longitudinal striations.

EXAMPLE 900

Preparation of (S)-4-hydroxy-1-octyne

A solution of 1.15 g. (5.0 mmoles) of (S)-4-benzoyloxy-1-octyne (Example 899) and 1.40 g. (25 mmoles) of potassium hydroxide in 50 ml. of 10:1 methanol-water is allowed to stand at room temperature for 24 hours. The bulk of the methanol is evaporated at room temperature, and the mixture is extracted with ether. The extract is washed with brine, dried over magnesium sulfate, and evaporated to give a colorless oil, identical to 4-hydroxy-1-octyne $[\alpha]_{D^{25}} = +17 \pm 1.0°$(C=0.77, ethyl acetate). This compound has the (S)-configuration.

EXAMPLE 901

Preparation of 3-bromo-1-octyne

To a stirred suspension of 600 g. of triphenylphosphine in 2000 ml. of acetonitrile, under nitrogen atmosphere, is added dropwise 118 ml. of bromide at a temperature not exceeding 35° C. After stirring for an additional hour, the supernatant liquid is decanted and taken to dryness. The solid residue is combined with the previous solid with 1500 ml. of dimethylformamide. The suspension is stirred at −20° C. and a solution of 200 g. of 1-octyne-3-ol in 300 ml. of dimethylformamide is added in three portions. The temperature is allowed to warm up slowly to 20° C. After 3 hours the solution is extracted with three 1600 ml portions of petroleum ether (b.p. 30°–60°). The combined extracts are washed with saturated sodium chloride solution, saturated sodium bicarbonate solution, and finally with saturated sodium chloride solution, dried with anhydrous magnesium sulfate and taken to dryness (bath 30°–35° C.). The residual oil was distilled to give 117 g. (39%) of product, b.p. 66°–68°/9mm.

EXAMPLE 902

Preparation of 3-hydroxymethyl-1-octyne

To a suspension of 2.54 g. of magnesium in 15 ml. of ether containing a few crystals of mercuric chloride, under nitrogen atmosphere, is added a small portion of 3-bromo-1-octyne in 20 ml. of ether. When reaction has set in, the flask is cooled in a 15° C. water bath, and the remainder of the halide in ether is added dropwise over a period of about 1 hour. When all of the halide has been added, stirring is continued for 15 minutes. The flask is then fitted with a glass tube which reaches almost to, but not below, the surface of the liquid. This tube connects directly with a round bottom flask containing about 20 mg. of paraformaldehyde which has been previously dried for 2 days in a vacuum desicator over phosphorous pentoxide. This flask contains an inlet tube for nitrogen. The reaction flask is immersed in an ice-bath, and the flask containing the paraformaldehyde is heated in an oil bath at 180°–200° C. The formaldehyde formed by depolymerization is carried over into the Grignard reagent by a slow current of dry nitrogen. At the end of 30–40 minutes formaldehyde addition is terminated and the reaction mixture stirred at room temperature for 18 hours.

The reaction mixture is then cooled in an ice-bath and saturated ammonium chloride is added, followed by water and then ether. The mixture is then acidified with 2M sulfuric acid. The organic phase is separated, washed with saturated sodium chloride solution, dried with anhydrous magnesium sulfate and the solvent removed in vacuo. The residue is distilled to give 4.4 g. of product; b.p. 91°–93°/9mm.

EXAMPLE 903–905

Treatment of the 3-hydroxymethyl-1-alkynes, listed in Table 27 below, with triphenylmethyl bromide by the procedure described in Example 278 is productive of the 3-triphenylmethoxymethyl-1-alkynes of the Table.

TABLE 27

| Example | Starting 3-hydroxymethyl-1-alkyne | Product phenylmethoxymethyl-1-alkyne |
|---|---|---|
| 903 | 3-hydroxymethyl-1-hexyne [1] | 3-triphenylmethoxymethyl-1-hexyne |
| 904 | 3-hydroxymethyl-1-heptyne[1] | 3-triphenylmethoxymethyl-1-heptyne |
| 905 | 3-hydroxymethyl-1-octyne[1] (Ex. 902) | 3-triphenylmethoxymethyl-1-octyne |

[1]A. Schaap. L. Brandsma and J.F. Arens. Rec. trav. chim. 86.393 (1967)

EXAMPLE 906

Preparation of 1-chloro-3-triphenylmethoxyhexane

A stirred solution of 27.3 g. (0.20 moles) of 1-chloro-3-hexanol, 77.6 g. (0.24 moles) of triphenylmethyl bromide, 30.0 g. (0.28 moles of 2,6-lutidine, and 200 ml. of chlorobenzene is heated at 95° C. for 1 hour. The cooled mixture is treated with water, and the organic phase is washed successively with water and saturated sodium chloride solution. The solution is dried over magnesium sulfate and concentrated. Column chromatography of the residue on Florisil affords the subject compound as an oil, λ max. 1600, 1030, and 705 $cm^{-1}$ (triphenylmethoxy group).

EXAMPLE 907

Preparation of 5-triphenylmethoxy-1-octyne

To a stirred solution of 32.2 g. (85 mmoles) of 1-chloro-3-triphenylmethoxyhexane (Example 906) in 25 ml. of dimethylsulfoxide (DMSO) is added a solution of 9.4 g. (102 mmoles) of lithium acetylide-ethylene diamine complex in 60 ml. of DMSO during 10 minutes while maintaining a temperature of 25°–30° C. After 3.5 hours the mixture is diluted with ether and treated successively with water and 4N hydrochloric acid while cooling in an ice bath. The phases are separated, and the aqueous phase is extracted with ether-petroleum ether. The combined extracts are washed successively with water and saturated sodium chloride solution, dried over magnesium sulfate, and concentrated. The product is then purified by column chromatography of the residue on Florisil.

EXAMPLES 908–912

The triphenylmethoxy substituted 1-alkynes listed in Table 28 below are prepared by the method of Example 278 from triphenylmethoxyl bromide and the corresponding hydroxy substituted 1-alkynes of the table.

TABLE 28

| Example | Starting hydroxy substituted alkyne of Example | Product triphenylmethoxy substituted alkyne |
|---|---|---|
| 908 | 894 | 4-triphenylmethoxy-5-trans-ene-1-nonyne |
| 909 | 895 | 4-triphenylmethoxy-6-cis-ene-1-nonyne |
| 910 | 896 | 4-triphenylmethoxy-5-methyl-1-octyne |
| 911 | 899 | (R)-4-triphenylmethoxy-1-octyne |

TABLE 28-continued

| Example | Starting hydroxy substituted alkyne of Example | Product triphenylmethoxy substituted alkyne |
|---|---|---|
| 912 | 900 | (S)-4-triphenylmethoxy-1-octyne |

EXAMPLE 913

Preparation of 1-iodo-4-triphenylmethoxy-trans-1-octene

To a stirred suspension of 1.78 g. (0.074 mole) of sodium borohydride in 200 ml. of dry glyme at −5° C. under nitrogen is added 15.8 g. (0.22 mole) of 2-methyl-2-butene and 16.2 g. (0.11 mole) of boron trifluoride etherate, and the mixture is stirred for 2 hours at −5° to 0° C. A solution of 37.5 g. (0.10 mole) of 4-trityloxy-1-octyne (Example 278) in 50 ml. of glyme is added to the cold solution during 5–10 minutes, and the solution is allowed to warm to 20° C. during 1.5 hours. The reaction mixture is cooled to 0° C., and 30 g. (0.4 mole) of dry trimethylamine-N-oxide is added during 5 minutes. On removing the cooling bath the temperature rises to 40° C., and the mixture is kept between 30°–40° C. for 1.5 hours. The suspension is poured rapidly into 1 liter of ice cold 15% sodium hydroxide solution during good stirring and a solution of 80 g. of iodine in 200 ml. of tetrahydrofuran is added immediately. Stirring is continued for 30 minutes without further cooling and the organic layer is separated. The aqueous layer is extracted with three 200 ml. portions of ether and the combined organic layers are washed successively with water, 5% sodium thiosulfate solution and saturated sodium chloride, dried over magnesium sulfate, filtered and evaporated to yield 50 g. of yellow oil. The bulk of the oil is dissolved in hexane and, after decantantation from a gummy solid the hexane solution is percolated through a 5.1 cm. diameter column at 1500 g. of alumina with additional hexane. Fractions containing the desired product are concentrated to a pale yellow oil (33 g.) which has n.m.r. and infrared spectra characteristics of the desired product.

EXAMPLES 914–922

Treatment of the triphenylmethoxy substituted 1-alkynes listed in Table 29 below with disiamylborane, prepared in situ from 2-methyl-2-butene, boron trifluoride and sodium borohydride, followed by trimethylamine N-oxide, and then sodium hydroxide and iodine all by the procedure described in Example 913 above furnishes the product triphenylmethoxy substituted 1-iodo-1-trans-alkenes of the table.

TABLE 29

| Example | Starting triphenylmethoxy substituted 1-alkyne of Example | Product 1-iodo-triphenylmethoxy substituted-1-trans-alkene |
|---|---|---|
| 914 | 905 | 1-iodo-3-triphenylmethoxymethyl-1-trans-octene |
| 915 | 907 | 1-iodo-5-triphenylmethoxy-1-trans-octene |
| 916 | 290 | 1-iodo-4-triphenylmethoxy-1-trans-nonene |
| 917 | 908 | 1-iodo-4-triphenylmethoxy-1,5-trans.trans-nonadiene |
| 918 | 910 | 1-iodo-4-triphenylmethoxy-5-methyl-1-trans-oxlene |
| 919 | 909 | 1-iodo-4-triphenylmethoxy-1-trans-16-cis- |

TABLE 29-continued

| Example | Starting triphenylmethoxy substituted 1-alkyne of Example | Product 1-iodo-triphenylmethoxy substituted-1-trans-alkene |
|---|---|---|
| | | nonadiene |
| 920 | 911 | (R)-1-iodo-4-triphenylmethoxy-1-trans-octene |
| 921 | 912 | (S)-1-iodo-4-triphenylmethoxy-1-trans-octene |
| 922 | 304 | 1-iodo-8-triphenylmethoxy-1-trans-octene |

EXAMPLE 923–924

Treatment of the 4-hydroxycyclopentenones, listed in Table 30 below, with dihydropyran by the procedure described in Example 158 is productive of the 4-tetrahydropyranyloxycyclopentenones of the table.

TABLE 30

| Example | Starting 4-hydroxycyclopentenone | Product 4-tetrahydropyranloxycyclopentenone |
|---|---|---|
| 923 | (R)-4-hydroxy-2-(6-carbomethoxyhexyl)cyclopent-2-en-1-one* | (R)-4-tetrahydropyranyloxy-2-(6-carbomethoxyhexyl)cyclopent-2-en-1-one |
| 924 | (S)-4-hydroxy-2-(6-carbomethoxyhexyl)cyclopent-2-en-1-one* | (S)-4-tetrahydropyranyloxy-2-(6-carbomethoxyhexyl)cyclopent-2-en-1-one |

*R. Pappo et al., Tetrahedron Letters, 1973.943

EXAMPLE 925

Preparation of 9-oxo-11α,17-dihydroxy-13-trans-prostenoic acid

To a stirred solution of the di-i-butylalkenylalane, prepared from 26.5 g. (72 mmoles) of 5-triphenylmethoxy-1-octyne (Example 907) and 60 ml. of 1.2 M di-i-butylaluminum hydride in hexane in 36 ml. of benzene according to the procedure of Example 281 is added 30 ml. of 2.2M methyllithium in ether.

The resulting alanate is reacted with 4-tetrahydropyranyloxy-2-(6-tetrahydropyranylcarboxyhexyl)-cyclopent-2-en-1-en-1-one (Example 147) according to the method of Example 280. The crude product thereby obtained is deblocking according to the method of Example 280a. The crude product is purified to provide the title compound as an oil, ν max. 1735 (ketone carbonyl group), 1710 (acid carbonyl group), and 967 $cm^{-1}$ (trans-vinyl group).

EXAMPLE 926

Preparation of 9-oxo-11α,16-dihydroxy-13-trans-prostenoic acid

To a stirred solution of 25.2 g. (48 mmoles) of 1-iodo-4-triphenylmethoxy-trans-1-octene (Example 913) in 50 ml. of toluene is added 24.0 ml. of 2.0M n-butyllithium in hexane at −70° C. After 1 hour this solution containing 4-triphenylmethoxy-trans-1-octenyl lithium is treated with 31.7 ml. of 1.45M trimethyl-aluminum in hexane at −40° C. and the resulting solution is stirred at 0° C. for 20 minutes.

To the above solution containing lithio trimethyl-(4-triphenylmethoxy-trans-1-octenyl)alanate is added a solution of 15.4 g. (39 mmoles) of 4-tetrahydropyranyloxy-2-(6-carbotetrahydropyranyloxyhexyl)-cyclopent-2-en-1-one (Example 147) in 50 ml. of ether at 0°–8° C. The mixture is stirred at 0° C. for 1 hour and 25° C. for 20 hours, diluted to 500 ml. with ether, and poured into a stired mixture of ice and 20 ml. of 37% hydrochloric acid. The aqueous phase is separated and extracted with ether. The combined organic phases are washed with water and brine, dried over magnesium sulfate, and concentrated to give an oil.

The crude product is dissolved in 440 ml. of 4:2:1 acetic acid-tetrahydrofuran-water, and the resulting solution is heated at 45° C. for 6 hours. The solvents are removed in vacuo at 20° C. to give a mixture of oil and crystals.

The crude product is purified by partition chromatography on acid-washed silica gel using the conjugate phases from benzene-methanol-water (15:5:2), with further purification by silica gel adsorption chromatography if necessary. The prostenoic acid is thereby obtained as an oil, ν max. (film) 3300 (hydroxy), 1735 (cyclopentenone), 1705 (carboxylic acid), and 967 $cm^{-1}$ (trans-olefin).

EXAMPLE 927

Preparation of ethyl 9-oxo-11α,16-dihydroxy-17-methyl-13-transprostenoate

To a stirred solution of 10.21 g. (20 mmoles) of iodo-5-methyl-4-triphenylmethoxy-trans-1-octene (Example 918) in 10 ml. of toluene is added 10 ml. of 2.0M n-butyllithium in hexane at −70° C. After 2 hours this solution containing 5-methyl-4-triphenylmethoxy-trans-1-octenyl lithium is added during 5 minutes at −75° C. to a stirred solution of 3.93 g. (10.0 mmoles) of cuprous iodide-tri-n-butylphoshine complex in 40 ml. of ether. The resulting solution is stirred at −50° C. for 30 minutes and then treated with a solution of 3.38 g. (10.0 mmoles) of cuprous iodide-tri-n-butylphosphine complex in 40 ml. of ether. The resulting solution is stirred at −50° C. for 30 minutes and then treated with a solution of 3.38 g. (10.0 mmoles) of 4-tetrahydropyranyloxy-2-(6-carbethoxyhexyl)-cyclopent-2-en-1-one (Example 158) in ml. of ether during 10 minutes at −45° C. The solution is allowed to warm to −20° C. during 1 hour and is stirred at 0° C. for 2 hours. The reaction mixture is quenched by pouring into iced ammonium chloride solution, and the product is extracted into ether. The extract is washed with brine, dried over magnesium sulfate, and concentrated to give an oil.

The crude product is dissolved in 100 ml. of 4:2:1 acetic acid-tetrahydrofuran-water, and the resulting solution is heated at 45° C. for 8 hours. The solvents are removed in vacuo at 20° C. to give a mixture of oil and crystals.

The crude product is purified by chromatography on acid-washed silica gel using benzene-ethyl acetate gradient elution to provide the title compound as an oil, ν max. 1740 (ketone and ester carbonyl groups) and 967 $cm^{-1}$ (trans-vinyl group).

EXAMPLE 928–937

Conjugate addition of the cuprates, obtained by treatment of the triphenylmethoxy (trityloxy)-1-iodo-trans-1-octene (indicated in the following table) with butyldilithium followed by cuprous iodide-tri-n-butylphosphine complex, to the cyclopentenones of the table according to the method described in Example 927 followed by de-O-tritylation of the intermediate triphenylmethoxy prostenoates according to the method of Example 927 is productive of the prostenoic acids or esters of the table.

These compounds isolated and identified in the table as prostenoic acids are prepared via the corresponding tetrahydropyran-2-yl esters and those compounds bearing a free hydroxy function at the 11α-position or as part of an 11α(ω-hydroxyalkoxy) moiety are prepared via the corresponding tetrahydropyran-2-yl ethers. The hydroxy function in the β-chain (that portion of the molecule deriving from the triphenylmethoxy-1-alkylene) of all compounds in the table are initially present in the molecule as the corresponding triphenylmethyl ethers. During the acetic acid treatment (de-O-tritylation step) the triphenylmethyl ether as well as the tetrahydropyran-2-yl ethers and esters functions are hydrolyzed to provide the corresponding free hydroxy and carboxylic acid groups of the compounds listed in the table.

TABLE 3

| Example | Starting cyclopentenone of Example | Starting 1-iodo-triphenylmethoxy substituted 1-trans-alkene of Example | Product Hydroxy Prostenoic Acid or Ester |
|---|---|---|---|
| 928 | 243 | 914 | Ethyl 9-oxo-11α-(β-hydroxyethoxy)-15-hydroxymethyl-13-trans-prostenoate |
| 929 | 234 | 915 | 3-oxa-9-oxo-11α-methoxy-17-hydroxy-13-trans-prostenoic acid |
| 930 | 147 | 916 | 9-oxo-11α,16-dihydroxy-20-[nor]methyl-13-trans-[prostenoate]prostenoic acid |
| 931 | 147 | 917 | 9-oxo-11α-dihydroxy-20-[nor]methyl-13,17-trans,trans-prostadienoic acid |
| 932 | 158 | 919 | Ethyl 9-oxo-11α,16-dihydroxy-20-[nor]methyl-13-trans-18-cis-prostadienoate |
| 933 | 147 | 918 | 9-oxo-11α,16-dihydroxy-17-methyl-13-trans-prostenoic acid |
| 934 | 923 | 920 | Methyl 9-oxo-(11R)11-hydroxy-16(R)-hydroxy-13-trans-prostenoate |
| 935 | 923 | 921 | Methyl 9-oxo-(11R)11-hydroxy-16(S)-16-hydroxy-13-trans-prostenoate |
| 936 | 924 | 920 | Methyl 9-oxo-(11S)11-hydroxy-(16R)-hydroxy-13-trans-prostenoate |
| 937 | 924 | 921 | Methyl 9-oxo-(11S)11-hydroxy-(16S)16-hydroxy-13-trans-prostenoate |

EXAMPLE 938

Preparation of 9α,11α,17-trihydroxy-13-trans-prostenoic acid

To a stirred solution of 1.366 g. of 9-oxo-11α,17-dihydroxy-13-trans-prostenoic acid (Example 925) in 19 ml. of tetrahydrofuran is added 10.0 ml. of a 1.0M solution of lithium tris-(sec-butyl)borohydride in 1:1 tetrahydrofuran pentane at −78° C. under nitrogen. The solution is stirred at −78° C. for 45 minutes and then is treated with 5 ml. of water. The mixture is stirred at 30° C. for 30 minutes, diluted with dilute sodium bicarbonate solution and extracted with ether. The aqueous phase is acidified with 4N hydrochloric acid, saturated with sodium chloride, and extracted with ethyl acetate. The extract is washed with brine, dried over magnesium sulfate and concentrated. The residue is purified by dry column chromatography with silica gel to give a colorless oil, ν max. = 3310 (hydroxyl groups), 1705 (carboxyl group), and 970 $cm^{-1}$ (trans-olefin group).

EXAMPLE 939

Preparation of methyl 9-oxo-16-hydroxy-8(12),13-trans-prostadienoate

A solution of 69 mg. of potassium carbonate (0.50 mmoles) and 81 mg. (0.25 mmoles) of methyl 9-oxo-11α-methoxy-16-hydroxy-13-trans-prostenoate (Example 333) in 25 ml. of 5:1 methanol-water is allowed to stand at room temperature for 24 hours. The solution is diluted with brine and extracted with ether. The extract is washed with brine, dried over magnesium sulfate and concentrated to give an oil, ν max. = 279 μ.

EXAMPLE 940–943

Treatment by the method described in Example 939 of the esters listed in the table below furnishes the $\Delta^{8(12)}$-derivatives of the table.

TABLE 32

| Example | Starting ester of Example | Product 9-oxo-8(12)-prostenoate ester |
|---|---|---|
| 940 | 430 | Ethyl 9-oxo-3,3-dimethyl-19-hydroxy-20-nor-8(12),13-trans-prostadienoate |
| 941 | 424 | Ethyl 9-oxo-7a,7b-bis-homo-17-hydroxy-19,20-dinor-8(12),13-trans-prostadienoate |
| 942 | 442 | Butyl 9-oxo-20-hydroxy-8(12(,13-trans-prostadienoate |
| 943 | 344 | Ethyl 2-phenyl-9-oxo-13-hydroxy-20-methyl-8(12)-13-trans-prostadienoate |

EXAMPLE 944

Preparation of 9-oxo-2-methyl-16-hydroxy-8(12),13-transprostadienoic acid

A solution of 0.56 g. (10 mmoles) of potassium hydroxide and 921 mg. (2.5 mmoles) of 9-oxo-11α-hydroxy-2-methyl-13-trans-prostenoic acid (Example 388) in 25 ml. of 10:1 methanol-water is allowed to stand at room temperature for 24 hours. The solution is diluted with brine, acidified with hydrochloric acid, and extracted with ethyl acetate. The extract is washed with brine, dried over magnesium sulfate, and concentrated to give an oil, ν max. = 279 mμ.

EXAMPLES 945–948

Treatment by the method described in Example 944 of the esters or acids listed in the Table below furnishes the $\Delta^{8(12)}$ prostenoic acids of the table.

TABLE 33

| Example | Starting ester of acid of Example | Product 9-oxo-8(12)-prostenoic acid |
|---|---|---|
| 945 | 536 | 9-oxo-2-fluoro-16-methyl-17-hydroxy-18,19,20-trinor-8(12)-prostenoic acid |
| 946 | 363 | 9-oxo-16-hydroxy-19,20-dinor-8(12),13- |

TABLE 33-continued

| Example | Starting ester of acid of Example | Product 9-oxo-8(12)-prostenoic acid |
|---|---|---|
| | | trans-prostadienoic acid |
| 947 | 444 | 9-oxo-20-hydroxy-8(12),13-trans-prostadienoic acid |
| 948 | 876 | 9-oxo-15-hyroxymethyl-3-oxa-8(12),13-trans-prostadienoic acid |

EXAMPLES 949–952

Conjugate addition of alanate obtained by treatment of the trityloxy-1-iodo-trans-1-octene (indicated in the following table) with n-butyllithium followed by trimethyl aluminum, to the cyclopentenones of the table according to the method described in Example 926 followed by the blocking group removal process of Example 926, is production of the prostenoate esters of the table.

TABLE 34

| Example | Starting cyclopentenone of Example | Starting 1-iodo-triphenylmethoxy substituted-1-trans-alkene of Example | Product Hydroxy Prostenoate Ester |
|---|---|---|---|
| 949 | 923 | 920 | Methyl 9-oxo-(11R)-hydroxy-(16R)-hydroxy-13-trans-prostenoate |
| 950 | 923 | 921 | Methyl 9-oxo-(11R)-hydroxy-(16S)16-hydroxy-13-trans-prostenoate |
| 951 | 924 | 920 | Methyl 9-oxo-(11S)11-hydroxy-(16R)16-hydroxy-13-trans-prostenoate |
| 952 | 924 | 921 | Methyl 9-oxo-(11S)11-hydroxy-(16S)16-hydroxy-13-trans-prostenoate |

EXAMPLES 953–956

Acid treatment by the procedure described in Example 686 of the 11α-hydroxy-9-oxo-derivative listed in the table below in productive of the $\Delta^{10}$ derivatives of the table.

TABLE 35

| Example | Starting 11α-hydroxy-9-oxo derivative of Example | Product 9-oxo-10-Prostenoate ester |
|---|---|---|
| 953 | 949 | Methyl 9-oxo-16(R)-hydroxy-10,13-trans-(8R,12R)-prostadienoate |
| 954 | 950 | Methyl 9-oxo-16(S)-hydroxy-10,13-trans-(8R,12R)-prostadienoate |
| 955 | 951 | Methyl 9-oxo-16(R)-hydroxy-10,13-trans-(8S,12S)-prostadienoate |
| 956 | 952 | Methyl 9-oxo-16(S)-hydroxy-10,13-trans-(8S,12S)-prostadienoate |

EXAMPLES 957–958

Treatment by the method described in Example 939 of the esters listed in the table below furnishes the $\Delta^{8(12)}$-derivatives of the table.

TABLE 36

| Example | Starting 11α-hydroxy-9-oxo derivative of Example | Product 9-oxo-10-prostenoate esters |
|---|---|---|
| 957 | 949 | (R)-Methyl-9-oxo-16-hydroxy-8(12),13-trans-prostadienoate |
| 958 | 950 | (S)-Methyl-9-oxo-16-hydroxy-8(12),13-trans-prostadienoate |

EXAMPLES 959–960

Treatment by the method described in Example 944 of the esters listed in the table below furnishes the $\Delta^{8(12)}$ prostenoic acids of the table.

TABLE 37

| Example | Starting 11α-hydroxy-9-oxo derivative of Example | Product 9-oxo-10-prostenoic acid |
|---|---|---|
| 959 | 951 | (R)-9-oxo-16-hydroxy-8(12),13-trans-prostadienoic acid |
| 960 | 952 | (S)-9-oxo-16-hydroxy-8(12),13-trans-prostadienoic acid |

EXAMPLES 962–964

Reduction of the 9-oxo derivatives listed in the table below with lithium perhydro-9b-borahenalyl hydride by the method described in Example 575 with modification indicated for Example 576 is productive of the 9α-hydroxy derivative of the table.

TABLE 38

| Example | Starting 9-oxo derivative of Example | Product 9α-hydroxy derivative |
|---|---|---|
| 961 | 949 | methyl(9S,11R,16R)-trihydroxy-13-trans-prostenoate |
| 962 | 950 | Methyl (9S,11R,16S)-trihydroxy-13-trans-prostenoate |
| 963 | 951 | Methyl (9R,11S,16R)-trihydroxy-13-trans-prostenoate |
| 964 | 952 | Methyl (9R,11S,16S)-trihydroxy-13-trans) prostenoate |

EXAMPLES 965–968

Reduction of the 9-oxo derivatives listed in the table below with sodium borohydride by the method described in Example 679 followed by separation of the 9α- and 9β-hydroxy derivatives by chromatography on silica gel is productive of the named 9β-hydroxy derivatives of the table.

TABLE 39

| Example | Starting 9-oxo derivative of Example | Product 9β-hydroxy derivative |
|---|---|---|
| 965 | 949 | Methyl (9R, 11R, 16R)-trihydroxy-13-trans-prostenoate |
| 966 | 950 | Methyl (9R,11R,16S)-trihydroxy-13-trans-prostenoate |
| 967 | 951 | Methyl (9S,11S,16R)-trihydroxy-13-trans-prostenoate |
| 968 | 952 | Methyl (9S,11S,16S)-trihydroxy-13-trans-prostenoate |

We claim:

1. An optically active compound of the formula:

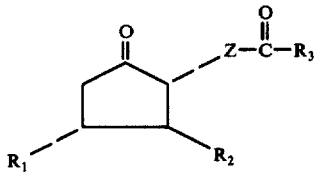

or a racemic compound of that formula and the mirror image thereof wherein $R_1$ is selected from the group consisting of hydroxy, [lower alkoxy, tetrahydropyranyloxy, lower alkanoyloxy,] *methoxy, ethoxy and* ω-hydroxy substituted [lower] alkoxy [and ω-tetrahydropyranyloxy substituted lower alkoxy] *having from 2 to 4 carbon atoms;* $R_2$ is a moiety selected from the group consisting of those of the formulae:

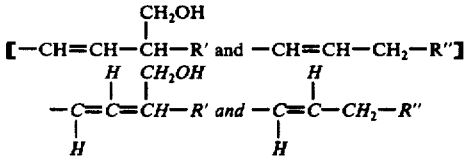

wherein R′ is selected from the group consisting of [a straight chain alkyl group having from 2 to 10 carbon atoms and a straight chain alkyl group having from 2 to 6 carbon atoms and having one branched alkyl group of from 1 to 3 carbon atoms] *n-propyl, n-butyl and n-pentyl,* and R″ is *a moiety* selected from the group consisting of [a straight chain alkyl group having from 2 to 10 carbon atoms and substituted with an hydroxy group, a straight chain alkyl group having from 2 to 6 carbon atoms and having one branched alkyl group of from 1 to 3 carbon atoms and substituted with an hydroxy group, a straight chain alkenyl group having from 2 to 10 carbon atoms and substituted with an hydroxy group and a straight chain alkenyl group having from 2 to 6 carbon atoms and having one branched alkyl group of from 1 to 3 carbon atoms and substituted with an hydroxy group;] *those of the formulae:*

$$-Y-(CH_2)_m-CH_3,\ -CH_2-Y-(CH_2)_2-CH_3-(CH_2)_5-OH,$$

$$-Y-\overset{trans}{CH=CH}-(CH_2)_p-CH_3 \text{ and}$$

$$-Y-CH_2-\overset{cis}{CH=CH}-(CH_2)_q-CH_3$$

*wherein m is an integer from 3 to 5, inclusive, p is an integer from 1 to 3, inclusive, q is zero, 1 or 2, and y is*

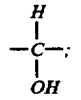

$R_3$ is selected from the group consisting of hydroxy[,] *and* alkoxy having from 1 to [12] *4* carbon atoms [and tetrahydropyranyloxy]; and Z is a divalent radical selected from the group consisting of those of the formulae:

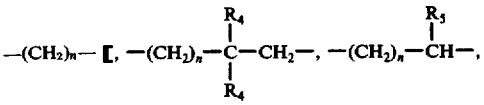

$$-(CH_2)_n-\ [,\ -(CH_2)_n-\overset{R_4}{\underset{R_4}{C}}-CH_2-,\ -(CH_2)_n-\overset{R_5}{CH}-,$$

$$-(CH_2)_n-O-CH_2- \text{ and } -(CH_2)_n-S-CH_2-]$$

$$\text{and } -(CH_2)_4-O-CH_2-$$

wherein n is an integer from [3] *6* to 8, inclusive[, $R_4$ is an alkyl group having up to 3 carbon atoms, and $R_5$ is selected from the group consisting of an alkyl group having up to 3 carbon atoms, a fluorine atom and a phenyl group]; and the pharmacologically acceptable cationic salts thereof when $R_3$ is hydroxy.

2. The optically active compound according to claim 1 wherein $R_1$ is hydroxy, $R_2$ is

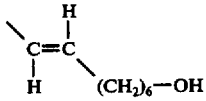

$R_3$ is hydroxy, and Z is $-(CH_2)_6-$; 1-9-oxo-11α,20-dihydroxy-13-trans-prostenoic acid.

3. The racemic compound according to claim 1 wherein $R_1$ is hydroxy, $R_2$ is

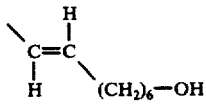

$R_3$ is hydroxy, and Z is $-(CH_2)_6-$; dl-9-oxo-11α,20-dihydroxy-13-trans-prostenoic acid.

4. The optically active compound according to claim 1 wherein $R_1$ is hydroxy, $R_2$ is

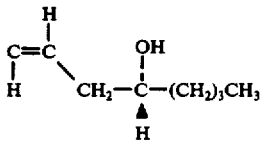

$R_3$ is hydroxy, and Z is —$(CH_2)_6$—; l-9-oxo-11α,16(S)-dihydroxy-13-trans-prostenoic acid.

5. The racemic compound according to claim 1 wherein $R_1$ is hydroxy, $R_2$ is

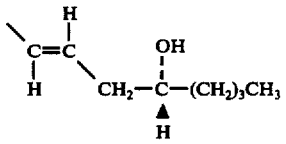

$R_3$ is hydroxy, and Z is —$(CH_2)_6$—; dl-9-oxo-11α,16*(S)*-dihydroxy-13-trans-prostenoic acid.

6. The mixture of the two racemic compounds according to claim 1 wherein $R_1$ is hydroxy, $R_2$ is

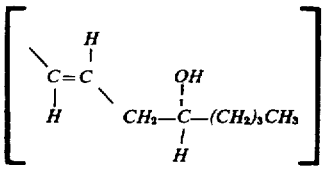

$R_3$ is hydroxy, and Z is —$(CH_2)_6$—; 9-oxo-11α,16-dihydroxy-13-trans-prostenoic acid.

7. The optically active compound according to claim 1 wherein $R_1$ is hydroxy, $R_2$ is

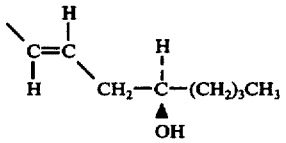

$R_3$ is hydroxy, and Z is —$(CH_2)_6$—; l-9-oxo-11α,16(R)-dihydroxy-13-trans-prostenoic acid.

8. The racemic compound according to claim 1 wherein $R_1$ is hydroxy, $R_2$ is

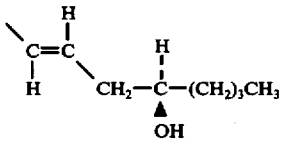

$R_3$ is hydroxy, and Z is —$(CH_2)_6$—; dl-9oxo-11α,16-[epidihydroxy] *(R)-dihydroxy*-13-trans-prostenoic acid.

9. The optically active compound according to claim 1 wherein $R_1$ is hydroxy, $R_2$ is

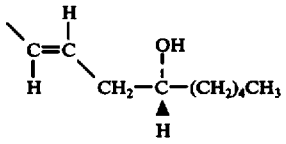

$R_3$ is hydroxy, and Z is —$(CH_2)_6$; l-9-oxo-11α,16(S)-dihydroxy-20-methyl-13-trans-prostenoic acid.

10. The racemic compound according to claim 1 wherein $R_1$ is hydroxy, $R_2$ is

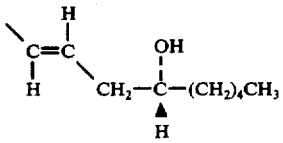

$R_3$ is hydroxy, and Z is —$(CH_2)_6$—; dl-9-oxo-11α,16*(S)*-dihydroxy-20-methyl-13-trans-prostenoic acid.

11. The mixture of the two racemic compounds according to claim 1 wherein $R_1$ is hydroxy, $R_2$ is

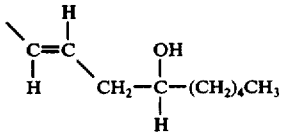

$R_3$ is hydroxy, and Z is —$(CH_2)_6$—; 9-oxo-11α,16-dihydroxy-20-methyl-13-trans-prostenoic acid.

12. The optically active compound according to claim 1 wherein $R_1$ is hydroxy, $R_2$ is

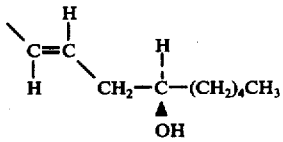

$R_3$ is hydroxy, and Z is —$(CH_2)_6$—; l-9-oxo-11α,16(R)-dihydroxy-20-methyl-13-trans-prostenoic acid.

13. The racemic compound according to claim 1 wherein $R_1$ is hydroxy, $R_2$ is

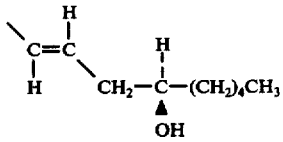

$R_3$ is hydroxy, and Z is —$(CH_2)_6$—; dl-9-oxo-11α,16*(R)*-[epi-]dihydroxy-20-methyl-13-trans-prostenoic acid.

14. The optically active compound according to claim 1 wherein $R_1$ is hydroxy, $R_2$ is

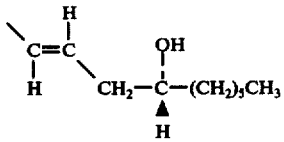

$R_3$ is hydroxy, and Z is —$(CH_2)_6$—; l-9-oxo-11α,16(S)-dihydroxy-20-ethyl-13-trans-prostenoic acid.

15. The racemic compound according to claim 1 wherein $R_1$ is hydroxy, $R_2$ is

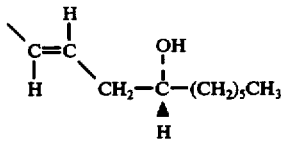

$R_3$ is hydroxy, and Z is —$(CH_2)_6$—; dl-9-oxo-11α,16*(S)*-dihydroxy-20-ethyl-13-trans-prostenoic acid.

16. The mixture of the two racemic compounds according to claim 1 wherein $R_1$ is hydroxy, $R_2$ is

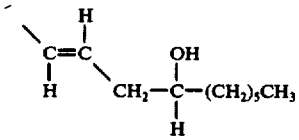

$R_3$ is hydroxy, and Z is —$(CH_2)_6$—; 9-oxo-11α,16-dihydroxy-20-ethyl-13-trans-prostenoic acid.

17. The optically active compound according to claim 1 wherein $R_1$ is hydroxy, $R_2$ is

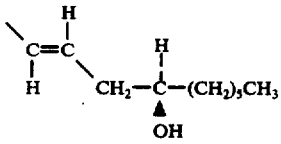

$R_3$ is hydroxy, and Z is —$(CH_2)_6$—; l-9-oxo-11α,16(R)-dihydroxy-20-ethyl-13-trans-prostenoic acid.

18. The racemic compound according to claim 1 wherein $R_1$ is hydroxy, $R_2$ is

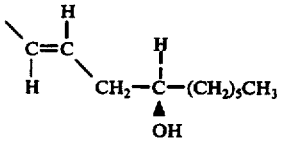

$R_3$ is hydroxy, and Z is —$(CH_2)_6$—; dl-9-oxo-11α,16[-epidihydroxy]*(R)-dihydroxy*-20-ethyl-13-trans-prostenoic acid.

19. The optically active compound according to claim 1 wherein $R_1$ is hydroxy, $R_2$ is

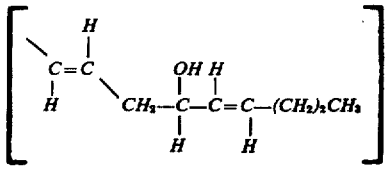

$R_3$ is hydroxy, and Z is —$(CH_2)_6$—; l-9-oxo-11α,16(S)-dihydroxy-20-methyl-13-trans,17-trans-prostadienoic acid.

[20. The racemic compound according to claim 1 wherein $R_1$ is hydroxy, $R_2$ is

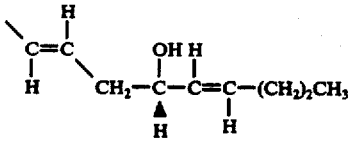

$R_3$ is hydroxy, and Z is —$(CH_2)_6$—; dl-9-oxo-11α,16(S)-dihydroxy-20-methyl-13-trans,17-trans-prostadienoic acid.]

21. The mixture of the two racemic compounds according to claim 1 wherein $R_1$ is hydroxy, $R_2$ is

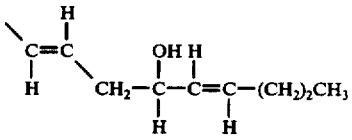

$R_3$ is hydroxy, and Z is —$(CH_2)_6$—; 9-oxo-11α,16-dihydroxy-20-methyl-13-trans,17-trans-prostadienoic acid.

[22. The optically active compound according to claim 1 wherein $R_1$ is hydroxy, $R_2$ is

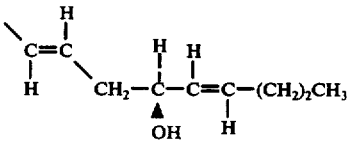

$R_3$ is hydroxy, and Z is —$(CH_2)_6$—; l-9-oxo-11α,16(R)-dihydroxy-20-methyl-13-trans,17-trans-prostadienoic acid.]

[23. The racemic compound according to claim 1 wherein $R_1$ is hydroxy, $R_2$ is

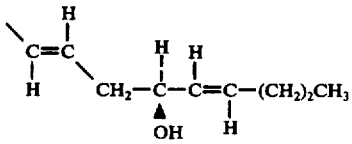

$R_3$ is hydroxy, and Z is —$(CH_2)_6$—; dl-9-oxo-11α,16-epidihydroxy-20-methyl-13-trans,17-trans-prostadienoic acid.]

24. The optically active compound according to claim 1 wherein $R_1$ is hydroxy, $R_2$ is

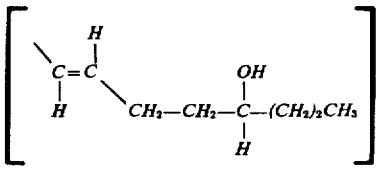

$R_3$ is hydroxy, and Z is —$(CH_2)_6$—; l-9-oxo-11α,17(S)-dihydroxy-13-trans-prostenoic acid.

[25. The racemic compound according to claim 1 wherein $R_1$ is hydroxy, $R_2$ is

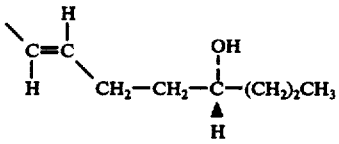

$R_3$ is hydroxy, and Z is —$(CH_2)_6$—; dl-9-oxo-11α,17-dihydroxy-13-trans-prostenoic acid.]

[26. The optically active compound according to claim 1 wherein $R_1$ is hydroxy, $R_2$ is

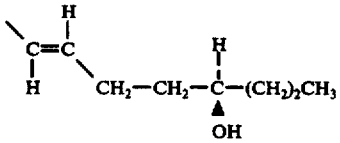

$R_3$ is hydroxy, and Z is —$(CH_2)_6$—; 1-9-oxo-11α,17(R)-dihydroxy-13-trans-prostenoic acid.]

[27. The racemic compound according to claim 1 wherein $R_1$ is hydroxy, $R_2$ is

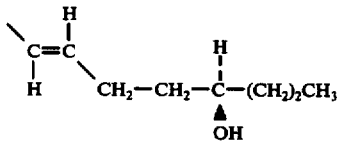

$R_3$ is hydroxy, and Z is —$(CH_2)_6$—; dl-9-oxo-11α,17-epi-dihydroxy-13-trans-prostenoic acid.]

28. The mixture of the two racemic compounds according to claim 1 wherein $R_1$ is hydroxy, $R_2$ is

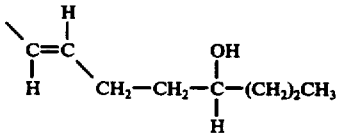

$R_3$ is hydroxy, and Z is —$(CH_2)_6$—; 9-oxo-11α,17-dihydroxy-13-trans-prostenoic acid.

29. The optically active compound according to claim 1 wherein $R_1$ is hydroxy, $R_2$ is

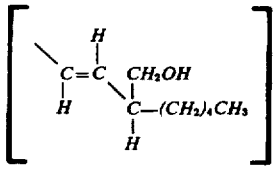

$R_3$ is hydroxy, and Z is —$(CH_2)_6$—; 1-9-oxo-11α-hydroxy-15(S)-hydroxymethyl-13-trans-prostenoic acid.

[30. The racemic compound according to claim 1 wherein $R_1$ is hydroxy, $R_2$ is

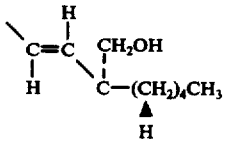

$R_3$ is hydroxy, and Z is —$(CH_2)_6$—; dl-9-oxo-11α-hydroxy-15-hydroxymethyl-13-trans-prostenoic acid.]

31. The mixture of the two racemic compounds according to claim 1 wherein $R_1$ is hydroxy, $R_2$ is

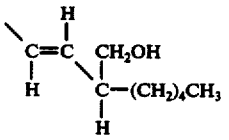

$R_3$ is hydroxy, and Z is —$(CH_2)_6$—; 9-oxo-11α-hydroxy-15-hydroxymethyl-13-trans-prostenoic acid.

[32. The optically active compound according to claim 1 wherein $R_1$ is hydroxy, $R_2$ is

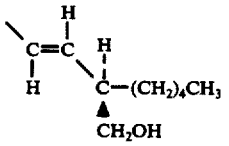

$R_3$ is hydroxy, and Z is —$(CH_2)_6$—; 1-9-oxo-11α-hydroxy-15(R)-hydroxymethyl-13-trans-prostenoic acid.]

[33. The racemic compound according to claim 1 wherein $R_1$ is hydroxy, $R_2$ is

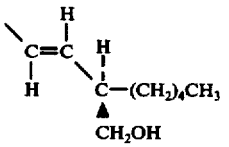

$R_3$ is hydroxy, and Z is —$(CH_2)_6$—; dl-9-oxo-11α-hydroxy-15-epi-hydroxymethyl-13-trans-prostenoic acid.]

*34. The optically active compound according to claim 1 wherein $R_1$ is hydroxy, $R_2$ is*

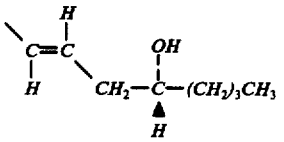

*$R_3$ is hydroxy, and Z is —$(CH_2)_4$—O—$CH_2$—; 1-9-oxo-11α,16(S)-dihydroxy-3-oxa-13-trans-prostenic acid.*

*35. The racemic compound according to claim 1 wherein $R_1$ is hydroxy, $R_2$ is*

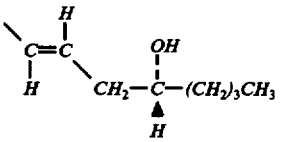

*$R_3$ is hydroxy, and Z is —$(CH_2)_4$—O—$CH_2$—; dl-9-oxo-11α,16(S)-dihydroxy-3-oxa-13-trans-prostenoic acid.*

*36. The mixture of the two racemic compounds according to claim 1 wherein $R_1$ is hydroxy, $R_2$ is*

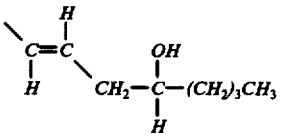

*$R_3$ is hydroxy, and Z is —$(CH_2)_4$—O—$CH_2$—; 9-oxo-11α,16-dihydroxy-3-oxa-13-trans-prostenoic acid.*

*37. The optically active compound according to claim 1 wherein $R_1$ is hydroxy, $R_2$ is*

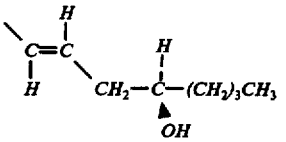

*$R_3$ is hydroxy, and Z is —$(CH_2)_4$—O—$CH_2$—; l-9-oxo-11α,16(R)-dihydroxy-3-oxa-13-trans-prostenoic acid.*

*38. The racemic compound according to claim 1 wherein $R_1$ is hydroxy, $R_2$ is*

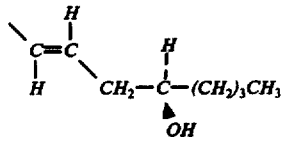

*$R_3$ is hydroxy, and Z is —$(CH_2)_4$—O—$CH_2$—; dl-9-oxo-11α,16(R)-dihydroxy-3-oxa-13-trans-prostenoic acid.*

*39. The optically active compound according to claim 1 wherein $R_1$ is hydroxy, $R_2$ is*

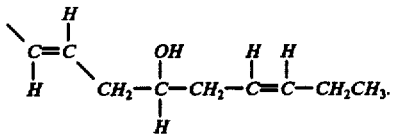

*$R_3$ is ethoxy, and Z is —$(CH_2)_6$—; l-ethyl 9-oxo-11α,16(S)-dihydroxy-20-methyl-13-trans,18-cis-prostadienoate.*

*40. The mixture of the two racemic compounds according to claim 1 wherein $R_1$ is hydroxy, $R_2$ is*

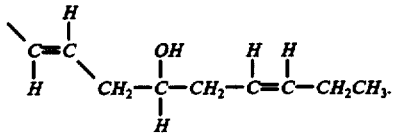

*$R_3$ is ethoxy, and Z is —$(CH_2)_6$—; ethyl 9-oxo-11α,16-dihydroxy-20-methyl-13-trans,18-cis-prostadienoate.*

*41. The optically active compound ethyl l-9-oxo-11α,16-dihydroxy-17-methyl-13-transprostenoate.*

*42. The racemic compound ethyl dl-9-oxo-11α,16-dihydroxy-17-methyl-13-transprostenoate.*

*43. The optically active compound l-9-oxo-11α,16-dihydroxy-17-methyl-13-trans-prostenoic acid.*

*44. The racemic compound dl-9-oxo-11α,16-dihydroxy-17-methyl-13-trans-prostenoic acid.*

*45. The optically active compound l-9-oxo-11α-hydroxy-16-hydroxy-17-methyl-19,20-dinor-13-trans-prostenoic acid.*

*46. The racemic compound dl-9-oxo-11α-hydroxy-16-hydroxy-17-methyl-19,20-dinor-13-trans-prostenoic acid.*

*47. The optically active compound l-9-oxo-11α-hydroxy-16-hydroxy-17-ethyl-20-nor-13-trans-prostenoic acid.*

*48. The racemic compound dl-9-oxo-11α-hydroxy-16-hydroxy-17-ethyl-20-nor-13-trans-prostenoic acid.*

* * * * *